United States Patent
Zhang et al.

(10) Patent No.: US 11,667,682 B2
(45) Date of Patent: Jun. 6, 2023

(54) SPLIT INTEIN MEDIATED PROTEIN POLYMERIZATION FOR MICROBIAL PRODUCTION OF MATERIALS

(71) Applicants: Fuzhong Zhang, St. Louis, MO (US); Christopher H. Bowen, St. Louis, MO (US); Bin Dai, St. Louis, MO (US)

(72) Inventors: Fuzhong Zhang, St. Louis, MO (US); Christopher H. Bowen, St. Louis, MO (US); Bin Dai, St. Louis, MO (US)

(73) Assignee: Washington University, St. Louis, MO (US)

( * ) Notice: Subject to any disclaimer, the term of this patent is extended or adjusted under 35 U.S.C. 154(b) by 593 days.

(21) Appl. No.: 16/713,643

(22) Filed: Dec. 13, 2019

(65) Prior Publication Data
US 2020/0354414 A1 Nov. 12, 2020

Related U.S. Application Data

(60) Provisional application No. 62/878,525, filed on Jul. 25, 2019, provisional application No. 62/779,386, filed on Dec. 13, 2018.

(51) Int. Cl.
| | |
|---|---|
| C07K 14/00 | (2006.01) |
| C07K 14/435 | (2006.01) |
| D01D 5/06 | (2006.01) |
| D01D 1/02 | (2006.01) |
| B29C 48/05 | (2019.01) |
| D01F 4/02 | (2006.01) |
| C12N 1/20 | (2006.01) |
| C12N 15/70 | (2006.01) |

(52) U.S. Cl.
CPC ........ *C07K 14/43518* (2013.01); *B29C 48/05* (2019.02); *C12N 1/20* (2013.01); *C12N 15/70* (2013.01); *D01D 1/02* (2013.01); *D01D 5/06* (2013.01); *D01F 4/02* (2013.01); *B29K 2089/00* (2013.01); *B29K 2995/0088* (2013.01); *C07K 2319/21* (2013.01)

(58) Field of Classification Search
CPC .......... C07K 14/43586; C07K 2319/00; C07K 2319/21; C12N 15/70; C12N 15/63; C12N 1/20; D01F 4/00; B29K 2089/00
USPC .................................. 435/348, 69.1, 320.1
See application file for complete search history.

(56) References Cited

U.S. PATENT DOCUMENTS

| | | |
|---|---|---|
| 6,268,169 B1 | 7/2001 | Fahnestock |
| 2003/0013148 A1 | 1/2003 | Evans et al. |
| 2014/0315276 A1 | 10/2014 | Albayrak et al. |

FOREIGN PATENT DOCUMENTS

| | | |
|---|---|---|
| EP | 2518081 B1 | 10/2012 |
| WO | 2013045632 A1 | 4/2013 |
| WO | 2017127940 A1 | 8/2017 |

OTHER PUBLICATIONS

Devos et al., Proteins: Structure, Function and Genetics, 2000, vol. 41: 98-107.*
Whisstock et al., (uarterly Reviews of Biophysics 2003, vol. 36 (3): 307-340.*
Witkowski et al., (Biochemistry 38:11643-11650, 1999.*
Bowen et al., "Recombinant Spidroins Fully Replicate Primary Mechanical Properties of Natural Spider Silk", NASA Technical Reports Server, Jan. 1, 2018, 45 pages.
Evans et al., The Cyclization and Polymerization of Bacterially Expressed Proteins Using Modified Self-splicing Inteins:, The Journal of Biological Chemistry, 1999, vol. 274, No. 26, pp. 18359-18363.
Hauptmann et al., "Native-sized spider silk proteins synthesized in planta via intein-based multimerization", Transgenic Res, 2013, vol. 22, pp. 369-377.

* cited by examiner

*Primary Examiner* — Robert B Mondesi
*Assistant Examiner* — Mohammad Y Meah
(74) *Attorney, Agent, or Firm* — Armstrong Teasdale LLP

(57) ABSTRACT

The present disclosure is directed to systems and methods for synthesizing a spidroin. In some embodiments, the methods comprise synthesizing a monomer in vivo in a heterologous host, the monomer comprising an N-terminus IntC domain and a C-terminus IntN domain, and post-translationally polymerizing the synthesized monomer via in vitro split-intein mediated polymerization.

15 Claims, 37 Drawing Sheets

Specification includes a Sequence Listing.

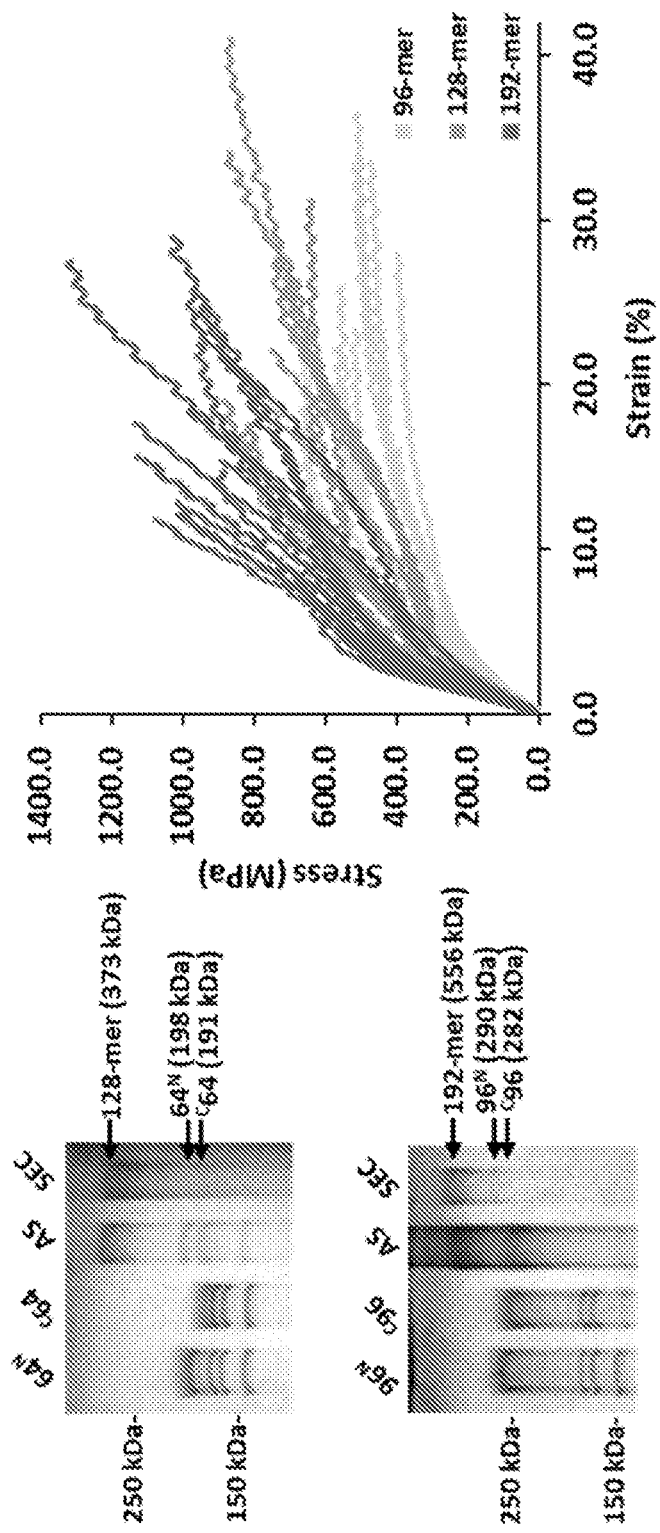

FIG. 15A
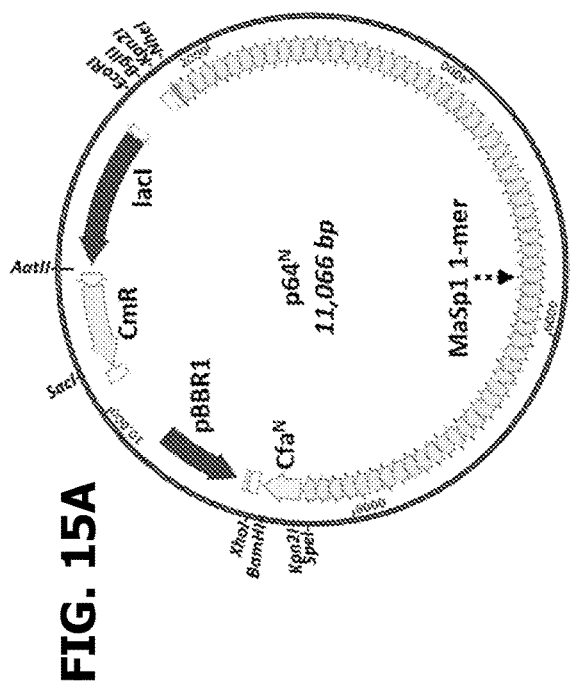
FIG. 15B
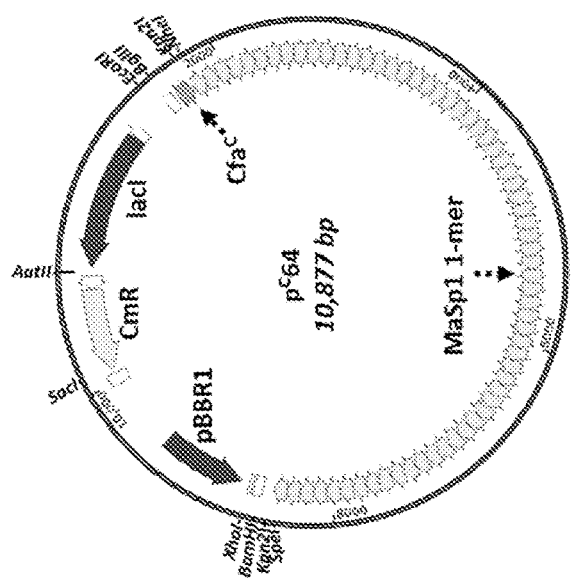
FIG. 15C
FIG. 15D
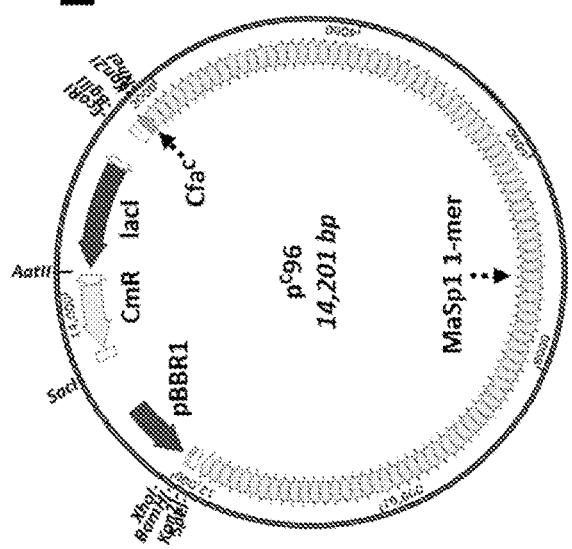

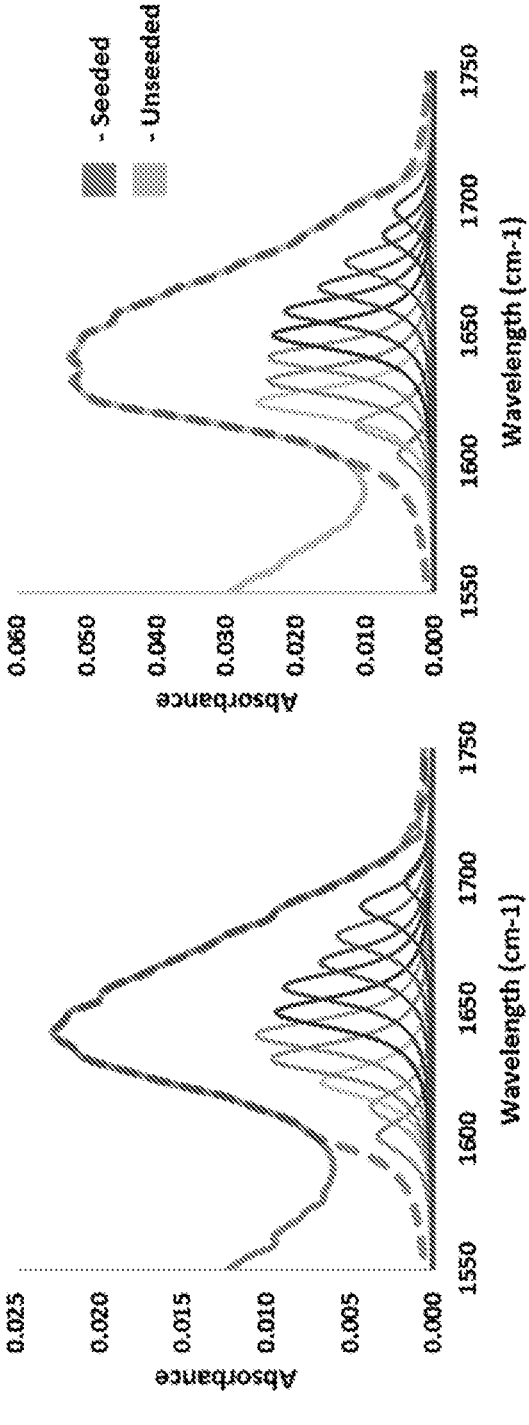
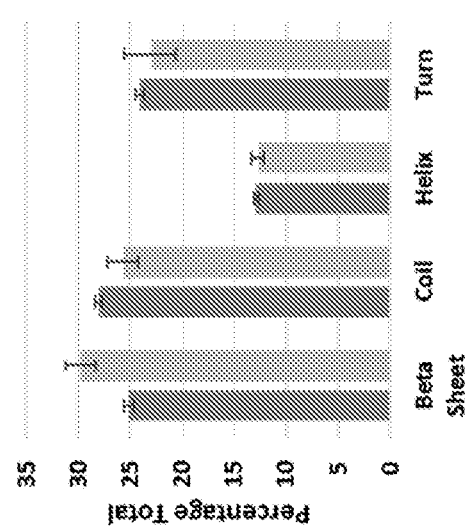
FIG. 25A  FIG. 25B  FIG. 25C  FIG. 25D

SPLIT INTEIN MEDIATED PROTEIN POLYMERIZATION FOR MICROBIAL PRODUCTION OF MATERIALS

CROSS-REFERENCE TO RELATED APPLICATIONS

This application claims priority to U.S. Provisional Application No. 62/779,386, filed Dec. 13, 2018, and to U.S. Provisional Application No. 62/878,525, filed Jul. 25, 2019, the contents of which are incorporated herein by reference in their entireties.

STATEMENT REGARDING FEDERALLY SPONSORED RESEARCH & DEVELOPMENT

This invention was made with government support under FA95501510174 awarded by the Air Force Office of Scientific Research (AFOSR) and NNX15AU45G awarded by the National Aeronautics and Space Administration (NASA). The government has certain rights in the invention.

SEQUENCE LISTING

The instant application contains a Sequence Listing which has been submitted via EFS-Web and is hereby incorporated by reference in its entirety. Said ASCII copy, created on May 7, 2020, is named Sequence_Listing-36254363.TXT and is 11,220 bytes in size.

BACKGROUND OF THE DISCLOSURE

Microbially produced biopolymers are an attractive alternative to traditional petroleum-based polymers due to the use of renewable feedstock, their environmentally friendly production, and their low-energy processing methods. Protein-based materials (PBMs) are an especially appealing form of biopolymer due to their ability to fold into a diversity of precise structures with versatile function and properties. This versatility is evident in the range of biological functions (e.g. structural support, protection, mineralization, predation) and remarkable mechanical properties exhibited by PBMs. Spider silks, for example, can exhibit tensile strength and toughness superior to steel and are used by spiders for prey capture/storage, egg protection, adhesion, and even flight.

Similar to organic polymers, mechanical properties of PBMs are generally dependent on the molecular weight (MW) of constituent proteins, with material strength increasing with MW. In general, higher MW promotes more extensive intermolecular interactions and reduces chain end density, thereby decreasing the probability of chain slippage and fracture and increasing fiber strength. Consequently, high performance PBMs are often composed of high MW (HMW), repetitive proteins (e.g. dragline spider silks >300 kDa). However, microbial synthesis of high MW, highly repetitive PBMs are extremely challenging due to genetic instability caused by recombination of repetitive coding sequences as well as complex mRNA secondary structures. Although several creative strategies have been recently developed to alleviate the problem by extensively optimizing codon usage or balancing the supplies of amino acylated tRNAs via metabolic engineering, microbial synthesis of ultra-high MW material proteins with a few hundred kDa or hundreds of repeats, which are critical for the high performance of silk fibers, suckrin-teeth proteins, and titins, remains seriously limited.

One potential route to bypass the challenges of genetic instability is through post-translational assembly of relatively small, less repetitive protein subunits. In fact, post-translational assemblies are common in natural PBMs. For example, various covalent cross-links occur via protein sidechains during multiscale assembly of collagen, keratin, elastin, and resilin. Even natural spidroins have been found to post-translationally assemble through disulfide linkages between non-repetitive terminal domains. However, these natural post-translational assembly processes are difficult to replicate and exceptionally precisely control for efficient material production in microbial hosts. Alternatively, a handful of biochemical tools are available for precise, site-specific control of post-translational assembly in engineered hosts including SpyTag-SpyCatcher, Sortase A, and split inteins (SIs). Of these approaches, SIs are perhaps the best suited for production of PBMs because they allow for self-cleavage of the catalytic domain from the resulting ligated protein polymer and result in the formation of a backbone peptide bond, therefore providing minimum modification to a PBM's sequence which may otherwise negatively affect material properties.

Accordingly, there is a need for stable production of highly repetitive, high molecular weight spidroins in heterologous hosts. The embodiments described herein resolve at least these known deficiencies.

BRIEF DESCRIPTION OF THE DISCLOSURE

In one aspect, the present disclosure is directed to a method for synthesizing a spidroin. The method comprises synthesizing a monomer in vivo in a heterologous host, the monomer comprising an N-terminus $Int^C$ domain and a C-terminus $Int^N$ domain, and post-translationally polymerizing the synthesized monomer via in vitro split-intein mediated polymerization.

In another aspect, the present disclosure is directed to a method for synthesizing a spidroin. The method comprises synthesizing a seed protein in vivo in a heterologous host, the seed protein comprising a C-terminus $Int^N$ domain, synthesizing a monomer in vivo in the heterologous host, the monomer comprising an N-terminus $Int^C$ domain and a C-terminus $Int^N$ domain, and co-translationally polymerizing the monomer via in vivo split-intein mediated polymerization.

In yet another aspect, the present disclosure is directed to a system for synthesizing a spidroin in vivo. The system comprises a host cell, a seed cassette encoding a seed protein comprising a C-terminus $Int^N$ domain, and a monomer cassette encoding a monomer comprising an N-terminus $Int^C$ domain and a C-terminus $Int^N$ domain.

BRIEF DESCRIPTION OF THE DRAWINGS

The embodiments described herein may be better understood by referring to the following description in conjunction with the accompanying drawings.

FIG. 6A, FIG. 6B, FIG. 6C, FIG. 6D, FIG. 6E, FIG. 6F, and FIG. 6G are exemplary embodiments of high MW spidroin ligation, purification, and mechanical properties of spun fibers in accordance with the present disclosure.

FIG. 15A, FIG. 15B, FIG. 15C, and FIG. 15D are exemplary embodiments of plasmid maps for p64$^N$ (a), p$^C$64 (b), p96$^N$ (c), p$^C$96 (d) in accordance with the present disclosure.

FIG. 21A and FIG. 21B are exemplary embodiments of Ni-Affinity purification of unseeded and seeded polymerization products in accordance with the present disclosure.

FIG. 25A, FIG. 25B, FIG. 25C, and FIG. 25D are exemplary embodiments of secondary structure and morphology of fibers produced by SCP or unseeded method in accordance with the present disclosure.

DETAILED DESCRIPTION OF THE DISCLOSURE

Figure 1:
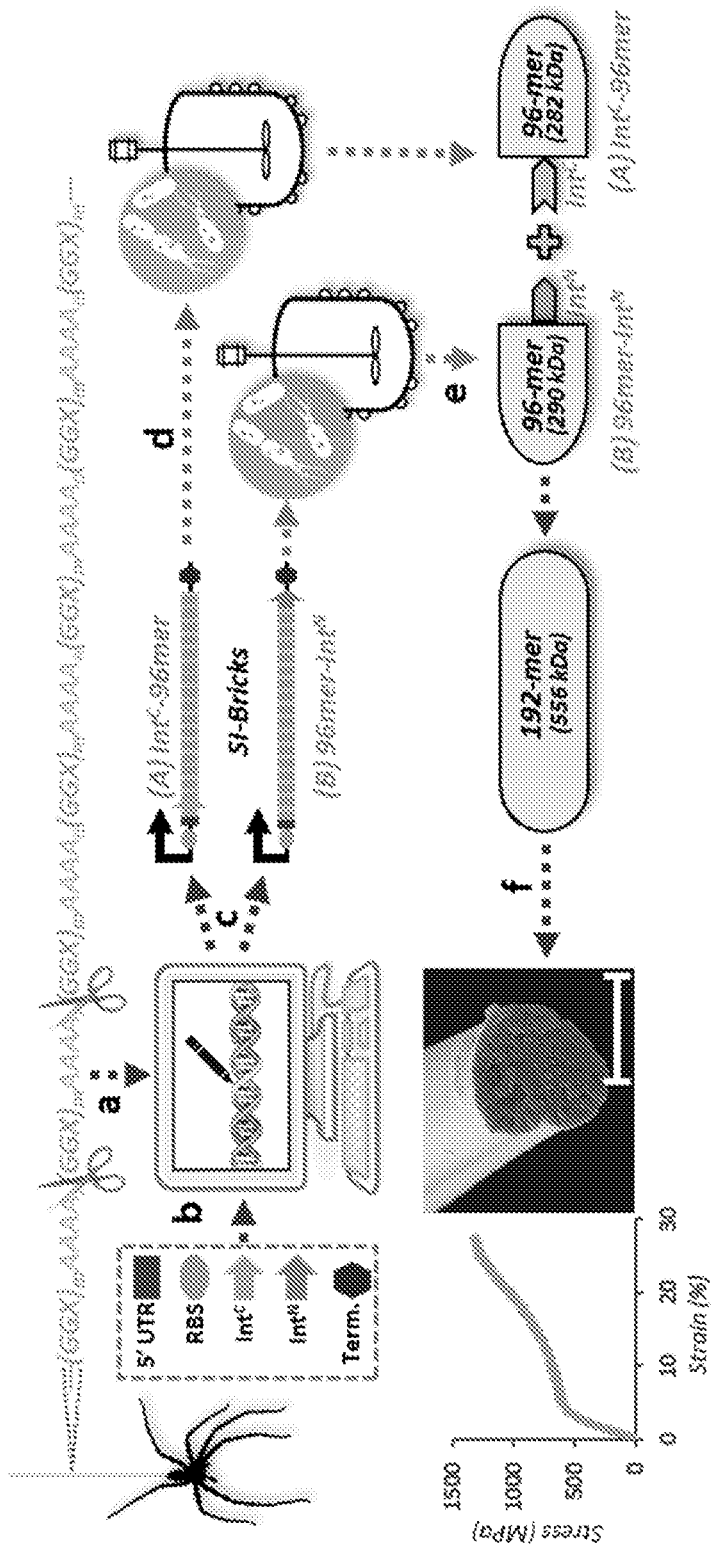
FIG. 1 is an exemplary embodiment of a process schematic for split intein-mediated ligation of spider silk proteins with unprecedented molecular weight and mechanical properties in accordance with the present disclosure.

Microbially Produced Spidroins Replicate Mechanical Properties of Natural Spider Silk Dragline spider silk is among the strongest and toughest bio-based materials, capable of outperforming most synthetic polymers and even some metal alloys. These remarkable properties have resulted in a growing list of potential applications for spider silks that, when coupled with the impracticalities of spider farming, have driven a decades-long effort to produce recombinant spider silk proteins (spidroins) in engineered heterologous hosts. However, these efforts have so far been unable to yield synthetic silk fibers with all the desired mechanical properties of natural spider silk, largely due to an inability to stably produce highly repetitive, high molecular weight (MW) spidroins in heterologous hosts. These challenges are addressed herein with a synthetic biology approach combining standardized DNA part assembly and split intein (SI)-mediated ligation to bioproduce spidroins with unprecedented MW (556 kDa), containing 192 repeat motifs of the *Nephila clavipes* MaSp1 dragline spidroin. Fibers spun from the synthetic spidroins described herein display ultimate tensile strength ($\sigma$), modulus (E), extensibility ($\varepsilon$), and toughness (UT) of 1.03±0.11 GPa, 13.7±3.0 GPa, 18±6%, and 114±51 MJ/m³, respectively. This demonstrates for the first time that microbially produced silk fibers can match the performance of natural *N. clavipes* dragline silk by all common metrics ($\sigma$, E, $\varepsilon$, UT), providing a more dependable source of high performance fibers to replace natural spider silks for a variety of mechanically-demanding applications. Furthermore, the developed platform may be expanded for the assembly and production of other protein-based materials with high MW and repetitive sequences that have so far been challenging to synthesize by genetic means alone.

In some embodiments of the present disclosure, a method for synthesizing a spidroin. The method comprises synthesizing a monomer in vivo in a heterologous host, the monomer comprising an N-terminus Int$^C$ domain and a C-terminus $Int^N$ domain, and post-translationally polymerizing the synthesized monomer via in vitro split-intein mediated polymerization.

In some embodiments the heterologous host is a protein-expressing microbial host and/or the monomer is a silk amino acid sequence from a spider species. In some embodiments, the heterologous host is *E. coli*, and/or the monomer is an *N. clavipes* spidroin. In some embodiments, the synthesized spidroin has a molecular weight of at least about 300 kDa, at least about 400 kDA, at least about 500 kDa, or at least about 600 kDa. In some embodiments the methods further comprise spinning the synthesized spidroin into fibers. In some embodiments, the fibers have a tensile strength of from about 0.5 GPa to about 2.0 GPa, or from about 0.9 GPa to about 1.3 GPa, the fibers have a modulus of about 10 GPa to about 17 GPa, the fibers have an extensibility of from about 5% to about 35%, or from about 10% to about 25% the fibers have a toughness of from about 30 MJ/m$^3$ to about 200 MJ/m$^3$, or from about 60 MJ/m$^3$ to about 170 MJ/m$^3$, and/or the fibers have a β-sheet content of from about 20% to about 60%, or from about 35% to about 45%.

In some embodiments, a method for synthesizing a spidroin comprises: synthesizing silk fragments (called monomers) in heterologous hosts, the monomers comprising either an N-terminus $Int^C$ domain or a C-terminus $Int^N$ domain; and undergoing in vitro split-intein mediated protein ligation reactions, forming a high molecular weight protein containing multiple monomer sequences. In some embodiments, the heterologous host is *E. coli*, or other protein expressing microbial hosts. In some embodiments, the monomers contain a fragment of silk amino acid sequence from *N. clavipes* spidroin or other spider species. In some embodiments, the synthesized spidroin has a molecular weight of at least about 300 kDa. In some embodiments, the method further comprises spinning the synthesized spidroin into fibers. In some embodiments, the fibers have a tensile strength of from about 0.9 GPa to about 1.3 GPa, or at least about 1.0 GPa. In some embodiments, the fibers have an extensibility of from about 10% to about 25%, or at least about 20%. In some embodiments, the fibers have a toughness of from about 60 MJ/m$^3$ to about 170 MJ/m$^3$, or at least about 150 MJ/m$^3$. In some embodiments, the fibers have a β-sheet content of from about 35% to about 45% or at least about 40%.

Spidroins (e.g., dragline spidroins) are typically very large (>300 kDa), highly repetitive proteins, containing hundreds of tandem repeats of glycine- and alanine-rich sequences. As with most polymers, the size of these spidroins is expected to positively correlate with tensile strength due to an increased density of interchain interactions and entanglements and fewer chain-end defects. Indeed, there is a clear correlation between MW and strength for recombinant *N. clavipes* dragline fibers, with the largest spidroin (96-mer, 285 kDa) yielding the strongest recombinant fiber reported to date (σ≈550 MPa). However, despite the apparent need for even larger spidroins to yield fibers with mechanical properties on par with natural silk systems (σ=0.8-1.2 GPa for *N. clavipes* dragline, see Table 1), spidroins larger than 285 kDa have yet to be produced in quantities sufficient for fiber testing due to major challenges in recombinant production of high MW spidroins (e.g. instability of long and highly repetitive DNA/mRNA sequences in heterologous hosts, translation inhibition by complex mRNA secondary structures, a high demand for glycine and alanine tRNAs, and overall metabolic burden).

TABLE 1

Averaged mechanical properties for fibers spun from synthetic spidroins compared to natural *N. clavipes* dragline fibers.

| Spidroin | MW (kDa) | Tensile Strength (MPa)[a] | Young's Modulus (GPa)[a] | Toughness (MJ/m$^3$)[a] | Breaking Strain (%)[a] | Diameter (μm)[a] | Source |
|---|---|---|---|---|---|---|---|
| Synthetic 96-mer | 277 | 525 ± 83 | 7.8 ± 1.3 | 91 + 30 | 23 ± 7 | 6.3 ± 0.7 | Present Study |
| Synthetic 128-mer | 373 | 767 ± 92 | 10.3 ± 1.7 | 115 ± 58 | 22 ± 8 | 6.6 ± 0.9 | Present Study |
| Synthetic 192-mer | 556 | 1031 ± 111 | 133.7 ± 3.0 | 114 ± 51 | 18 ± 6 | 5.7 ± 1.3 | Present study |
| Natural *N. clavipes* Dragline | >300 | 829 ± 334 | 10.3 ± 4.4 | NA | 16.6 ± 5.3 | 4.7 ± 1.3 | Zemlin, 1968[b,10] |
| Natural *N. clavipes* Dragline | >300 | 850 | 12.7 | NA | 20 | 4.2 | Ko, 2001[31] |
| Natural *N. clavipes* Dragline | >300 | 1215 ± 233[c] | 13.8 ± 3.6 | 111.2 ± 30 | 17.2 ± 3.5 | NA | Swanson, 2006[19] |

[a]For all mechanical measurements from the present study, n = 14.
[b]Diameters were converted from originally reported units of denier. Strength and modulus were converted from originally reported units of grams per denier.
[c]"True" stress values rather than the more commonly reported "engineering stress" values. True stress calculates strength based on the final diameter of the fiber assuming constant volume deformation, thus true stress values are expected to be significantly higher than engineering stress values as calculated in the present study.
NA: values not found in the referenced study.

To confront these long-standing challenges, using split intein (SI)-mediated reactions was envisioned to post-translationally ligate the largest spidroins that can be stably expressed in engineered *Escherichia coli*, i.e. 96-mer (FIG. 1).

FIG. 1 shows a process schematic for split intein-mediated ligation of spider silk proteins with unprecedented molecular weight and mechanical properties. In step (a) the highly repetitive core of natural *N. clavipes* dragline silk protein MaSp1 (shown as a simplified consensus peptide sequence) was reduced to a single repeat unit (1-mer). In step (b) the 1-mer DNA sequence was combined in silico with 5' UTR, RBS, split intein (SI), and terminator sequences, which were then computationally optimized for microbial production. In step (c) the optimized DNA sequences were assembled within the framework of a standardized DNA part assembly system termed SI-Bricks to yield complementary $Int^C$- or $Int^N$-fused 96-mer constructs. In step (d) constructs were transformed to *E. coli* for bioproduction. In step (e) cell cultures were mixed and lysed to initiate SI-mediated covalent ligation of 96-mer spidroins to yield a 192-mer, 556 kDa product. In step (f) the ligated product was purified and spun into fibers for mechanical testing. Scale bar indicates 5 μm.

SIs are peptide auto processing domains that, when fused to separately expressed proteins, catalyze spontaneous splicing reactions, covalently linking their fusion partners via a peptide bond and leaving only a few residues (6 amino acids) at the ligation site. These few residues are unlikely to affect the properties of the much larger ligated spidroins (6720 amino acids total). Given the tendency of high MW spidroins to form inclusion bodies in microbial hosts, a recently engineered SI pair (Cfa) was employed that retains catalytic activity in the presence of 8 M urea, a denaturant often used to extract and solubilize spidroins from *E. coli*. Thus, ligating an N-intein ($Int^N$)-fused 96-mer spidroin ($96^N$) with a C-intein ($Int^C$)-fused 96-mer ($^C96$) would yield a 556 kDa, 192-mer spidroin (FIG. 1 at step e).

To facilitate microbial production of highly repetitive, SI-fused material proteins, a standardized DNA part assembly system termed SI-Bricks was developed, as described herein below (see also FIG. 2).

Figure 2:
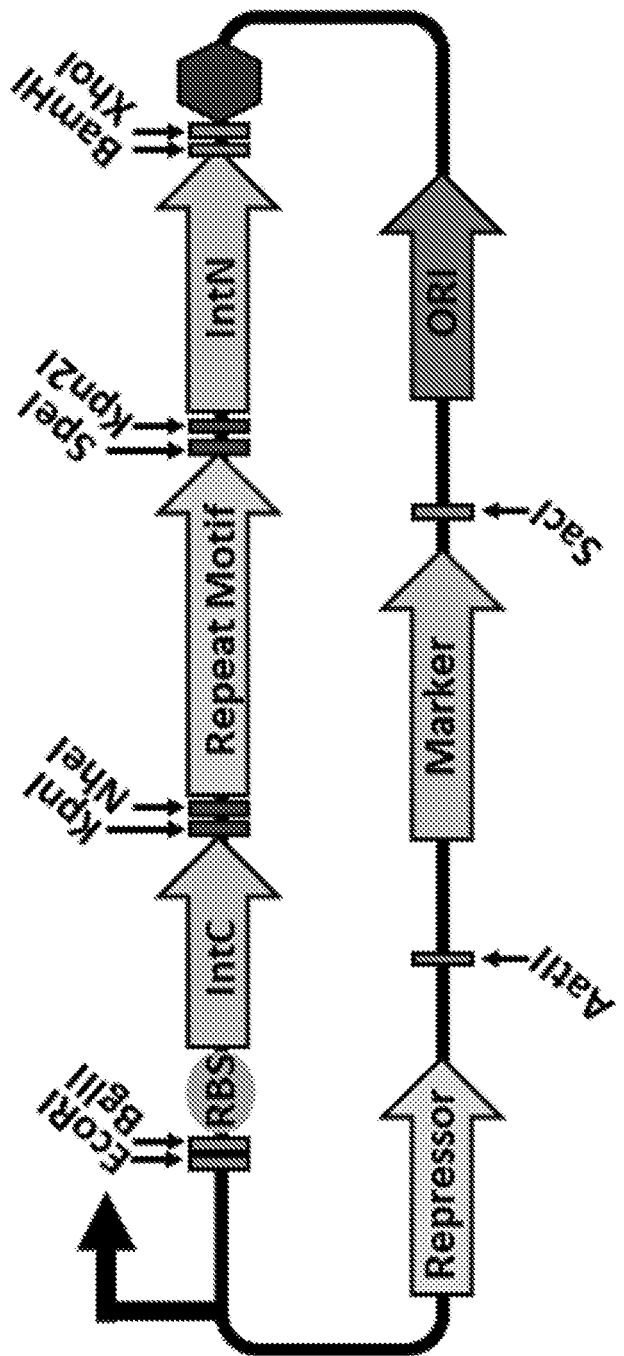
FIG. 2 is an exemplary embodiment of an SI-Bricks assembly system in accordance with the present disclosure.
Figure 3:
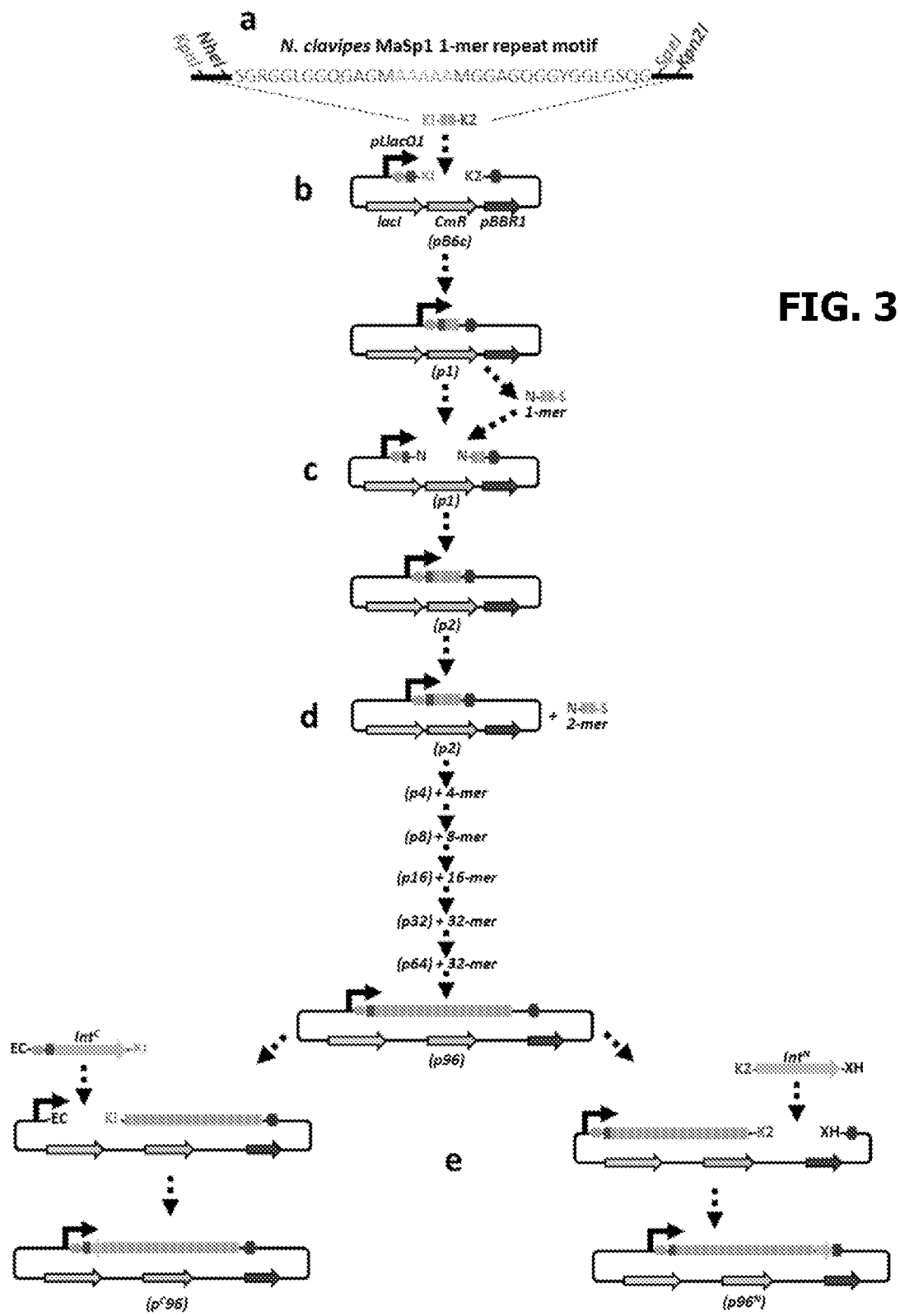
FIG. 3 is an exemplary embodiment of a schematic of recursive directional genetic assembly of plasmids in accordance with the present disclosure.

FIG. 2 shows the SI-Bricks assembly system. The SI-Bricks assembly system allows for recursive directional genetic assembly of repeat motifs through NheI/SpeI digestion and enzymatic ligation (FIG. 3). Assembled repeat motif parts can be swapped with KpnI/Kpn2I digestion/ligation, $Int^C$ parts (including 5' UTR, RBS, and start codon) with EcoRI/KpnI, $Int^N$ parts with Kpn2I/XhoI, promoters with EcoRI/AatII, antibiotic selection markers with AatII/SacI, and replication origins with SacI/XhoI. If desired, any combination of parts can be assembled simultaneously in a one-pot ligation.

Design of SI-Bricks standardized DNA part assembly system. SI-Bricks is meant to facilitate design and microbial production of SI-fused material proteins. SI-Bricks were developed based on five principle design considerations. (1) The system allows for in situ (i.e. within the final expression vector/host) recursive directional genetic assembly of material protein repeat motifs up to the maximum genetically-permissible size (e.g. 96-mer for MaSp1 described herein). (2) The system allows for selective swapping of the three SI-Bricks parts necessary for post-translational, SI-mediated ligation: (a) 5' UTR/RBS/$Int^C$, (b) multimeric material protein, (c) $Int^N$/3' UTR. (3) No restriction sites within the coding sequence should introduce amino acids likely to be detrimental to SI ligation or final material properties. (4) For maximum convenience, the system allows simultaneous "one-pot" assembly of all three protein parts. (5) The system also allows for selective swapping of the promoter, antibiotic marker, and replication origin.

SI-Bricks is based on existing BglBricks vectors which have been extensively used to construct multi-enzyme metabolic pathways for metabolic engineering. BglBricks vectors employ compatible "sticky end" restriction sites BglII/BamHI for recursive directional genetic assembly. However, this enzyme pair is not ideal for use with SI-fused multimeric proteins as the BglII site would introduce an arginine residue between $Int^C$ and the multimeric material protein. This bulky, positively charged residue would be proximal to the folded SI active site, which may negatively affect SI ligation—violating the design criterium (3). To solve this problem, it was chosen to flank material protein repeat sequences with an alternative pair of compatible sticky end restriction sites, NheI and SpeI, for recursive assembly. NheI and SpeI code amino acids alanine-serine and threonine-serine, respectively, which are less likely to affect SI ligation. During repetitive silk assembly, the cohesive end "scar" sequence from NheI/SpeI ligation is ACTAGC, encoding a threonine-serine linker that is not detrimental to silk properties. Finally, because NheI/SpeI have compatible sticky ends, flanking material proteins with NheI/SpeI alone would not allow for single-pot assembly of all parts, failing to meet design criterium (4). Thus, it was further chosen to flank multimeric material protein parts with an additional pair of orthogonal restriction sites, KpnI and Kpn2I.

FIG. 3 shows a schematic of recursive directional genetic assembly of plasmids. (a) The sequence for a single representative repeat unit (1-mer) of the *N. clavipes* dragline silk MaSp1 protein was flanked by restriction sites KpnI (K1), NheI (N), SpeI (S), and Kpn2I (K2). (b) The sequence was ligated between sites KpnI and Kpn2I on the modified BglBricks vector pB6c with IPTG-inducible promoter pLlacO1, replication origin pBBR1, and chloramphenicol resistance ($Cm^R$). (c) The resulting 1-mer plasmid (p1) was linearized by digestion with NheI. The linearized vector was ligated with a separate 1-mer insert with NheI/SpeI sticky ends to yield p2. (d) After screening for correctly oriented inserts, the process was repeated, each time with a two-fold larger insert until p64 was obtained. Plasmid p96 was then obtained by inserting NheI/SpeI digested 32-mer into linearized p64. (e) Optimized SI sequence $Cfa^C$ ($Int^C$) was inserted 5' of the 96-mer sequence in p96 by EcoRI(EC)/KpnI digestion/ligation to yield $p^C96$. Optimized SI sequence $Cfa^N$ ($Int^N$) was inserted 3' of the 96-mer sequence in p96 by Kpn2I/XhoI(XH) digestion/ligation to yield $p96^N$.

Thus, with SI-Bricks, material protein repeat motifs can be iteratively assembled in situ through digestion and enzymatic ligation using NheI and SpeI (FIG. 3). When needed, the resulting multimeric material protein sequences can be swapped with other material proteins by KpnI/Kpn2I digestion/ligation. The 5' UTR/RBS/$Int^C$ sequences can be swapped with other $Int^C$/N-terminal sequences by EcoRI/KpnI digestion/ligation. The $Int^N$/3'UTR sequences can be swapped with other $Int^N$/C-terminal sequences by Kpn2I/XhoI digestion/ligation. As per the existing BglBricks standard, a large library of promoter parts can be swapped by AatII/EcoRI digestion/ligation, antibiotic markers can be swapped by AatII/SacI digestion/ligation, and replication origins can be swapped by SacI/XhoI digestion/ligation. Additionally, when needed, other proteins can be cloned into the same operon as multimeric material proteins to be translated separately from a common mRNA transcript. For example, in some embodiments a fluorescent reporter protein can be introduced for monitoring purposes. This can be accomplished by digesting the expression vector with either EcoRI/BglII or BamHI/XhoI and inserting the desired protein digested by EcoRI/BamHI or BglII/XhoI, respectively.

SI-Bricks allows for rapid genetic swapping of the core components of the envisioned SI-mediated ligation system (i.e. N-inteins, material proteins, C-inteins, and fusion domains/purification tags) in addition to common standardized biological parts (e.g. promoters, ribosomal binding sites, replication origins, and selection markers), all through simple restriction enzyme digestion and enzymatic ligation. To construct the SI-Bricks parts necessary, 64-mer and 96-mer spidroin DNA sequences were first assembled by recursive directional genetic assembly of a single codon-optimized repeat unit (1-mer) of the N. clavipes dragline spidroin MaSp1. The assembled spidroin sequences, flanked by SI-Bricks restriction sites, were genetically combined with codon-optimized SI DNA sequences and other necessary expression parts (FIG. 3). The resulting SI-fused spidroins ($64^N$, $^C64$, $96^N$, and $^C96$) were individually expressed in an E coil host with $^{glycyl}$tRNA levels engineered to meet the demands of the most frequently used glycine codons in the spidroin sequences. Using optimized fermentation conditions, typical titers of the SI-fused spidroins were approximately 2 g/L from a glucose minimal medium with tryptone supplementation after four hours of production (FIGS. 4A-4B).

Figures 4A, 4B:
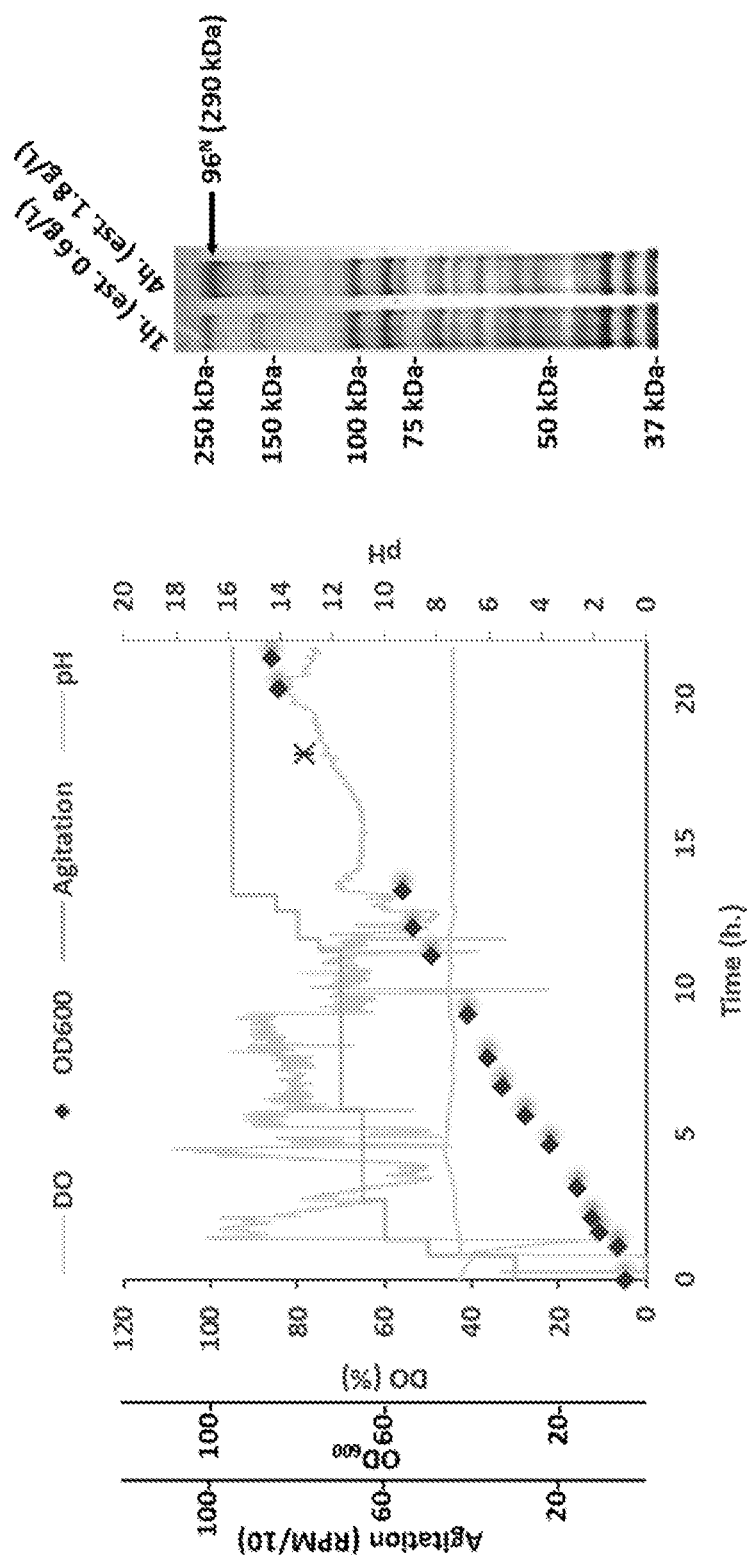
FIG. 4A and FIG. 4B are exemplary embodiments of bioproduction of spidroins in fed-batch bioreactor in accordance with the present disclosure.

FIG. 4A and FIG. 4B show bioproduction of spidroins in fed-batch bioreactor. FIG. 4A shows dissolved oxygen (DO), cell density ($OD_{600}$), bioreactor agitation rate, and pH over the course of fermentation. Time 0 represents the start of fermentation in the bioreactor. The red asterisk indicates the point of induction with 1 mM IPTG. FIG. 4B shows representative SDS-PAGE of spidroin-producing cells ($96^N$) at 1 h and 4 h post induction. Estimated titers of $96^N$ are indicated above each lane. Titers were estimated based on densitometric analysis of the SDS-PAGE gel as described in Methods. Separating gel contained 8% acrylamide.

Spidroin inter- and intramolecular interactions can be highly sensitive to salt and pH, even in the presence of 8 M urea. It was expected that unwanted spidroin interactions would lower SI ligation efficiency. Thus, to test optimum conditions for the ligation of SI-fused spidroins, 8 M urea extracts of E. coli expressing $64^N$ or $^C64$ were mixed at several salt concentrations, temperatures, and pH values (FIGS. 5A-C).

Figure 5A:
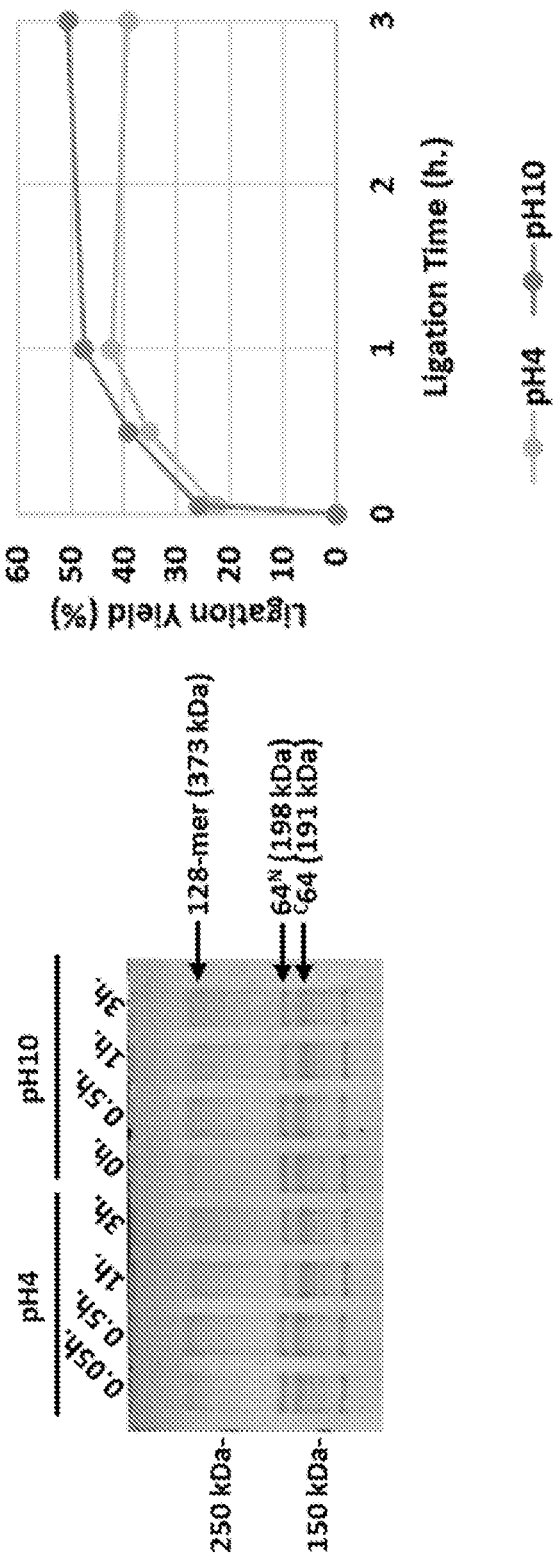
FIG. 5A, FIG. 5B, and FIG. 5C are exemplary embodiments of kinetics of SI-catalyzed ligation of spidroins in accordance with the present disclosure.
Figure 5B:
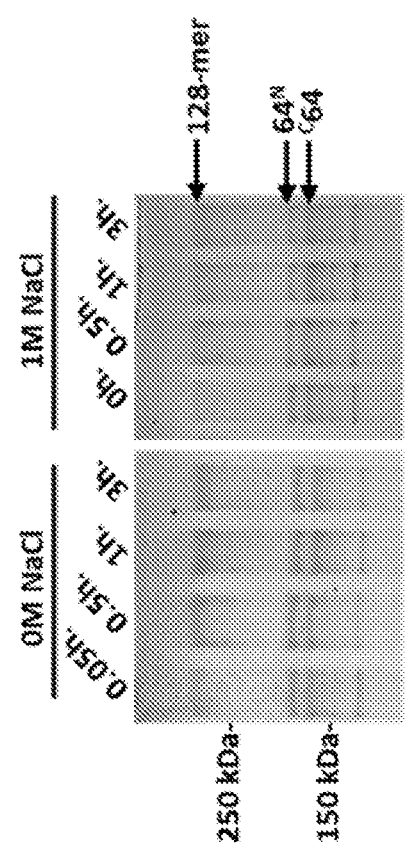
Figure 5B:
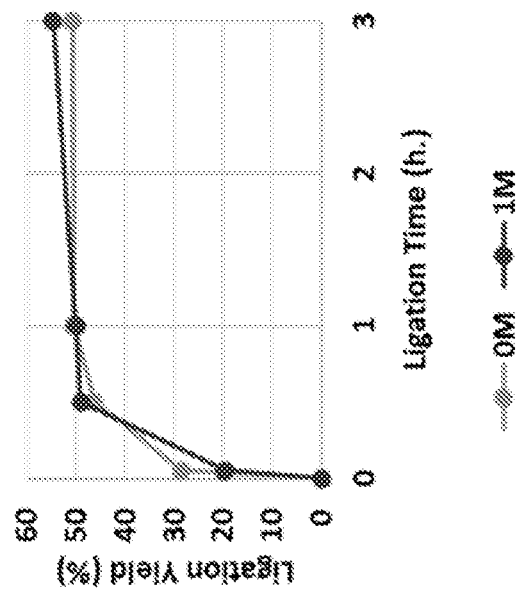
Figure 5C:
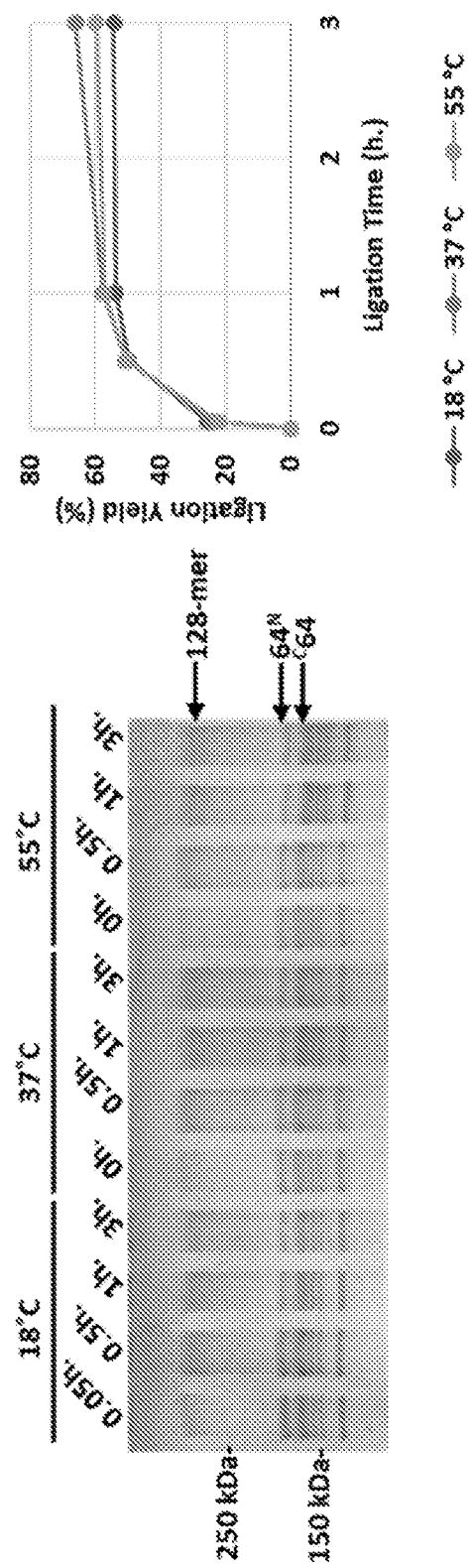

FIGS. 5A-5C show kinetics of SI-catalyzed ligation of spidroins. SDS-PAGE (left) of reaction mixtures containing 1:1 ratio of $64^N$ and $^C64$ in 8 M urea, 2 mM TCEP at (FIG. 5A) different pH (pH4=300 mM NaCl, 10 mM ammonium acetate, pH 4; pH10=300 mM NaCl, 10 mM ammonium bicarbonate, pH 10); (FIG. 5B) different salt concentration (0M=0 M NaCl, 10 mM MOPS pH 7.4; 1M=1 M NaCl, 10 mM MOPS pH 7.4); and (FIG. 5C) different temperature (18° C.; 37° C.; 55° C.) in 300 mM NaCl, 10 mM MOPS, pH 7.4. Black arrows indicate the expected size of product and reactant bands. Ligation yields (right) were calculated as the integrated intensity of the product band over the sum of both reactant and product bands. Note, spidroins used in this experiment were produced from shake flasks, which produce lower final titers than those from fed-batch bioreactors. Separating gels contained 6% acrylamide.

Under all tested conditions, SI-mediated spidroin ligation was both rapid and robust, with the highest ligation yields observed at 37° C., 300 mM NaCl, pH 7. Thus, for all subsequent ligations, these conditions were maintained, giving ligation yields of 68% and 62% for 128-mer and 192-mer spidroins, respectively (FIG. 6A and FIG. 6B).

FIGS. 6A-6F show high MW spidroin ligation, purification, and mechanical properties of spun fibers. Coomassie Blue-stained SDS-PAGE gels for (FIG. 6A) $64^N$+$^C64$ ligation and (FIG. 6B) $96^N$+$^C96$ ligation. Lane 1, whole cells expressing N-intein fused spidroins ($64^N$ or $96^N$); lane 2, whole cells expressing C-intein fused spidroins ($^C64$ or $^C96$); lane 3, ligation products after selective ammonium sulfate precipitation; lane 4, products after SEC purification. Separating gels contained 8% acrylamide. (FIG. 6C) Compiled stress-strain curves for all fibers tested. (FIG. 6D) Ultimate tensile strength, (FIG. 6E) elastic modulus, (FIG. 6F) breaking strain, and (FIG. 6G) toughness of 96-mer, 128-mer, and 192-mer fibers. Error bars represent standard deviations, n=14. * P<0.0001, two-tailed unpaired t-test.

Figures 7A, 7B, 7C:
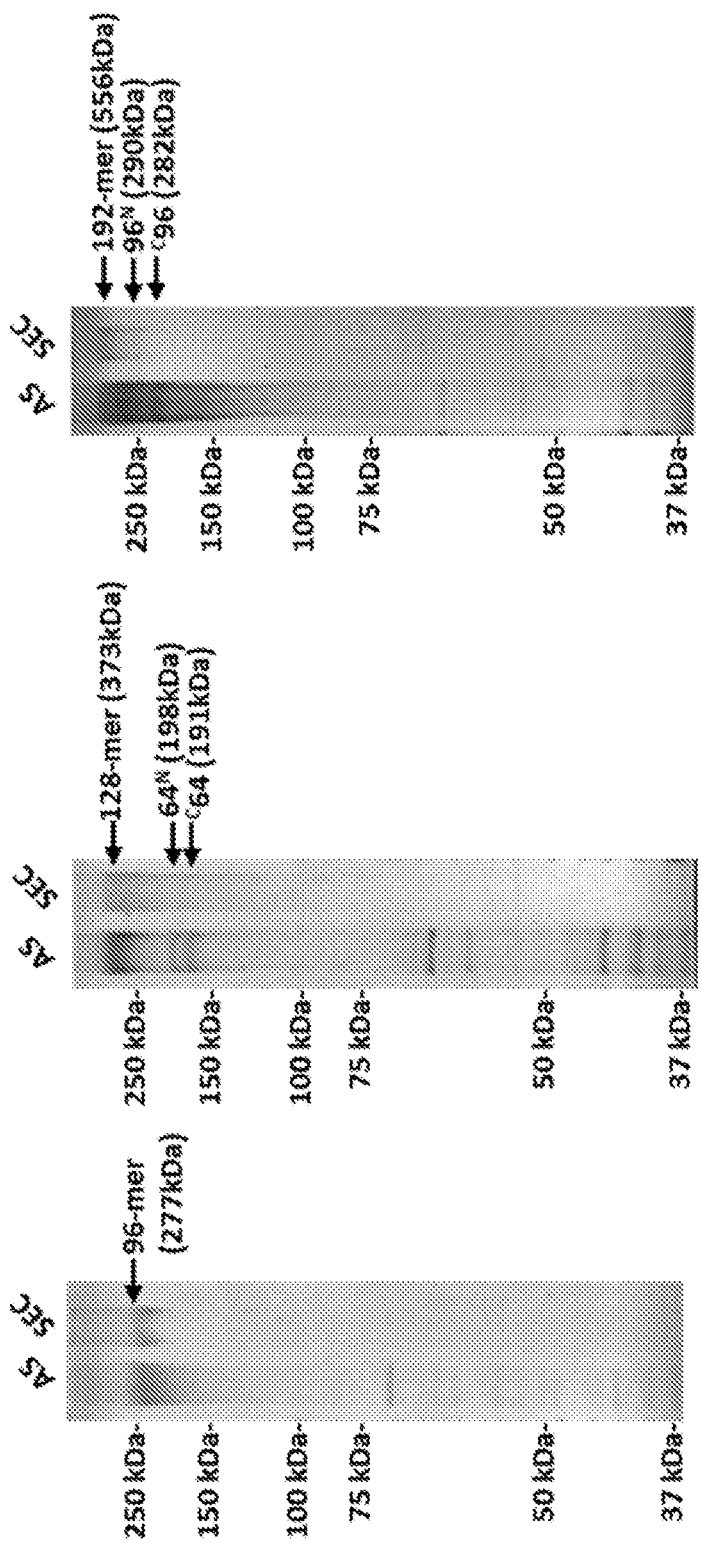
FIG. 7A, FIG. 7B, and FIG. 7C are exemplary embodiments of purification of 96-, 128-, and 192-mer spidroins in accordance with the present disclosure.

Ligation products were initially separated from most cellular proteins by selective ammonium sulfate precipitation and then further separated from unreacted 64-mer or 96-mer by size exclusion chromatography (SEC) for a final product purity≥90% (FIGS. 7A-7C).

FIGS. 7A-7C show purification of 96-, 128-, and 192-mer spidroins. Coomassie Blue-stained SDS-PAGE gels for purification of (FIG. 7A) 96-mer, (FIG. 7B) 128-mer, (FIG. 7C) 192-mer. Lane 1, products after selective precipitation with ammonium sulfate (AS). Lane 2, products after SEC purification. Separating gels contained 8% acrylamide.

As a standard for mechanical properties, a 96-mer spidroin with no SIs was also expressed and purified following identical procedures. Spinning dope was prepared from lyophilized powder of each purified protein and fibers were spun and mechanically tested following well-documented wet-spinning protocols detailed in Methods.

Figures 6D, 6E, 6F, 6G:
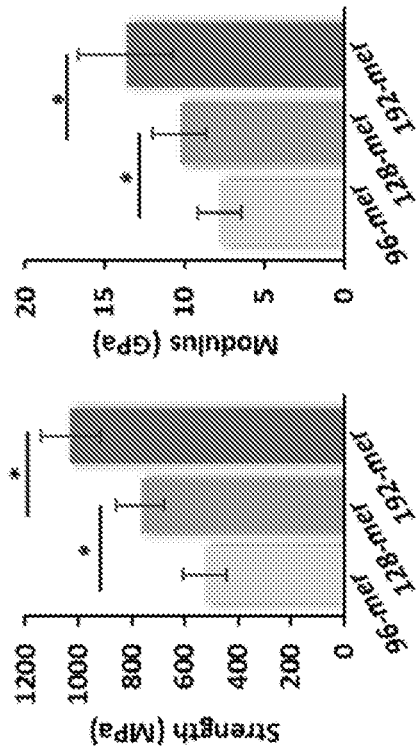

Comparing post-drawn 96-mer and 192-mer fibers, mechanical testing revealed significant, nearly two-fold increases in both tensile strength (from 525 to 1031 MPa, P<0.0001, two-tailed unpaired t-test, n=14) and modulus (from 7.8 to 13.7 GPa, P<0.0001, two-tailed unpaired t-test, n=14) (FIG. 6D and FIG. 6E). Average toughness also increased slightly (25%, P=0.1452, two-tailed unpaired t-test, n=14), while average breaking strain decreased slightly (22%, P=0.0546, two-tailed unpaired t-test, n=14), though neither change was statistically significant due in part to large fiber-to-fiber variations (FIG. 6F and FIG. 6G). For both strength and modulus, 128-mer fibers showed performance intermediate to 96- and 192-mer fibers. Together, these results suggest the persistence of a positive correlation between spidroin size and fiber strength and modulus up to a spidroin MW of at least 556 kDa. Most significantly, these results demonstrate that fibers spun from microbially synthesized 192-mer N. clavipes dragline spidroin as described herein fully replicate the primary desired mechanical properties of natural N. clavipes dragline silk (i.e. σ≈1 GPa, E≈12 GPa, $U_T$≈100 MJ/m$^3$, ε≈18%, Table 1).

To gain insight into the origins of the exceptional strength and toughness of 192-mer fibers, fiber physical characteristics were examined at both micro and molecular scales. At the micro scale, light microscopy images confirmed that fibers had consistent diameters along the fiber axes and that diameters did not vary significantly with MW (P=0.055, one-way ANOVA, Table 1, FIG. 8).

Figure 8:
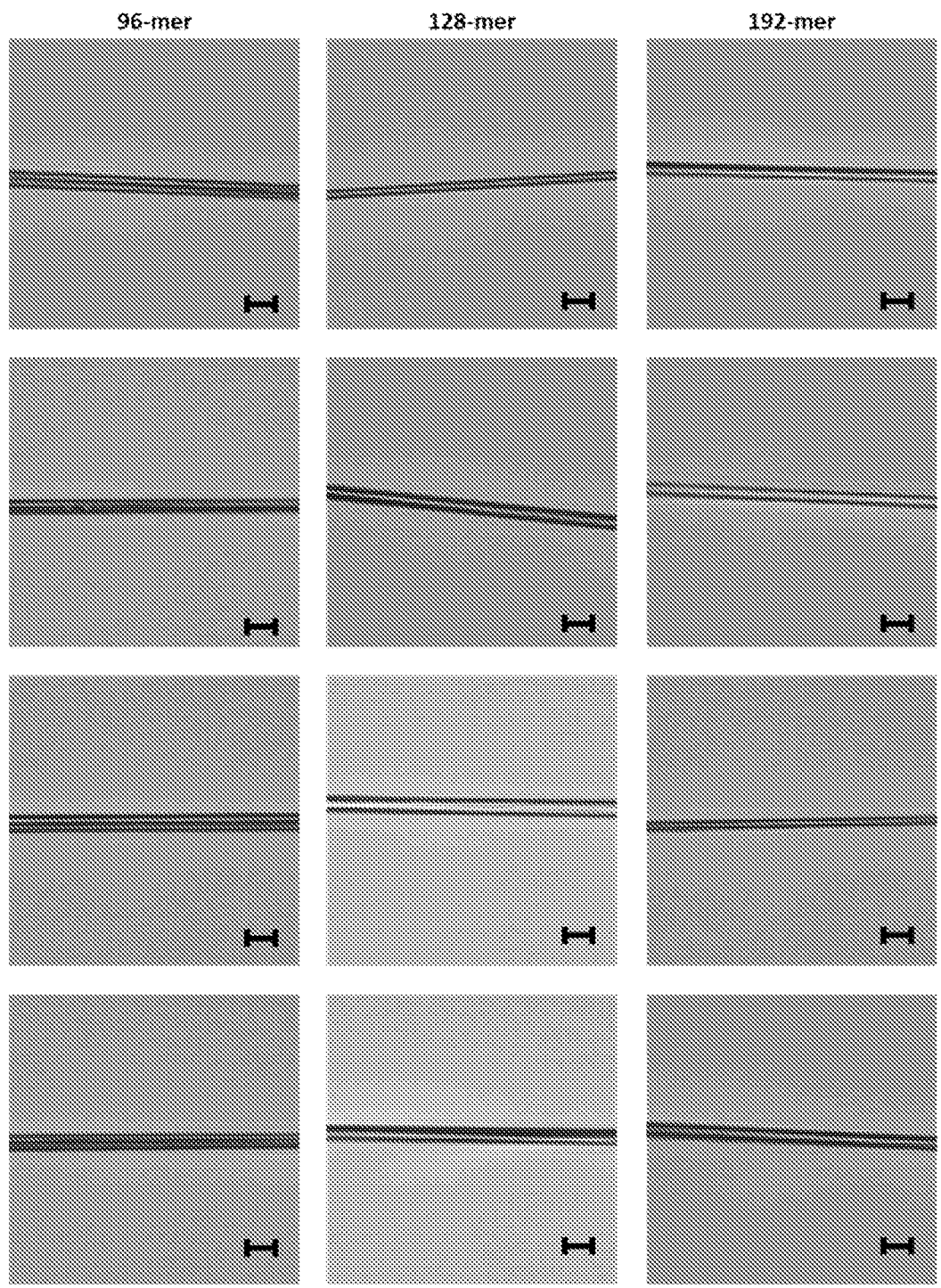
FIG. 8 is an exemplary embodiment of light microscopy of spun spidroin fibers in accordance with the present disclosure.
Figure 9A:
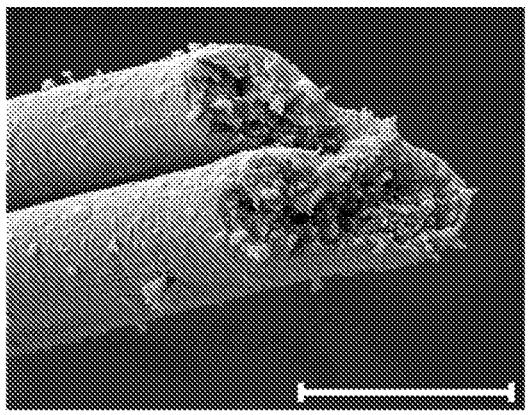
FIG. 9A, FIG. 9B, FIG. 9C, FIG. 9D, FIG. 9E, and FIG. 9F are exemplary embodiments of representative SEM micrographs of 96-mer fibers in accordance with the present disclosure.
Figure 9B:
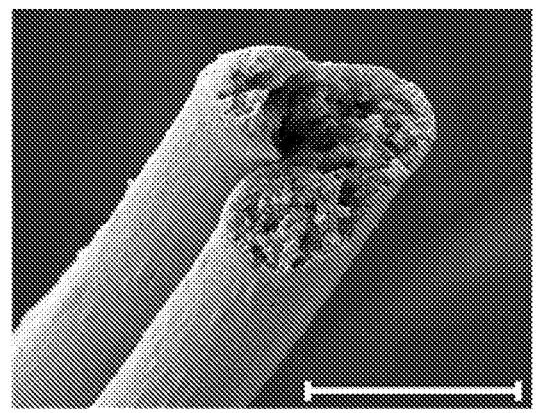
Figure 9C:
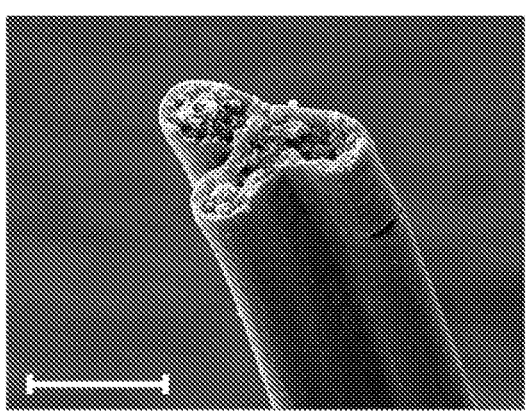
Figure 9D:
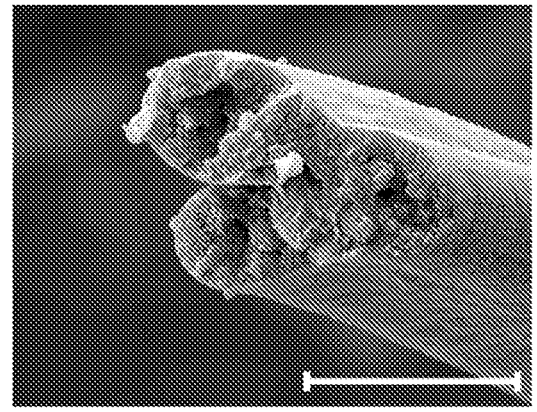
Figure 9E:
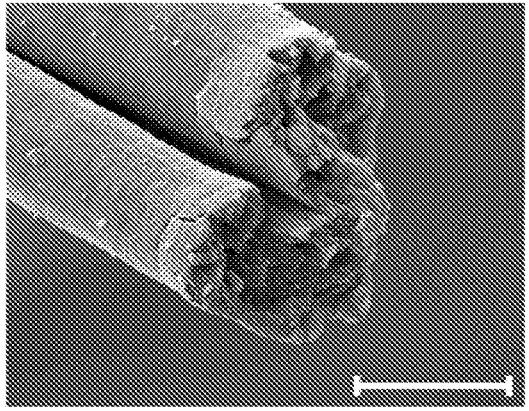
Figure 9F:
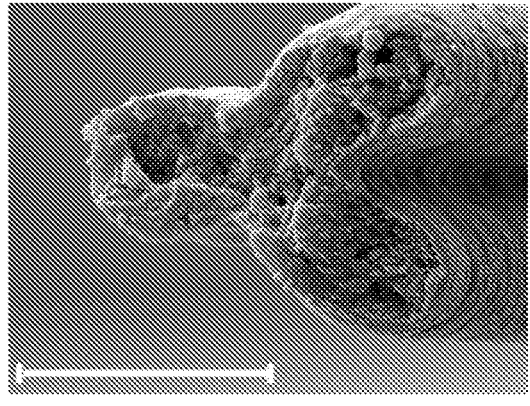
Figure 10A:
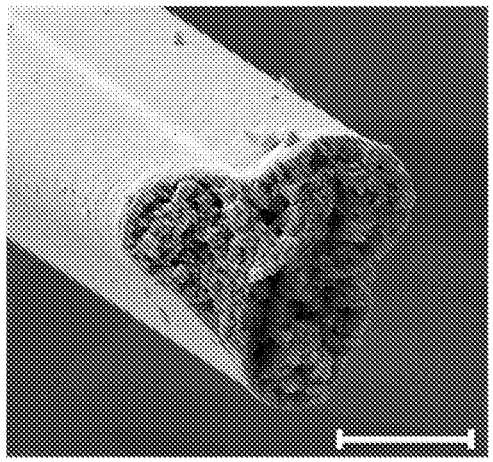
FIG. 10A, FIG. 10B, FIG. 10C, FIG. 10D, FIG. 10E, and FIG. 10F are exemplary embodiments of representative SEM micrographs of 128-mer fibers in accordance with the present disclosure.
Figure 10B:
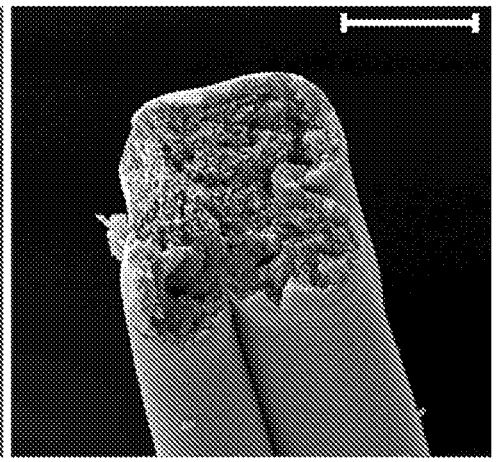
Figure 10C:
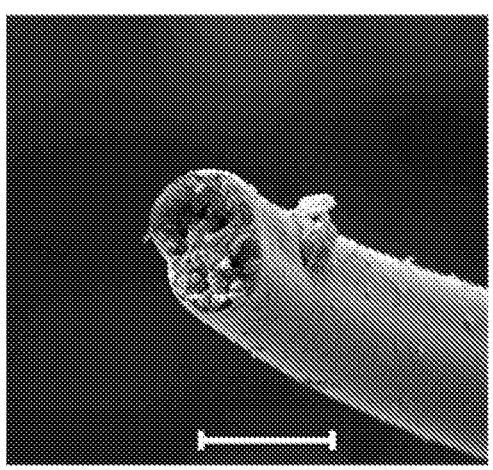
Figure 10D:
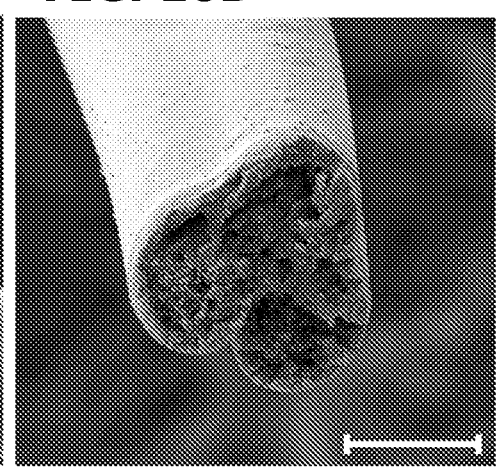
Figure 10E:
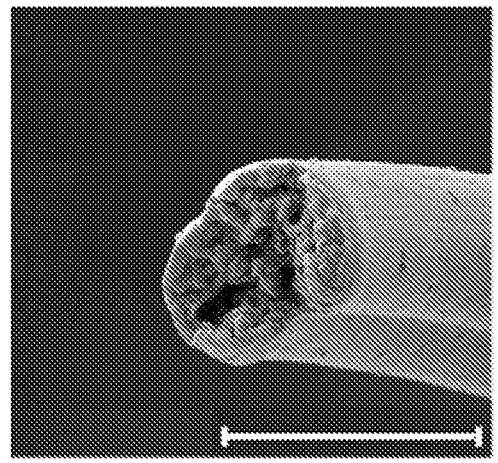
Figure 10F:
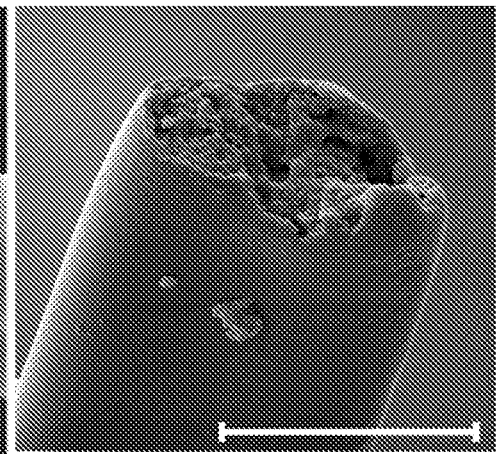
Figure 11A:
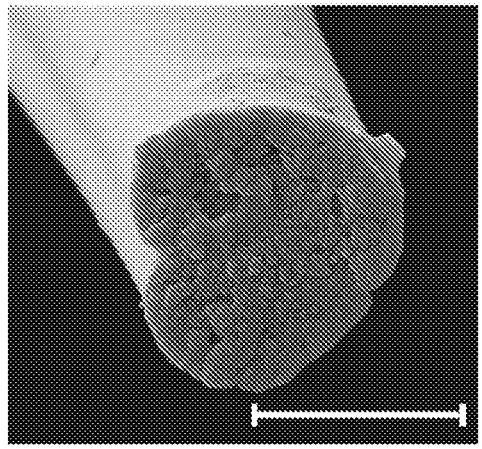
FIG. 11A, FIG. 11B, FIG. 11C, FIG. 11D, FIG. 11E, and FIG. 11F are exemplary embodiments of representative SEM micrographs of 192-mer fibers in accordance with the present disclosure.
Figure 11B:
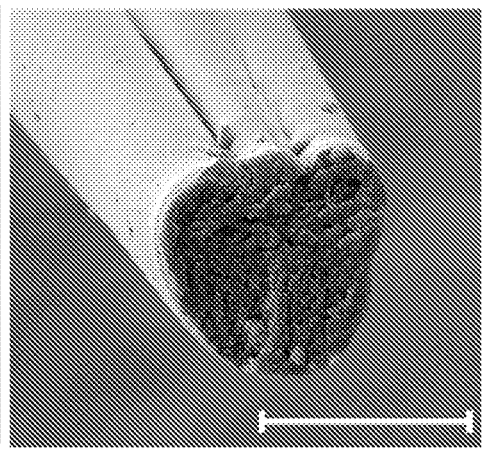
Figure 11C:
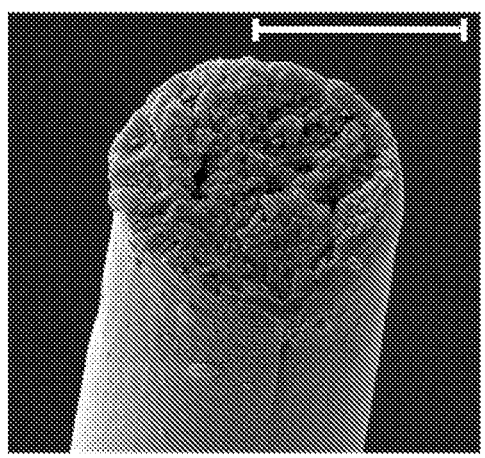
Figure 11D:
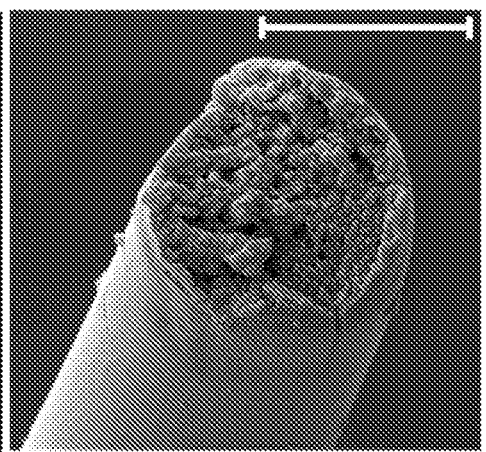
Figure 11E:
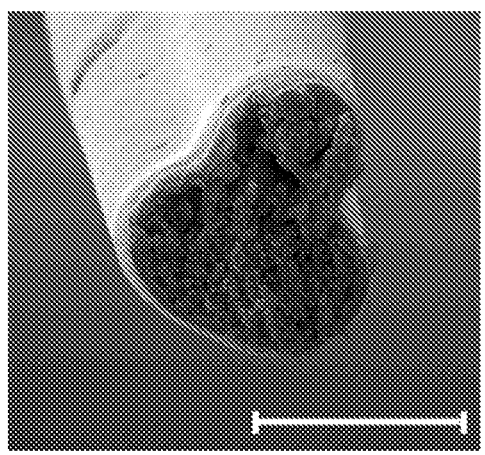
Figure 11F:
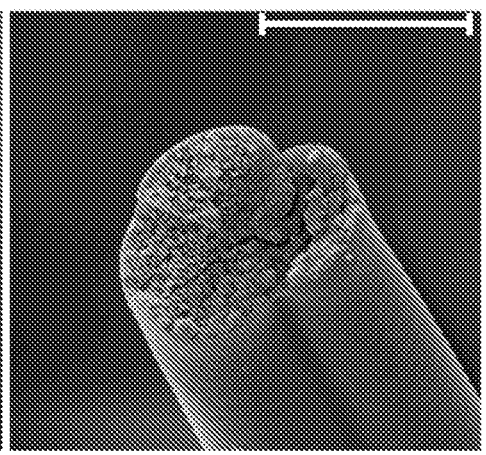

FIG. 8 shows light microscopy of spun spidroin fibers. Representative images of spidroin fibers were recorded using a Nikon Eclipse TiE Inverted Microscope and a 60× objective. Scale bar is 5 µm.

Fiber diameters were also similar to those of natural dragline fibers, which have been reported to range from 1-8 µm (FIG. 8). Meanwhile, scanning electron microscopy (SEM) micrographs showed a distinct trend of decreasing fiber surface roughness and fewer interior defects with increasing MW (FIGS. 9A-9F, FIGS. 10A-10F, and FIGS. 11A-11F).

FIGS. 9A-9F show representative SEM micrographs of 96-mer fibers. All samples were imaged after tensile tests. All scale bars are 5 µm. FIGS. 10A-10F show representative SEM micrographs of 128-mer fibers. All samples were imaged after tensile tests. All scale bars are 5 µm. FIGS. 11A-11F show representative SEM micrographs of 192-mer fibers. All samples were imaged after tensile tests. All scale bars are 5 µm.

Figure 12B:
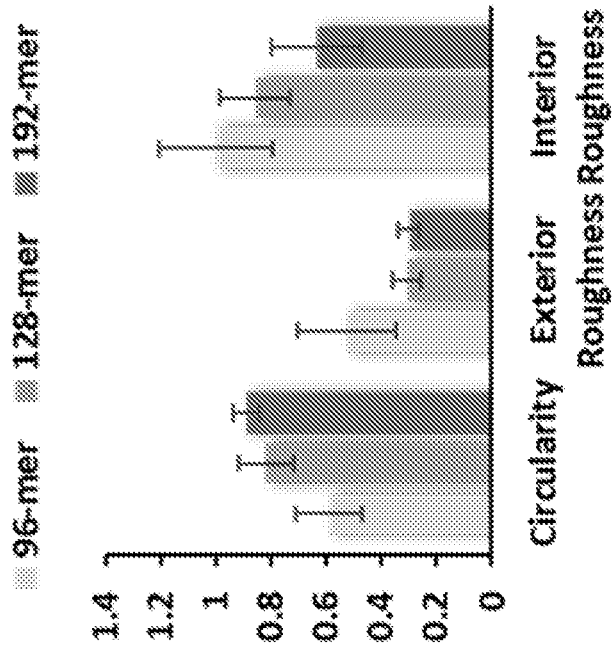
FIG. 12A, FIG. 12B, FIG. 12C, and FIG. 12D are exemplary embodiments of fiber characteristics at micro and molecular scales in accordance with the present disclosure.

To quantify this trend, the surface roughness of fiber exteriors and interiors was estimated using greyscale pixel values from six micrographs for each spidroin MW (FIG. 12B; Table 2). The mean exterior and interior surface roughness values decreased 42% and 36%, respectively, between 96-mer and 192-mer fibers. Meanwhile, a trend of increased circularity with increasing MW was also apparent from the SEM micrographs, with 96-mer fibers exhibiting variations of a folded/lobed morphology and 192-mer fibers exhibiting a mostly compact, nearly circular morphology. The average circularity values for 192- and 96-mer fibers were 0.89 (±0.05) and 0.59 (±0.12), respectively, where a value of 1 indicates a perfect circle (see Methods for calculation) (FIG. 12B; Table 2).

Figure 12A:
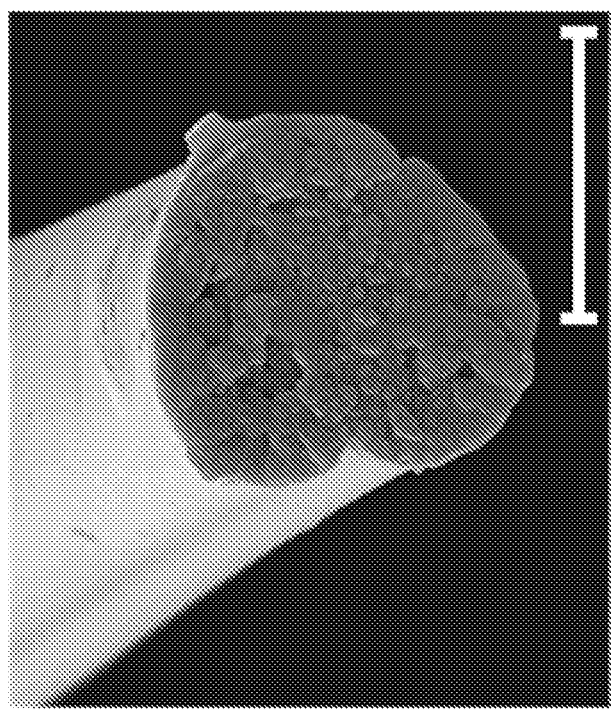
Figure 12C:
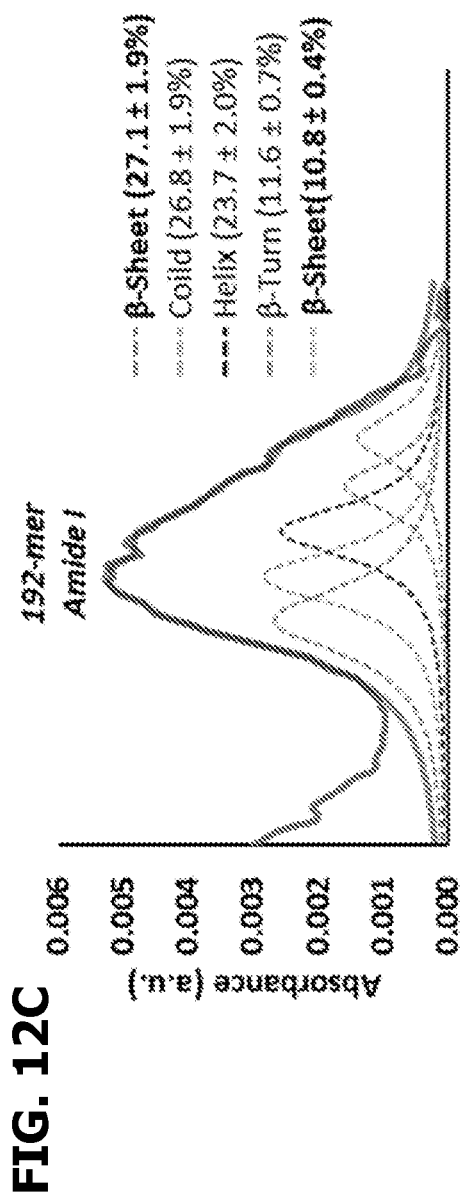
Figure 12D:
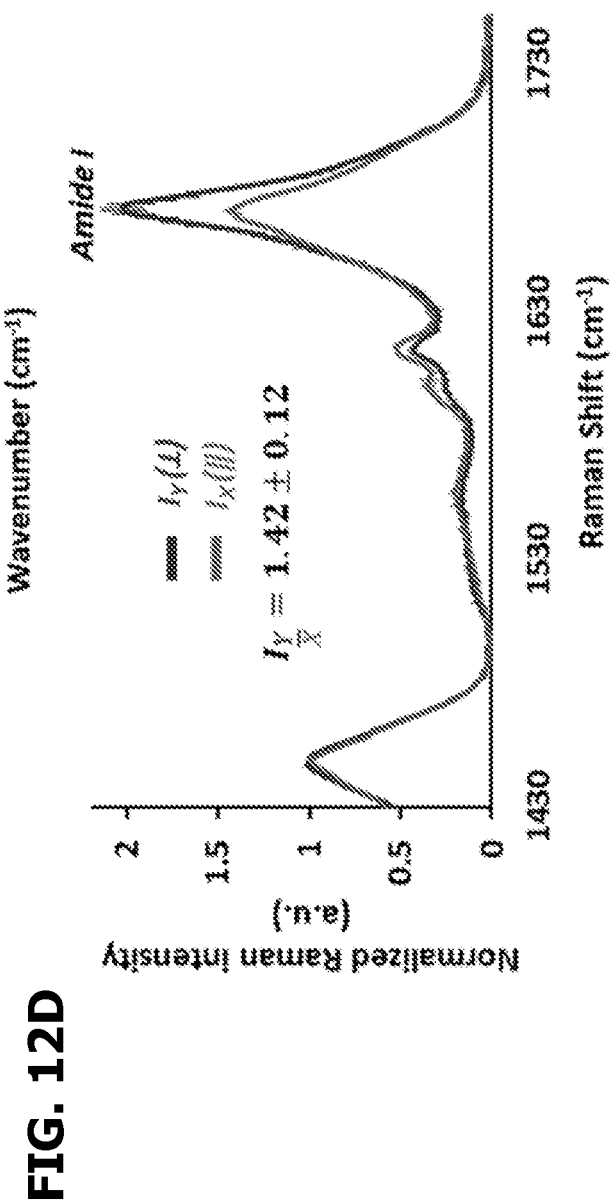

FIGS. 12A-12D show fiber characteristics at micro and molecular scales. FIG. 12A shows representative SEM micrograph of a 192-mer fiber showing a nearly circular cross-section, with a smooth exterior and dense, relatively smooth interior morphology similar to natural dragline fibers. The scale bar is 5 µm. FIG. 12B shows quantification of fiber circularity, exterior surface roughness, and interior surface roughness. Measures are from micrographs presented in FIGS. 9A-9F, FIGS. 10A-10F, and FIGS. 11A-11F. FIG. 12C shows representative FTIR amide I band deconvolution and secondary structure quantification for 192-mer fibers showing β-sheet content similar to natural dragline fibers. FIG. 12D shows amide I Raman spectra for 192-mer fibers oriented parallel (blue lines) and perpendicular (red lines) to the direction of laser polarization. The peak intensity ratio at $$1670 \text{ cm}^{-1} \left( I_{\frac{Y}{X}} \right)$$

is presented as an inset.

TABLE 2

Quantification of morphological differences between fibers of different molecular weight.

| Fiber | Circularity | Exterior Roughness | Interior Roughness |
|---|---|---|---|
| 96-mer | 0.55 ± 0.14 | 0.52 ± 0.18 | 1.00 ± 0.21 |
| 128-mer | 0.82 ± 0.10 | 0.31 ± 0.05 | 0.86 ± 0.13 |
| 192-mer | 0.89 ± 0.05 | 0.30 ± 0.04 | 0.64 ± 0.17 |

To further investigate fiber characteristics at the molecular scale, the 192-mer fibers were analyzed by Fourier-transform infrared spectroscopy (FTIR) and polarized Raman spectromicroscopy. Deconvolution of the amide I band (1600-1700 cm$^{-1}$) of the FTIR spectra confirmed a high percentage (37.9±2.3%) of β-sheet content in the 192-mer fibers (FIG. 12C), which is in close agreement with reported β-sheet content for natural dragline fibers. Meanwhile, it is established that dragline fibers exhibit a high degree of chain alignment in the axial direction, with β-sheet crystals oriented parallel to the fiber axis—an important contributing factor to the exceptional mechanical properties of dragline fibers. Here, the β-sheet alignment along the fiber axis was investigated by comparing the amide I β-sheet component (1670 cm$^{-1}$) peak intensities between spectra acquired from fibers oriented both parallel (X-axis) and perpendicular (Y-axis) to the direction of laser polarization. As expected for fibers with axial β-sheet crystal alignment, peak intensity increased markedly when fibers were oriented perpendicular to laser polarization. The 192-mer fibers exhibited a peak intensity ratio $$\left( I_{\frac{Y}{X}} \right)$$

of 1.42±0.12, indicative of substantial β-sheet anisotropy and in close agreement with reported values for natural dragline fibers following the same method (FIG. 12D).

In summary, the synthetic silk fibers produced from the SI-mediated ligation approach described herein not only replicate all major mechanical properties of natural dragline silk (strength, modulus, extensibility, and toughness) but also display similar physical properties, including microscale morphology, β-sheet content, and axial alignment of β-sheet crystals. Additionally, the observed persistence of correlation between spidroin MW and fiber strength and modulus up to 556 kDa suggests value in further pursuing the production of larger spidroins to potentially yield synthetic fibers even stronger than natural dragline silks. The fibers produced by the approach described herein may accelerate the development of applications that demand high-strength and toughness silk fibers, such as projectile protection in defense sectors, lightweight cables and ropes in aerospace sectors, or thin monofilament fibers for medical sutures. Such applications are especially likely with further improvements in process yield and perhaps through combination with recent advances in biomimetic spinning. Lastly, the platform developed and described herein may be applied to other large and highly repetitive material proteins (e.g. collagens, elastins, sucker ring teeth proteins), facilitating their microbial production from inexpensive and renewable feedstock.

Methods

Strains and Growth Conditions.

*E. coli* NEB 10-beta (NEB10β) was used for all plasmid cloning and protein production. For all cloning, *E. coli* strains were cultured in Terrific Broth (TB) containing 24 g/L yeast extract, 20 g/L tryptone, 0.4% v/v glycerol, 17 mM KH$_2$PO$_4$, and 72 mM K$_2$HPO$_4$ at 37° C. with appropriate antibiotics (50 µg/mL kanamycin and 30 µg/mL chloramphenicol). M9 glucose medium with tryptone supplement (2% w/v glucose, 1×M9 Salts, 75 mM MOPS pH 7.4, 12 g/L tryptone, 5 mM sodium citrate, 2 mM MgSO$_4$.7H$_2$O, 100 µM FeSO$_4$.7H$_2$O, 100 µM CaCl$_2$.2H$_2$O, 3 µM thiamine, 1× micronutrients [40 µM ZnSO$_4$.7H$_2$O, 20 µM CuSO$_4$.5H$_2$O, 10 µM MnCl$_2$.4H$_2$O, 4 µM H$_3$BO$_3$, 0.4 µM (NH$_4$)$_6$Mo$_7$O$_{24}$.4H$_2$O, and 0.3 µM CoCl$_2$.6H$_2$O]) was used for protein production in bioreactors.

Chemicals and Reagents.

Unless otherwise noted, all chemicals and reagents were obtained from MilliporeSigma. Plasmid purification and gel extraction kits were purchased from iNtRON Biotechnology. FastDigest restriction enzymes and T4 DNA ligase were purchased from Thermo Fisher Scientific and used for all digestions and ligations following the manufacturer's suggested protocols.

Genetic Assembly of 64- and 96-Mer Spidroins.

The multimeric spidroin DNA sequences were constructed as SI-Bricks genetic parts based on a method modified as described herein elsewhere (see also FIG. 2 and FIG. 3). Specifically, an optimized coding sequence of 1-mer *N. clavipes* MaSp1 was chemically synthesized by Integrated DNA Technologies. To fit the SI-Bricks standard, the DNA sequence was flanked on the 5' end by restriction sites 5'-KpnI/NheI-3' and on the 3' end by restriction sites 5'-SpeI/Kpn2I-3'. The sequence was inserted between restriction sites KpnI/Kpn2I of a medium copy (pBBR1 replication origin), chloramphenicol resistance ($Cm^R$) SI-Bricks expression vector, resulting in plasmid p1 (FIG. 3, step b). To begin the recursive directional genetic assembly, plasmid p1 was linearized by digestion with NheI and ligated with another 1-mer sequence digested by NheI/SpeI. The ligation was transformed to NEB10β for amplification, yielding plasmid p2 containing 2-mer spidroin (FIG. 3, step c). The same procedure was repeated for p2, with insertion of a linearized 2-mer sequence, to yield plasmid p4, and the process was repeated until p64 (32-mer+32-mer) and p96 (64-mer+32-mer) were obtained (FIG. 3, step d). Because the annealing of NheI/SpeI overhangs produces a non-cutting sequence, digestion with NheI was used to confirm proper insert direction after each ligation iteration.

Construction and Sequence Optimization of Silk-SI-Fusion Proteins.

N- and C-intein amino acid sequences ($Cfa^N$ and $Cfa^C$, respectively) were obtained from a recent publication and prepared as SI-Bricks standard parts as described below. To ensure substantial production of the final SI-fused silk proteins, the SI coding sequences were optimized for *E. coli* expression within the genetic context of all flanking sequences using a combination of computational approaches. Specifically, an initial DNA sequence was computationally designed that contains (from 5' to 3') a 5' UTR/RBS containing the EcoRI/BglII sites, a short coding sequence (5'-ATGGCTAAGACTAAA-3') intended to increase translation initiation rate, the $Cfa^C$ coding sequence, the KpnI/NheI sites, and the multimeric silk sequence. Within this genetic context, only the $Cfa^C$ sequence was set variable and optimized using a modified *E. coli* codon usage table with extra weight given to 5' mRNA structure minimization within the sequence optimization algorithm. The resulting optimized $Cfa^C$ sequence (including 5' UTR/RBS and necessary SI-Bricks restriction sites; Table 3) was synthesized as a gblock fragment by Integrated DNA Technologies and was inserted 5' of the 64-mer or 96-mer sequences by digestion/ligation with EcoRI/KpnI to yield plasmids $p^C64$ and $p^C96$, which encode fusion proteins $^C64$ and $^C96$, respectively (Table 4, FIG. 3, step e).

TABLE 3

Primers, UTRs, and coding sequences.

| Primer/UTR/Coding Sequence (CDS) | Name | Sequence | Purpose |
| --- | --- | --- | --- |
| 5' UTR | NA | ATCAGCAGGACGCACTGACCGAATTCAAAAG ATCTTTTAAGAAGGAGATATACAT (SEQ NO ID: 1) | Previously optimized 5' UTR including strong RBS for high rate of translation initiation |
| 3' UTR | NA | GGATCCAAACTCGAGTAAGGATCTCCAGGCAT CAAATAAAACGAAAGGCTCAGTCGAAAGACT GGGCCTTTCGTTTTATCTGTTGTTTGTCGGTGA ACGCTCTCTACTAGAGTCACACTGGCTCACCTT CGGGTGGGCCTTTCTGCG (SEQ NO ID: 2) | Previously optimized 3' UTR including two strong transcription terminators rmB T1 and T7Te) |
| CDS | $Cfa^N$ | TCCGGAGCAGAATATTGCCTGTCTTACGACAC AGAGATTCTGACCGTTGAATATGGATTCCTTC CTATCGGTAAGATCGTGGAGGAACGGATTGAA TGCACAGTCTATACGGTAGATAAAAATGGCTT TGTGTATACACAACCTATTGCTCAGTGGCATA ACCGGGGAGAACAGGAAGTTTTCGAATACTGC TTAGAAGACGGTTCGATTATCCGTGCAACGAA AGATCACAAATTTATGACGACCGACGGTCAGA TGTTACCGATTGATGAGATTTTCGAACGGGGG TTAGACCTGAAACAAGTTGATGGTTTGCCGTA AGGATCC (SEQ NO ID: 3) | Final optimized C-terminal SI sequence for assembly with 64-mer or 96-mer silk sequences |
| CDS | $Cfa^C$ | AGATCTTTTAAGAAGGAGATATACATATGGCT AAGACTAAAGTCAAGATCATTAGTCGTAAGAG TCTGGGCACTCAAAACGTCTACGATATTGGAG TAGAAAAAGATCATAATTTTTTGCTGAAGAAT GGGCTGGTGGCCTCTAACTGCTTCAACGGTAC C (SEQ NO ID: 4) | Final optimized N-terminal SI sequence for assembly with 64-mer or 96-mer silk sequences |
| Primer | GlyV-F | CGGAACGACGTCAATTTTTCCTGGTCACGTAA GCG (SEQ NO ID: 5) | Amplification of GlyV from *E. coli* genome and cloning into pAk backbone |
| Primer | GlyV-R | GGCTACCTCGAGTTGGGTGGTCTGTGCTTTGC AG (SEQ NO ID: 6) | Amplification of GlyV from *E. coli* genome and cloning into pAk backbone |

TABLE 4

Plasmids

| Plasmid Name | ORI | Promoter | Resistance | Gene | Plasmid Source |
|---|---|---|---|---|---|
| pB6c | pBBR1 | $P_{LlacO1}$ | $Cm^R$ | — | Lee et al. 2011[2] |
| p96 | pBBR1 | $P_{LlacO1}$ | $Cm^R$ | 96-mer | Present study |
| p64$^N$ | pBBR1 | $P_{LlacO1}$ | $Cm^R$ | 64-mer + optimized 3' $Cfa^N$ | Present study |
| p$^C$64 | pBBR1 | $P_{LlacO1}$ | $Cm^R$ | 64-mer + optimized 5' $Cfa^C$ | Present study |
| p96$^N$ | pBBR1 | $P_{LlacO1}$ | $Cm^R$ | 96-mer + optimized 3' $Cfa^N$ | Present study |
| p$^C$96 | pBBR1 | $P_{LlacO1}$ | $Cm^R$ | 96-mer + optimized 5' $Cfa^C$ | Present study |
| pA2k | p15A | $P_{Tet}$ | $Kan^R$ | — | Lee et al. 2011[2] |
| pGlyV | p15A | Native glyV promoter | $Kan^R$ | Native E. coli glyV and promoter | Present study |

Similarly, to codon-optimize $Cfa^N$, an initial DNA sequence was computationally designed containing (from 5' to 3') the multimeric silk sequence, the SpeI/Kpn2I restriction sites, a $Cfa^N$ coding sequence, and the BamHI/XhoI sites. Within this context, only $Cfa^N$ was subjected to the optimization process. The resulting $Cfa^N$ sequence (Table 2), including SI-Bricks restriction sites, was synthesized and inserted 3' of the 64-mer and 96-mer sequences by digestion/ligation with Kpn2I/XhoI to yield plasmids p64$^N$ and p96$^N$, which encode fusion proteins 64$^N$ and 96$^N$, respectively (FIG. 3, step e). The resulting SI-Bricks parts/vectors allow for easy swapping of any Int$^C$, multimeric material protein, or Int$^N$ of interest by digestion with EcoRI/KpnI, KpnI/Kpn2I, or Kpn2I/XhoI, respectively. Additionally, the presence of NheI/SpeI sites allows for in situ recursive directional genetic assembly of any large, repetitive material proteins of interest (see also FIG. 2 and FIG. 3).

Upregulation of GlyV tRNA Production.

In addition to sequence optimizations, cellular $^{glycyl}$tRNA levels were also upregulated to meet the high demands on $^{glycyl}$RNA posed by spidroin overexpression. The glyV tRNA coding sequence and its native promoter were PCR-amplified from the NEB10β genomic DNA (Table 3) and cloned between AatII/XhoI sites of a medium copy vector carrying p15A replication origin and Kanamycin resistance ($Kan^R$), yielding plasmid pGlyV (Table 4). For all spidroin expression, pGlyV was co-transformed with the spidroin plasmid.

Shake Flask Cultures.

For initial ligation tests as shown in FIGS. 5A-5C, protein production was carried out in shake flasks. Transformants were cultured overnight in 50 mL TB medium at 37° C. on an orbital shaker. Overnight 50 mL cultures were then used to inoculate 500 mL fresh TB medium in Erlenmeyer flasks at an initial $OD_{600}$=0.08. Cultures were grown at 37° C. with orbital shaking to $OD_{600}$=6, then induced by addition of 1 mM IPTG and cultured for an additional 6 hours at 30° C. with orbital shaking.

Bioproduction in Fed-Batch Bioreactors.

All spidroins were ultimately produced in 2 L fed-batch bioreactors (Bioflo120, Eppendorf). Transformants were cultured overnight in 50 mL TB medium at 37° C. on an orbital shaker. The overnight cultures were then used to inoculate 1 L glucose M9 medium with tryptone supplement at an initial $OD_{600}$=0.08. After overnight incubation at 37° C. with orbital shaking, 1 L cultures were pelleted by centrifugation at 4500×g for 10 min and resuspended in 300 mL sterile resuspension medium (250 mM MOPS pH 7.4, 2.5% w/v glucose, 60 g/L tryptone, 25 mM sodium citrate, 10 mM $MgSO_4$, 500 µM $FeSO_4.7H_2O$, 15 µM thiamine, 5× micronutrients). The resuspended cultures were then added to an autoclaved 2 L Bioflo120 heat-blanketed bioreactor containing 1.2 L water and 1.15×M9 salts. Sterile $CaCl_2.2H_2O$ was added to a final concentration of 100 µM. Antifoam 204 was added as needed to minimize foaming (approximately 0.01% v/v). Agitation and air flow was regulated to maintain approximately 70% dissolved oxygen (DO). After consumption of the initial 0.5% w/v glucose (as judged by ADO), a sterile substrate feed (20% w/v glucose, 48 g/L tryptone, and 10 g/L $MgSO_4.7H_2O$) was initiated to maintain a linear growth rate. Reactors were induced at $OD_{600}$=80 by addition of 1 mM IPTG and culture temperature was reduced to 30° C. Cultures were collected four hours after induction. Titers were estimated from densitometric analysis of Coomassie Blue-stained SDS-PAGE gels (FIGS. 4A-4B).

Protein Ligation.

Cell cultures were pelleted by centrifugation at 4500×g for 30 min. Pellets from complimentary SI-fused spidroins (e.g. 96$^N$ and $^C$96 or 64$^N$ and $^C$64) were combined at a 1:1 reactant ratio based on densitometric analysis of Coomassie Blue-stained SDS-PAGE gels. Mixed pellets were resuspended in sonication buffer (300 mM NaCl, 20 mM MOPS pH 7.4, 2 mM TCEP, 1 mM PMSF) and sonicated using a QSonica Q700 sonicator (Qsonica) for 10 min (5 s on, 10 s off). Sonicated resuspensions were pelleted by centrifugation at 25,000×g for 30 min to remove supernatants. Pellets were resuspended in ligation buffer (8 M urea, 20 mM MOPS pH 7.4, 300 mM NaCl, and 2 mM TCEP) and stirred at 37° C. for 24 h to dissolve SI-fused spidroins and ensure complete ligation. The mixtures were then centrifuged at 25,000×g for 1 h to remove cell debris and undissolved proteins.

Protein Purification.

Specifically, ligated spidroins in ligation buffer were acidified to pH 4.0 with acetic acid. Ammonium sulfate was then added to a final concentration of 1.2 M. The mixture was then centrifuged at 40,000×g for 30 min. The pellet was discarded, and additional ammonium sulfate was added to the supernatant to a final concentration of 2.3 M. After stirring for 1 h, the mixture was centrifuged again at 40,000×g for 15 min. The supernatant was discarded, and the pellet was resuspended in SEC buffer (8 M urea, 10 mM ammonium bicarbonate pH 10) for further purification by size-exclusion chromatography. SEC purifications were performed on an AKTA Pure Chromatography System (GE Healthcare Life Sciences) using a HiPrep 16/60 Sephacryl S-500 HR column (for 128-mer and 192-mer) or a HiPrep 16/60 Sephacryl S-400 HR column (for 96-mer). Proteins were separated using an isocratic elution with SEC buffer at a flow rate of 0.5 mL/min. Fractions containing greater than 90% ligation product, as determined by SDS-PAGE gel densitometry, were collected. SEC-purified fractions were combined and dialyzed in 10K MWCO SnakeSkin dialysis tubing (ThermoFisher Scientific), followed by lyophilization.

Ligation Kinetics Analysis.

For kinetics analysis, 64-mer protein concentrations in crude lysates were estimated by densitometric analysis of Coomassie Blue-stained SDS-PAGE gels. Based on estimated concentrations, fully sonicated resuspensions of $64^C$ and $^N64$ in ligation buffer were combined to give final concentrations of 100 µM for both $64^C$ and $^N64$ in a final volume of 500 µL. These mixtures were pelleted by centrifugation, and pellets were resuspended in 500 µL of desired test buffer pre-incubated at the desired test temperature. Reactions were quenched by transferring 5 µL of reaction to 95 µL of Laemmli sample buffer preheated to 100° C. and continuing boiling for 10 min.

SDS-PAGE and Densitometric Analysis.

All SDS-PAGE gels were 1 mm thick, discontinuous with 3% stacking gel, and hand cast at the indicated percentages. Samples were prepared at 1 mg/mL or 5 µM total protein in Laemmli sample buffer (2% SDS, 10% glycerol, 60 mM Tris pH 6.8, 0.01% bromophenol blue, 100 µM DTT). Gels were run on Mini-PROTEAN Tetra Cells (Bio-Rad) in 1× Tris-glycine SDS buffer (25 mM Tris base, 250 mM glycine, 0.1% w/v SDS), until just before the dye front exited the gel. Gels were stained in Coomassie Blue solution (50% methanol, 10% w/v acetic acid, 1 g/L Coomassie Brilliant Blue) for a minimum of one hour at room temperature with gentle agitation and destained in Coomassie Blue destain buffer (40% v/v methanol, 10% v/v acetic acid) for a minimum of one hour. Gels were imaged on an Azure c600 Imager (Azure Biosystems). All densitometry analysis was performed with the AzureSpot Analysis Software (Azure Biosystems). Images were background subtracted with a built-in automatic lane edge subtraction algorithm. Protein band intensities were integrated by the AzureSpot software. Ligation yield was calculated as the integrated intensity of the product band over the sum of both reactant and product band areas. Purity was calculated as the integrated intensity of the product band over the integrated intensity of all other bands. Spidroin titer was calculated as the integrated intensity of the spidroin band over the integrated intensity of all other bands multiplied by the measured cell density ($OD_{600}$) of culture at the time of sampling and 150 mg/L/$OD_{600}$ (150 mg/L/$OD_{600}$ is an average typical total protein titer for *E. coli* grown in glucose minimal medium).

Fiber Spinning and Mechanical Testing.

Fiber spinning and mechanical testing were performed following a modified protocol. Lyophilized spidroin powders were dissolved in hexafluorisopropanol (HFIP) to 17% w/v. This protein dope was loaded to a 100 µL Hamilton gastight syringe (Hamilton Robotics) fitted with a 23s gauge (116 µm inner diameter, 1.71 inch length) needle. The syringe was fitted to a Harvard Apparatus Pump 11 Elite syringe pump (Harvard Apparatus), and the dope was extruded into a 95% v/v methanol bath at 5 µL/min. Extruded fibers were then transferred to a 75% v/v methanol bath and carefully extended at approximately 1 cm/s to the maximum draw ratio without fiber fracture. Extended fibers were removed from the bath and held under tension until visibly dry. Segments of post-drawn fibers (20 mm) were carefully laid exactly vertical across a 5 mm (vertical)×15 mm (horizontal) opening cut into a 20 mm×20 mm piece of cardstock and fixed with adhesive tape at both ends of the opening. Diameters of mounted fibers were then measured by light microscopy, averaging measurements at three points along the fiber axis (Tables 5-7, FIG. 8).

TABLE 5

Diameter measurements and mechanical properties for 96-mer fibers

| FIBER | Diam. A (µm) | Diam. B (µm) | Diam. C (µm) | Avg. Diameter (µm) | σ (MPa) | E (GPa) | ε (%) | $U_T$ (MJ/m³) |
|---|---|---|---|---|---|---|---|---|
| 1 | 6.53 | 6.22 | 5.57 | 6.11 | 566.7 | 7.4 | 25.4 | 110.0 |
| 2 | 5.89 | 6.22 | 5.58 | 5.90 | 526.6 | 7.6 | 21.8 | 90.0 |
| 3 | 7.80 | 7.33 | 7.48 | 7.54 | 401.3 | 5.6 | 26.7 | 90.0 |
| 4 | 6.69 | 7.21 | 7.50 | 7.13 | 520.8 | 8.1 | 33.0 | 130.0 |
| 5 | 6.53 | 5.93 | 6.40 | 6.29 | 475.2 | 6.9 | 32.2 | 120.0 |
| 6 | 5.91 | 6.05 | 6.85 | 6.27 | 447.9 | 6.6 | 22.9 | 70.0 |
| 7 | 7.86 | 6.38 | 8.61 | 7.62 | 515.4 | 8.7 | 36.1 | 140.0 |
| 8 | 6.24 | 6.08 | 6.69 | 6.34 | 558.8 | 8.9 | 15.3 | 60.0 |
| 9 | 5.58 | 5.26 | 5.42 | 5.42 | 672.2 | 8.6 | 21.7 | 110.0 |
| 10 | 5.57 | 4.94 | 5.10 | 5.20 | 670.3 | 9.8 | 18.3 | 90.0 |
| 11 | 6.58 | 7.35 | 6.42 | 6.78 | 397.1 | 5.3 | 15.6 | 40.0 |
| 12 | 5.42 | 6.53 | 6.42 | 6.12 | 504.4 | 7.8 | 16.2 | 60.0 |
| 13 | 5.42 | 5.73 | 6.05 | 5.73 | 574.3 | 9.1 | 22.1 | 100.0 |
| 14 | 6.21 | 6.53 | 5.42 | 6.05 | 524.3 | 9.1 | 15.2 | 60.0 |

TABLE 6

Diameter measurements and mechanical properties for 128-mer fibers

| FIBER | Diam. A (µm) | Diam. B (µm) | Diam. C (µm) | Avg. Diameter (µm) | σ (MPa) | E (GPa) | ε (%) | $U_T$ (MJ/m³) |
|---|---|---|---|---|---|---|---|---|
| 1 | 7.33 | 7.05 | 6.63 | 7.00 | 874.4 | 11.4 | 39.2 | 260.0 |
| 2 | 6.56 | 7.68 | 6.03 | 6.76 | 886.1 | 9.5 | 18.9 | 100.0 |
| 3 | 7.96 | 5.47 | 5.65 | 6.36 | 650.2 | 8.4 | 12.7 | 50.0 |
| 4 | 7.49 | 5.87 | 6.00 | 6.45 | 652.1 | 8.0 | 29.5 | 150.0 |
| 5 | 4.98 | 3.54 | 4.66 | 4.39 | 642.9 | 12.9 | 9.5 | 40.0 |
| 6 | 7.18 | 6.42 | 7.07 | 6.89 | 877.2 | 12.6 | 33.3 | 200.0 |
| 7 | 6.76 | 6.91 | 6.34 | 6.67 | 654.3 | 9.0 | 19.4 | 80.0 |
| 8 | 5.77 | 5.74 | 6.55 | 6.02 | 843.0 | 9.5 | 16.8 | 90.0 |
| 9 | 6.36 | 6.53 | 5.75 | 6.21 | 816.2 | 10.7 | 15.2 | 110.0 |
| 10 | 7.01 | 6.85 | 7.66 | 7.17 | 750.4 | 9.6 | 22.0 | 90.0 |
| 11 | 7.91 | 7.91 | 7.37 | 7.73 | 744.8 | 8.2 | 27.3 | 130.0 |
| 12 | 6.41 | 5.65 | 5.59 | 5.88 | 817.5 | 11.8 | 17.4 | 90.0 |
| 13 | 6.69 | 7.50 | 8.13 | 7.44 | 717.0 | 10.7 | 25.5 | 120.0 |
| 14 | 7.41 | 8.51 | 8.20 | 8.04 | 816.7 | 12.3 | 20.0 | 100.0 |

TABLE 7

Diameter measurements and mechanical properties for 192-mer fibers

| FIBER | Diam. A (µm) | Diam. B (µm) | Diam. C (µm) | Avg. Diameter (µm) | σ (MPa) | E (GPa) | ε (%) | $U_T$ (MJ/m³) |
|---|---|---|---|---|---|---|---|---|
| 1 | 3.02 | 3.04 | 2.75 | 2.94 | 1078.6 | 14.7 | 11.7 | 70.0 |
| 2 | 6.56 | 7.68 | 7.34 | 7.19 | 892.9 | 9.0 | 15.3 | 70.0 |
| 3 | 4.98 | 7.41 | 7.37 | 6.59 | 1034.8 | 17.8 | 28.0 | 200.0 |
| 4 | 6.91 | 6.89 | 6.72 | 6.84 | 1135.6 | 11.8 | 17.7 | 110.0 |
| 5 | 7.32 | 7.33 | 7.64 | 7.43 | 911.5 | 12.2 | 14.0 | 80.0 |
| 6 | 6.34 | 5.50 | 6.13 | 5.99 | 1324.6 | 18.9 | 27.2 | 220.0 |
| 7 | 3.19 | 3.38 | 3.06 | 3.21 | 1130.5 | 17.2 | 15.6 | 100.0 |
| 8 | 5.25 | 5.89 | 5.10 | 5.41 | 982.8 | 10.5 | 18.4 | 100.0 |
| 9 | 4.80 | 5.12 | 5.81 | 5.24 | 987.6 | 10.3 | 24.6 | 140.0 |
| 10 | 5.73 | 5.73 | 7.01 | 6.16 | 1003.0 | 14.3 | 12.2 | 70.0 |
| 11 | 5.65 | 5.91 | 6.15 | 5.90 | 961.7 | 14.5 | 21.8 | 140.0 |
| 12 | 5.78 | 5.91 | 5.92 | 5.87 | 1016.0 | 11.9 | 12.1 | 70.0 |
| 13 | 6.53 | 5.89 | 5.57 | 6.00 | 1016.6 | 13.1 | 12.8 | 70.0 |
| 14 | 5.09 | 5.29 | 4.94 | 5.11 | 952.4 | 15.2 | 24.3 | 160.0 |

Mechanical properties were measured by axial pull tests on an MTS Criterion Model 41 universal test frame fitted with a 1 N load cell (MTS Systems Corporation). Cardstock holders were mounted between two opposing spring-loaded grips, and the supporting edges were carefully cut. Pull tests were conducted at a relative humidity of 30%, with a constant crosshead speed of 10 mm/min. Stress-strain curves were recorded by the MTS TW Elite test suite at a sampling rate of 50 Hz. Fiber breaks were recorded when a 90% drop from peak stress was detected. All mechanical properties were automatically calculated by the MTS TW Elite test suite. Ultimate tensile strength was calculated as the maximum measured load over the initial fiber cross-sectional area ($A=\pi r^2$), as determined from measured initial diameters. Modulus was calculated as the slope of a linear least squares fit to the stress/strain data of the initial elastic region. Toughness was calculated as the area under the total stress/strain curve divided by the initial fiber volume ($V=\pi r^2 h$) as calculated from measured initial fiber diameters and set initial gage length of 5 mm. For each protein, a total of 14 fibers were measured in this manner.

Light Microscopy.

Fiber diameters were measured using images acquired with a Zeiss Axio Observer ZI Inverted Microscope equipped with a phase contrast 20× objective lens and the Axiovision LE software (Zeiss). For morphological analysis and further confirmation of fiber diameters, additional images were acquired with a Nikon Eclipse TiE Inverted Microscope equipped with a 60× objective and analyzed using the Nis-Elements software (Nikon; FIG. 8).

Scanning Electron Microscopy.

Following tensile tests, silk fibers were mounted onto a sample holder using conductive tape. The sample holder was sputter coated with a 10 nm gold layer using a Leica EM ACE600 high vacuum sputter coater (Leica Microsystems). Fibers were imaged using a Nova NanoSEM 230 Field Emission Scanning Electron Microscope (Field Electron and Ion Company, FEI) at an accelerating voltage of 7-10 kV. Fiber surface roughness (both exterior and interior) was calculated using MountainsMap SEM Topo software (Digital Surf). The root mean square height (Sq) of each surface was determined from single images using greyscale values, normalized by the entire range of values in each micrograph. To remove fiber curvature from consideration, a standard Gaussian filter with a threshold of 2.5 μm was applied when analyzing exterior surfaces. For convenience, exterior and interior surface roughness values are presented relative to each other, with the highest interior value set at 1. Fiber circularity was calculated from cross-sectional areas and perimeters as $$4\pi\left(\frac{area}{perimeter^2}\right),$$

where a perfect circle gives a value of 1.

Polarized Raman Spectromicroscopy.

An adapted molecular alignment in spider silk fibers is reported herein. Silk fibers were carefully fixed to glass microscope slides with microscale markings to ensure that spectra were acquired at the same location before and after stage rotation. Raman spectra were acquired with a Renishaw RM1000 InVia Confocal Raman Spectrometer (Renishaw) coupled to a Leica DM LM microscope with rotating stage (Leica Microsystems). Silk fibers were initially oriented along the x-axis (FIG. 13).

Figure 13:
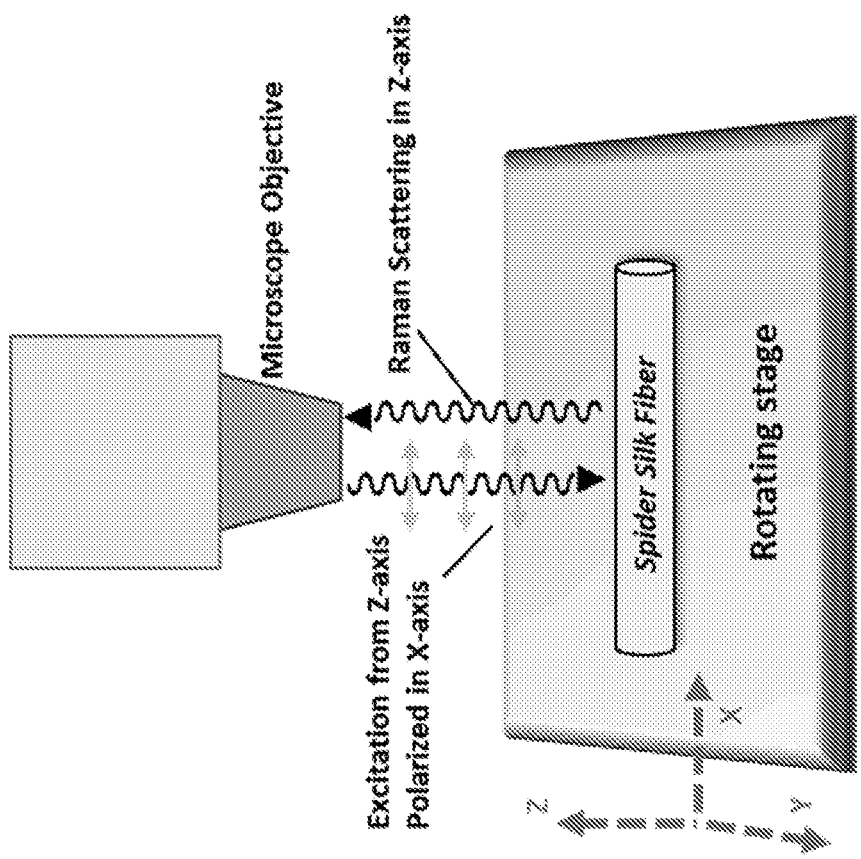
FIG. 13 is an exemplary embodiment of polarized Raman microspectroscopy in accordance with the present disclosure.

FIG. 13 shows polarized Raman microspectroscopy. Schematic representation of the apparatus from a side view. The fiber is mounted along the X-axis of a rotating stage. A laser polarized in the X-axis is directed to the fiber along the Z-axis through a magnifying objective. Raman scattering is collected back through the objective along the Z-axis.

Fibers were irradiated at a fixed point with the 514 nm line of an argon laser with polarization fixed along the x-axis and focused through a 50× objective (NA=0.75). Spectra were recorded from 1150-1750 $cm^{-1}$ with an 1800 lines/mm grating. For each acquisition, a total of 16 spectra were accumulated, each for 10 s. The stage was then rotated to orient fibers along the y-axis with the same laser polarization, and spectra were acquired a second time at the same fixed point. No signs of thermal degradation were apparent either visually or within recorded spectra. All recorded spectra were analyzed using Fityk 0.9.8. Baselines were subtracted from all spectra using the built-in Fityk automatic convex hull algorithm. For intensity ratio calculations, all spectra were normalized to the intensity of the 1450 $cm^{-1}$ peak, which arises from $CH_2$ bending and is insensitive to protein conformation. For each fiber, the normalized intensity of the peak at 1670 $cm^{-1}$ when oriented along the Y-axis was divided by the normalized intensity of the peak when oriented along the X-axis to give the intensity ratio $$\left(I\frac{Y}{X}\right).$$

This procedure was performed on a total of three separate fibers and calculated intensity ratios were averaged. Spectra were also averaged and presented in FIG. 12D with standard deviations for each point along the spectra.

Fourier Transform Infrared Spectroscopy.

For secondary structure determination, FTIR spectra were acquired with a Thermo Nicolet 470 FT-IR spectrometer (ThermoFisher Scientific) fitted with a Smart Performer ATR accessory with Ge crystal. Spectra were acquired from 1350-1750 $cm^{-1}$ at 4 $cm^{-1}$ resolution. A total of 254 scans were accumulated for each sample. All recorded spectra were analyzed using Fityk 0.9.8. Baselines were subtracted from all spectra using the built-in Fityk convex hull algorithm. The amide I band (1600-1700 $cm^{-1}$) was deconvolved into a set of five Lorentzian peaks centered at 1626.5, 1646.5, 1659, 1679.5, and 1700 $cm^{-1}$ for β-sheet, random coil, α-helix, β-turn, and β-sheet components, respectively. Component peak assignments were based on known assignments. Peak areas were integrated and percentages were calculated as the component peak area over the sum of all peak areas. Percentages were averaged from measurements of three fibers.

Statistical Analysis.

GraphPad Prism 7 (GraphPad Software) was used for statistical data analysis, using both two-tailed unpaired t-tests (26 degrees of freedom) and one-way ANOVA tests (41 degrees of freedom) to compare data sets.

Figure 14B:
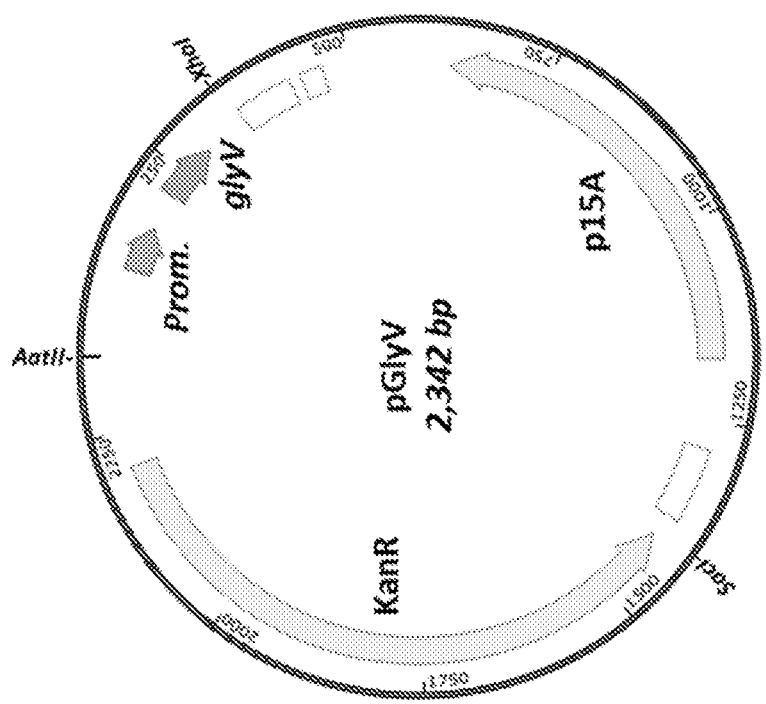
FIG. 14A and FIG. 14B are exemplary embodiments of p96 and pGlyV plasmid maps in accordance with the present disclosure.
Figure 14A:
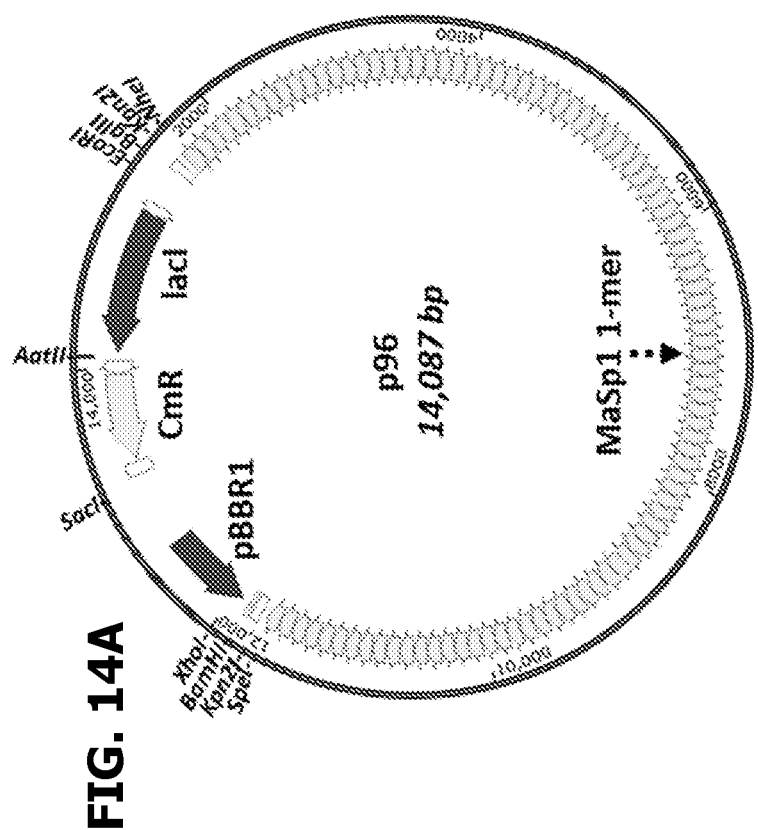

Plasmid maps are shown in FIGS. 14A-14B and FIGS. 15A-15D. FIG. 14A and FIG. 14B show p96 and pGlyV plasmid maps, respectively. "Prom." indicates native *E. coli* glyV,X,Y promoter. FIGS. 15A-15D show plasmid maps for p64$^N$ (FIG. 15A), p$^C$64 (FIG. 15B), p96$^N$ (FIG. 15C), p$^C$96 (FIG. 15D). Tables 8 and 9 list peptide sequences and strains, respectively.

TABLE 8

Peptide sequences

| Peptide Name | Sequence | Purpose | Original Peptide Sequence Source |
|---|---|---|---|
| MaSp1 1-mer | SGRGGLGGQGAGMAAAAAMG GAGQGGYGGLGSQG (SEQ NO ID: 7) | 1-mer sequence used for assembly of 64-mer and 96-mer spidroins | Sezla et al. 2000[3] |
| Cfa$^N$ | AEYCLSYDTEILTVEYGFLPIGK IVEERIECTVYTVDKNGFVYTQ PIAQWHNRGEQEVFEYCLEDG SIIRATKDHKFMTTDGQMLPID EHAERGLDLKQVDGLP* (SEQ NO ID: 8) | N-intein sequence for ligation of 64-mer or 96-mer spidroins | Stevens et al. 2016[4] |
| Cfa$^C$ | MVKIISRKSLGTQNVYDIGVEK DHNFLLKNGLVASNCFN (SEQ NO ID: 9) | C-intern sequence for ligation of 64-mer or 96-mer spidroins | Stevens et al. 2016[4] |

TABLE 9

| Strain Name | Genotype | Strain Source |
|---|---|---|
| NEB10β | F proA+B + lacIq Δ(lacZ)M15 zzf::Tn10 (TetR)(ara-leu)7697 araD139 fhuA ΔlacX74 galK16 galE15 e14- Φ80dlacZΔM15 recA1 relA1 endA1 nupG rpsL (StrR) rphspoT1 Δ(mrr-hsdRMS-mcrBC) | NEB |
| s96 | NEB10β containing p96 + pGlyV | Present study |
| s64$^N$ | NEB10β containing p64$^N$ + pGlyV | Present study |
| s$^C$64 | NEB10β containing p$^C$64 + pGlyV | Present study |
| s96$^N$ | NEB10β containing p96$^N$ + pGlyV | Present study |
| s$^C$96 | NEB10β containing p$^C$96 + pGlyV | Present study |

In Vivo Seeded Chain-Growth Polymerization for the Bioproduction of High Molecular Weight Spidroins Microbially produced protein-based materials are appealing due to renewable feedstocks, low-energy production, precisely tunable side-chain chemistries, biocompatibility, and biodegradability. However, the production of high strength protein-based materials typically requires the production of high molecular weight, repetitive proteins that are difficult to efficiently produce in microbial hosts due to genetic instability and metabolic burden. As described herein the development of a modular biosynthetic platform is reported, termed seeded chain growth polymerization, for production of high molecular weight protein-based materials via post-translational split-intein mediated polymerization of relatively small, genetically stable material protein subunits. As a proof of concept, seeded chain growth polymerization was applied to the production of biosynthetic spider silk proteins in E. coli. While unseeded polymerization yielded primarily low molecular cyclic byproducts, seeded chain growth polymerization generated native-sized, linear dragline spidroin polymers (>300 kDa)—permitting efficient production of biosynthetic spider silk fibers of high strength, modulus, and toughness. By allowing efficient production of large, repetitive material proteins from more easily expressed, genetically stable subunits, the seeded chain growth method can facilitate production of a variety of high performance protein-based materials for practical commercial applications.

Disclosed herein is a unique method for efficient post-translational assembly of repetitive proteins in living bacterial cells through SI-based polymerization. An in vivo protein polymerization method, termed seeded chain-growth polymerization (SCP), mimics the chain-growth polymerization in organic polymer science. SCP effectively blocks the formation of cyclic proteins that are otherwise a major product of uncontrolled SI-based polymerization. As a proof of concept for this platform, the application of SCP to the production of high MW dragline spidroins in engineered E. coli was demonstrated.

In some embodiments, the present disclosure is directed to a method for synthesizing a spidroin. The method comprises synthesizing a seed protein in vivo in a heterologous host, the seed protein comprising a C-terminus Int$^N$ domain, synthesizing a monomer in vivo in the heterologous host, the monomer comprising an N-terminus Int$^C$ domain and a C-terminus Int$^N$ domain, and co-translationally polymerizing the monomer via in vivo split-intein mediated polymerization.

In some embodiments the heterologous host is a protein-expressing microbial host and/or the monomer is a silk amino acid sequence from a spider species. In some embodiments, the heterologous host is E. coli, and/or the monomer is an N. clavipes spidroin. In some embodiments, the synthesized spidroin has a molecular weight of at least about 300 kDa, at least about 400 kDA, at least about 500 kDa, or at least about 600 kDa. In some embodiments the method further comprises spinning the synthesized spidroin into fibers. In some embodiments, the fibers have a tensile strength of from about 150 MPa to about 350 MPa, or from about 170 MPa to about 310 MPa. In some embodiments, the fibers have a modulus of about 3.0 GPa to about 5.5 GPa. In some embodiments, the fibers have a toughness of from about 25 MJ/m$^3$ to about 150 MJ/m$^3$, or from about 55 MJ/m$^3$ to about 105 MJ/m$^3$. In some embodiments, the fibers have a β-sheet content of from about 20% to about 60%, or from about 35% to about 45%. In some embodiments, the synthesized spidroin has a molecular weight of In some embodiments, the fibers have an extensibility of from about 5% to about 35%, or from about 10% to about 25%.

In some embodiments, a method for synthesizing a spidroin comprises: synthesizing a seed protein in vivo in a heterologous host, the seed protein comprising a C-terminus $Int^N$ domain; synthesizing a monomer in vivo in the heterologous host, the monomer comprising both an N-terminus $Int^C$ domain and a C-terminus $Int^N$ domain; and undergoing multiple steps of co-translational ligation of the monomer via in vivo split-intein mediated reaction. In some embodiments, the heterologous host is E. coli, or other protein expressing microbial hosts. In some embodiments, the monomer contains a fragment of silk amino acid sequence from N. clavipes spidroin or other spider species. In some embodiments, the synthesized spidroin is a linear polymer. In some embodiments, the synthesized spidroin has a molecular weight of at least about 300 kDa. In some embodiments, the method further comprises spinning the synthesized spidroin into fibers. In some embodiments, the fibers have a tensile strength of from about 170 MPa to about 310 MPa, or at least about 300 MPa. In some embodiments, the fibers have a toughness of from about 55 MJ/m³ to about 105 MJ/m³, or at least about 100 MJ/m³.

In some embodiments, the present disclosure is directed to a system for synthesizing a spidroin in vivo. The system comprises a host cell, a seed cassette encoding a seed protein comprising a C-terminus $Int^N$ domain, and a monomer cassette encoding a monomer comprising an N-terminus $Int^C$ domain and a C-terminus $Int^N$ domain.

In some embodiments the host cell is a protein-expressing microbial host and/or the monomer is a silk amino acid sequence from a spider species. In some embodiments, the host cell is E. coli, and/or the monomer is an N. clavipes spidroin. In some embodiments, the fibers have a tensile strength of from about 150 MPa to about 350 MPa, or from about 170 MPa to about 310 MPa. In some embodiments, the fibers have a toughness of from about 25 MJ/m³ to about 150 MJ/m³, or from about 55 MJ/m³ to about 105 MJ/m³. In some embodiments, the fibers have a β-sheet content of from about 20% to about 60%, or from about 35% to about 45%. In some embodiments, the synthesized spidroin has a molecular weight of at least about 300 kDa, at least about 400 kDA, at least about 500 kDa, or at least about 600 kDa. In some embodiments, the fibers have an extensibility of from about 5% to about 35%, or from about 10% to about 25%.

In some embodiments, a system for synthesizing a spidroin in vivo comprises: a host cell; a seed cassette encoding a seed protein comprising a C-terminus $Int^N$ domain; and a monomer cassette encoding a monomer comprising an N-terminus $Int^C$ domain and a C-terminus $Int^N$ domain. In some embodiments, the host cell is E. coli, or other protein expressing microbial hosts. In some embodiments, the monomer contains a fragment of silk amino acid sequence from N. clavipes spidroin or other spider species.

Results and Discussion

SI-Based Polymerization of Dragline Spidroins in E. coli.

Figures 16A, 16B:
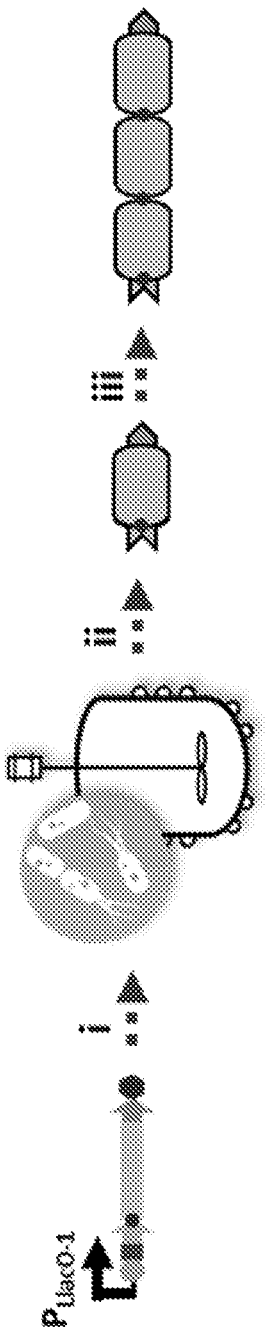
FIG. 16A and FIG. 16B are exemplary embodiments of in vivo Split Intein (SI) mediated polymerization of *N. clavipes* dragline spidroin yields low MW, apparently cyclic oligomers in accordance with the present disclosure.

To first test the feasibility of SI-based polymerization of material proteins in E. coli, a 27.5 kDa "monomer" was employed containing 10 repeats of an N. clavipes MaSp1 dragline spidroin consensus sequence with a histidine tag for protein detection and purification purposes (FIG. 16A).

FIGS. 16A and 16B show in vivo Split Intein (SI) mediated polymerization of N. clavipes dragline spidroin yields low MW, apparently cyclic oligomers. (FIG. 16A) An idealized schematic for SI-mediated polymerization for production of HMW PBMs. In step (i) a relatively small, easily expressed genetic subunit "monomer" is flanked by complimentary SIs and the optimized DNA sequence is assembled and transformed to metabolically engineered E. coli for bioproduction. In step (ii) cell cultures are induced with 1 mM IPTG to produce reactive SI-flanked protein subunits which undergo polymerization. (FIG. 16B) Western blot of whole cell lysates from cultures producing SI-flanked 10× N. clavipes dragline spidroin monomers, suggesting the production of low MW, apparently cyclic oligomers. Expected sizes of the cyclic products are noted in parentheses. "10×" indicates monomer, subscript "$_c$" indicates cyclic products, and subscript numbers indicate the number of reacted monomers within the product.

The sequence was genetically optimized for efficient expression in E. coli and flanked by a pair of complementary, fast reacting gp41-1 SIs in the form of $Int^C$-monomer-$Int^N$ (FIG. 17A), where $Int^C$ and $Int^N$ represent the C- and N-half of SI. This "monomer cassette" was placed under the control of an IPTG-inducible $P_{LacO1}$ promoter. The monomer cassette was induced for expression at exponential growth phase, and anti-His-Tag western blotting was used to analyze the products.

Figure 17A:
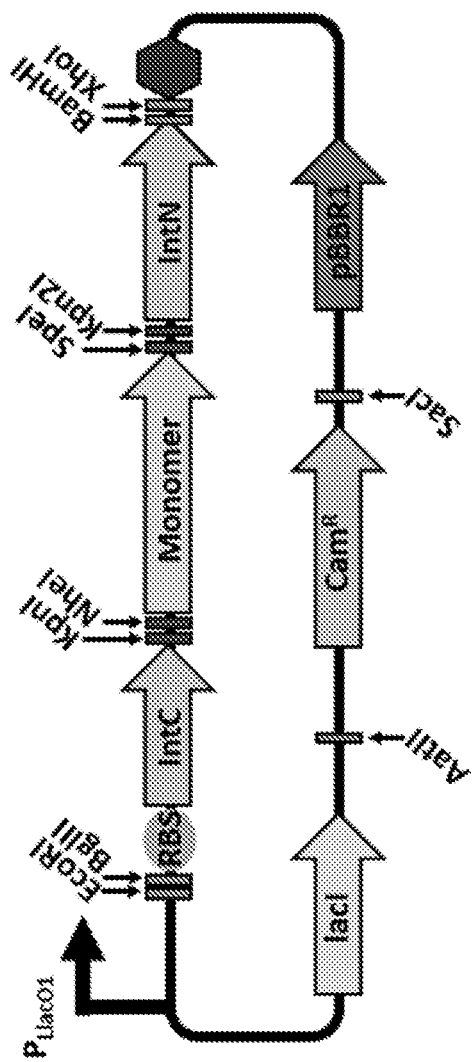
FIG. 17A and FIG. 17B are exemplary embodiments of a schematic of SI-Bricks monomer and seed cassettes needed for in vivo seeded chain-growth polymerization (SCP) in accordance with the present disclosure.
Figure 17B:
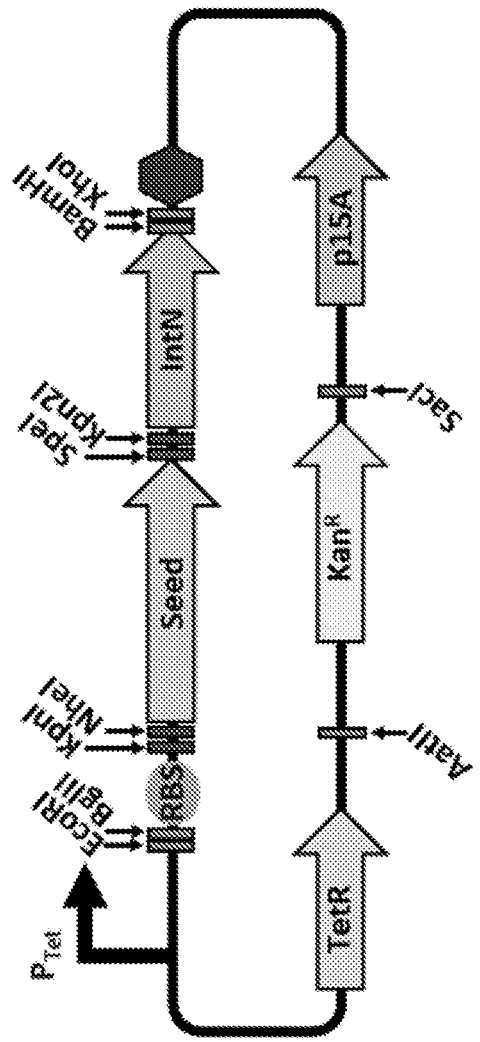

FIGS. 17A and 17B show schematics of SI-Bricks monomer and seed cassettes needed for in vivo seeded chain-growth polymerization (SCP). In FIG. 17A the monomer cassette is controlled by an IPTG-inducible $P_{LacO1}$ promoter, carries chloramphenicol resistance gene and a pBBR1 replication origin. FIG. 17B the seed cassette is controlled by an ATc-inducible promoter, carries kanamycin resistance and a p15A replication origin.

Interestingly, the polymerization products were primarily low MW oligomers (FIG. 16B), running slightly faster than expected monomer or dimmer, suggesting the formation of cyclic proteins instead of linear HMW products. SI-catalyzed protein cyclization has been reported, with products running faster than linear proteins on SDS-PAGE, presumably due to the smaller hydrodynamic radius of cyclic proteins relative to their linear counterparts. Intramolecular cyclization is preferred over intermolecular ligation if monomer structural flexibility permits N- and C-termini to reach reaction proximity. In the case of the N. clavipes MaSp1 dragline spidroin, its intrinsically disordered structure likely promotes cyclization over linear polymerization.

Development of SCP for Production of HMW Linear Dragline Spidroins in E. coli.

Figure 18:
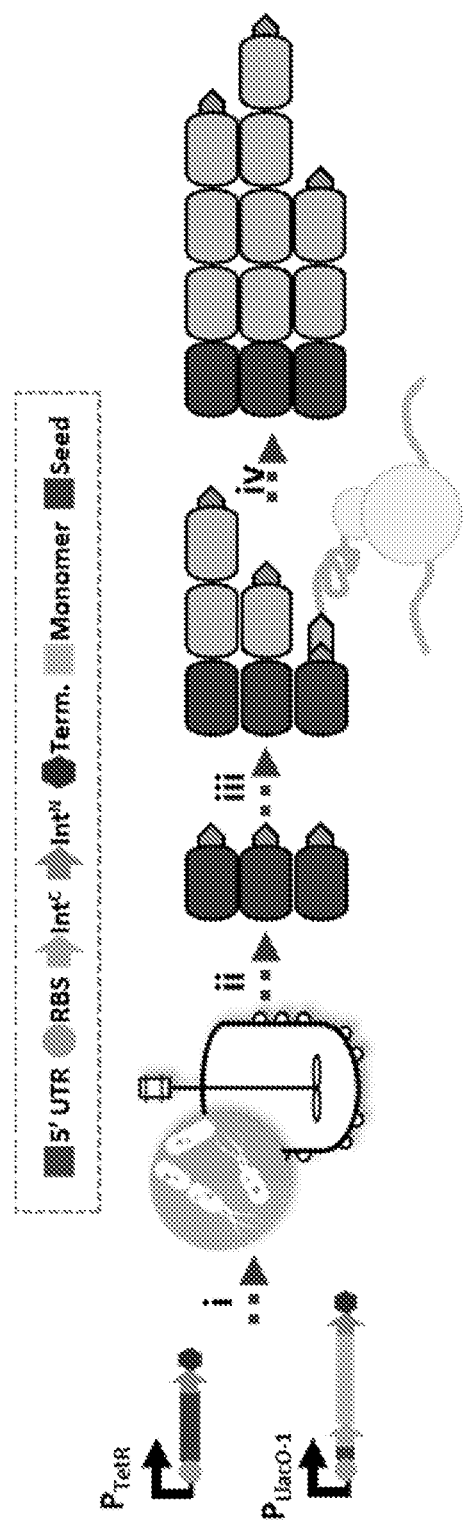
FIG. 18 is an exemplary embodiment of a process schematic for in vivo seeded chain-growth polymerization (SCP) in accordance with the present disclosure.

To prevent cyclization and shift production toward HMW linear spidroins, a method termed seeded chain-growth polymerization (SCP) was devised, which mimics chain-growth polymerization in organic polymer science by first inducing a "seed protein", which only contains one reactive $Int^N$ domain fused at the C-terminus of the seed (FIG. 18).

FIG. 18 shows a process schematic for in vivo seeded chain-growth polymerization (SCP). To inhibit the formation of low MW cyclic oligomers during in vivo SI-based polymerizations and drive production of $HMW_{linear}$ polymers, SCP was devised wherein a seed protein containing $Int^N$ at its C-terminus is co-transformed with the $Int^C$-monomer-$Int^N$ cassette (i). Production of the seed cassette is first initiated by addition of anhydrotetracycline (ATc) (ii). After sufficient seed is produced, monomer production is induced by addition of IPTG (iii). Given sufficient reactive seed protein, nascent $Int^C$ domain at the N-terminus of monomer will react with seed or growing linear chains before the $Int^N$ domain at the C-terminus of the monomer is translated, effectively eliminating cyclization (iv).

After a certain time, the $Int^C$-monomer-$Int^N$ cassette is subsequently expressed. Provided sufficient intracellular concentrations of reactive seed or growing linear chains, the $Int^C$ domain at the N-terminus of a nascent monomer react with seed or linear chain before its C-terminal $Int^N$ domain can be translated, resulting in linear intermolecular ligation without cyclization. As a seed protein for dragline spidroin production, the non-repetitive N-terminal domain of *N. clavipes* MaSp1 dragline silk (termed NTD, 25.2 kDa) was chosen. Thus, Int$^N$ was genetically fused to the C-terminus of NTD, yielding a "seed cassette" in the form of NTD-Int$^N$ (FIG. 17B). To control seed production, NTD-Int$^N$ was placed 3' of a P$_{Tet}$ promoter so that its expression can be controlled separately from the monomer cassette. Given the similarity in MW of the seed cassette and 10× monomer cassette, for all SCP experiments, a 20 kDa monomer cassette was employed containing 7 repeats of the *N. clavipes* dragline consensus sequence.

Optimization of SCP.

To test SCP in living *E. coli* cells and optimize reaction conditions, cells were induced with a range of anhydrotetracycline (ATc) concentrations (50-175 nM) for 1 h followed by addition of 1 mM IPTG to induce monomer cassette. Cells were then incubated for 0-6 h to monitor silk polymerization (FIGS. 19A-19C).

Figure 19A:
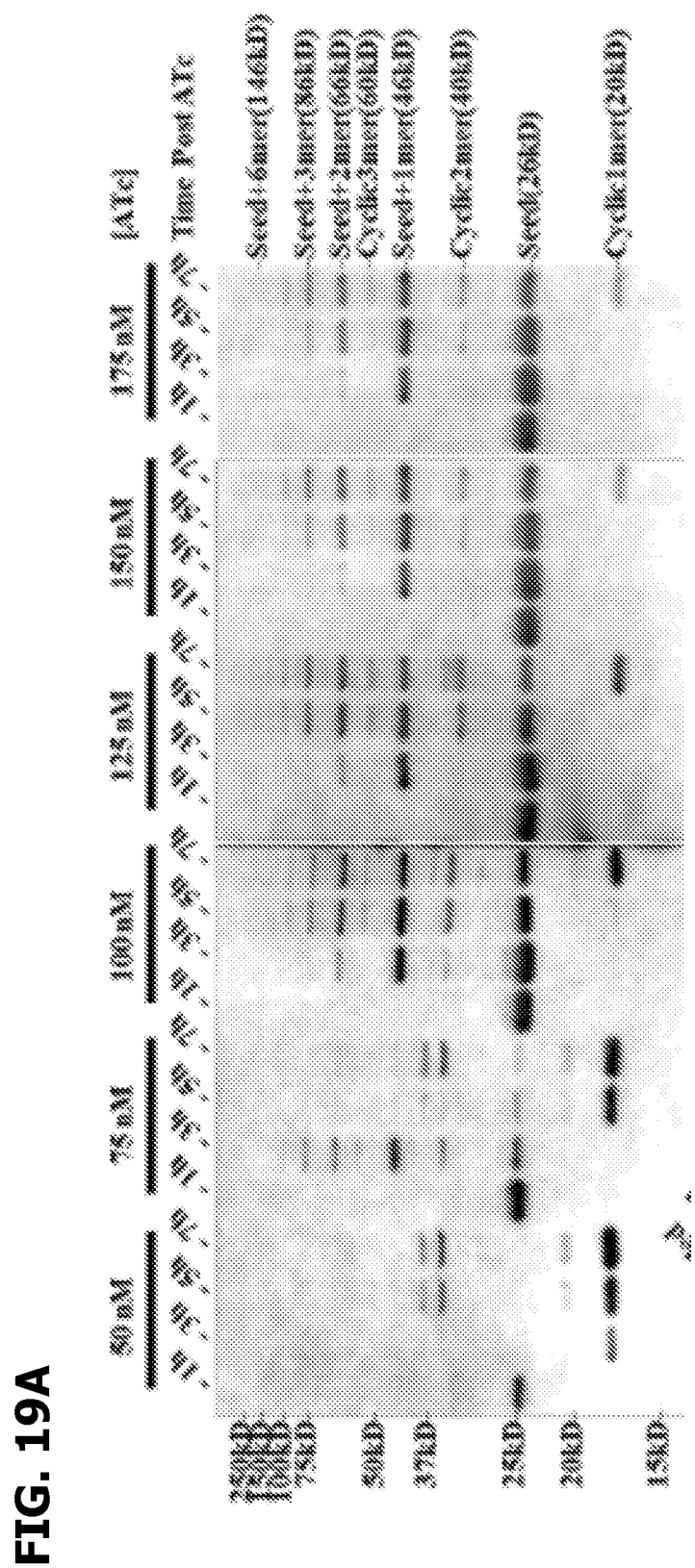
FIG. 19A, FIG. 19B, and FIG. 19C are exemplary embodiments of optimization of seed and monomer induction timing for production of linear high MW spidroins by SCP in accordance with the present disclosure.
Figure 19B:
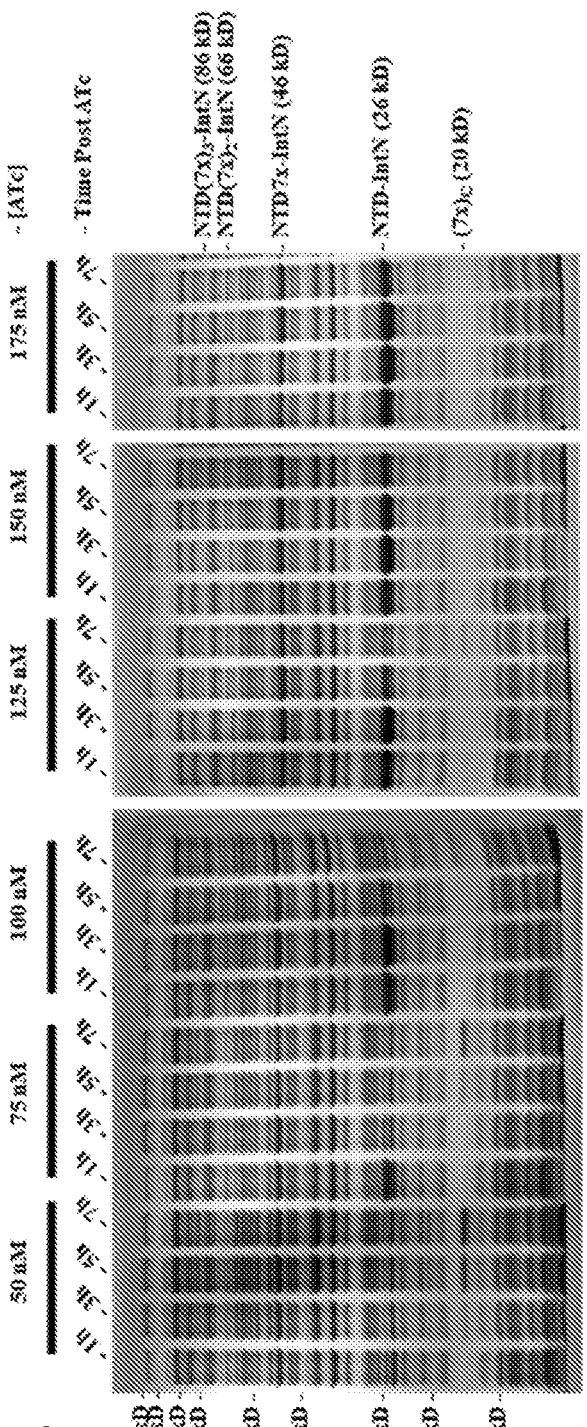
Figure 19C:
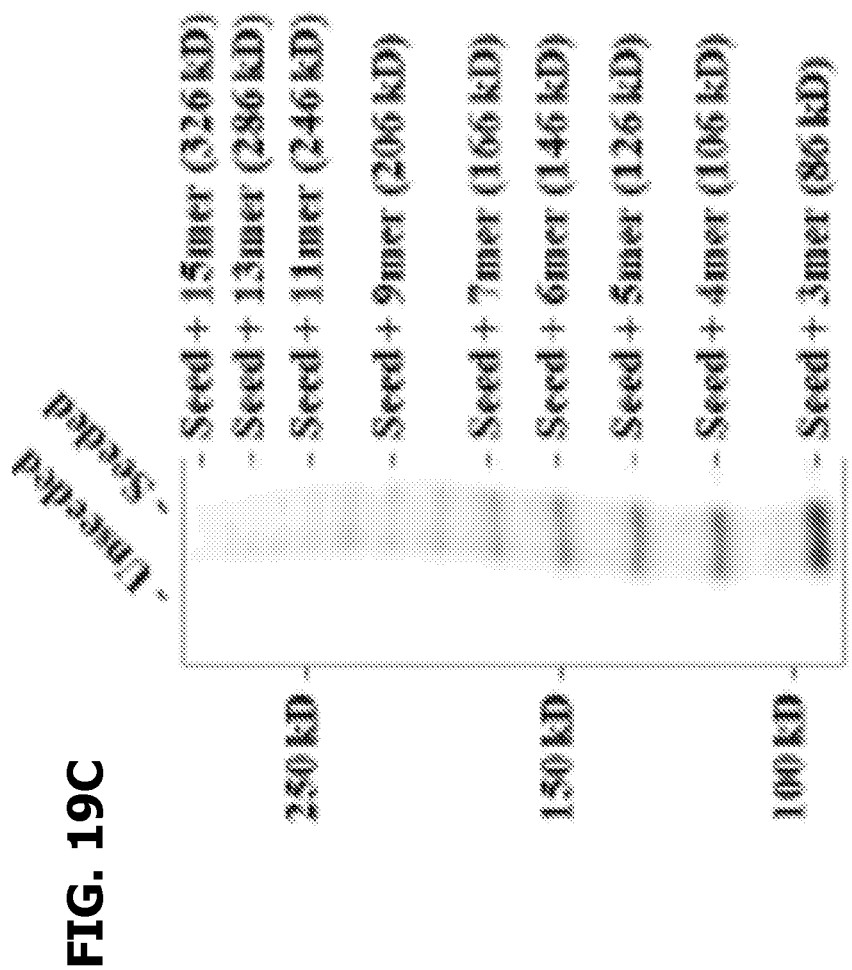

FIGS. 19A-19C show optimization of seed and monomer induction timing for production of linear high MW spidroins by SCP. (FIG. 19A) Western blots transferred from 15% SDS-PAGE gels of whole cell lysates taken from shake flask cultures at the indicated times post after IPTG induction. Cultures were induced at OD 2.0 in exponential growth phase with ATc at the indicated concentrations ranging from 50-175 nM. After 1 h post ATc induction, cultures were subsequently induced with 1 mM IPTG. Expected sizes of products are indicated in parentheses at far right. "7x" indicates monomer, "NTD" indicates seed, Subscript "$_c$" indicates cyclic products, "IntN" indicates the N-terminal SI, and subscript numbers indicate the number of reacted monomers within the product. (FIG. 19B) Western blot transferred from a 5% SDS-PAGE gel comparing products from unseeded polymerization (0 nm ATc, 1 mM IPTG for 7 h) to products from the optimized seeded conditions (125 nM ATc for 1 h followed by 1 mM IPTG for additional 6 h).

At the lowest ATc concentration (50 nM), seed protein was observed 1 h after ATc induction. However, as the monomer was continuously expressed, the seed protein was fully consumed by 3 h post ATc induction. Instead, cyclic monomer and dimer accumulated over the remainder of the time course, indicating insufficient seed production. At the highest tested ATc concentration (175 nM), IPTG induction of monomer cassette led to continuous accumulation of higher MW products over the entire time course and products exhibited apparent MWs consistent with the formation of linear NTD-(7x)$_n$-Int$^N$ polymers, indicating successful seeded chain-growth polymerization. However, excess seed protein also was observed under this ATc concentration throughout the time course. At intermediate ATc concentrations (100-125 nM), seed protein was mostly consumed by the end of the time course along with continuous production of HMW linear products and very little cyclic byproducts. Ultimately, the best tradeoff between high MW linear products, residual seed protein, and cyclic byproducts was observed with 125 nM ATc, which yielded linear products up to 326 kDa (FIG. 19C), roughly the size of the largest natural dragline spidroins.

Confirmation of Elimination of Cyclic Byproducts by SCP.

Figure 20B:
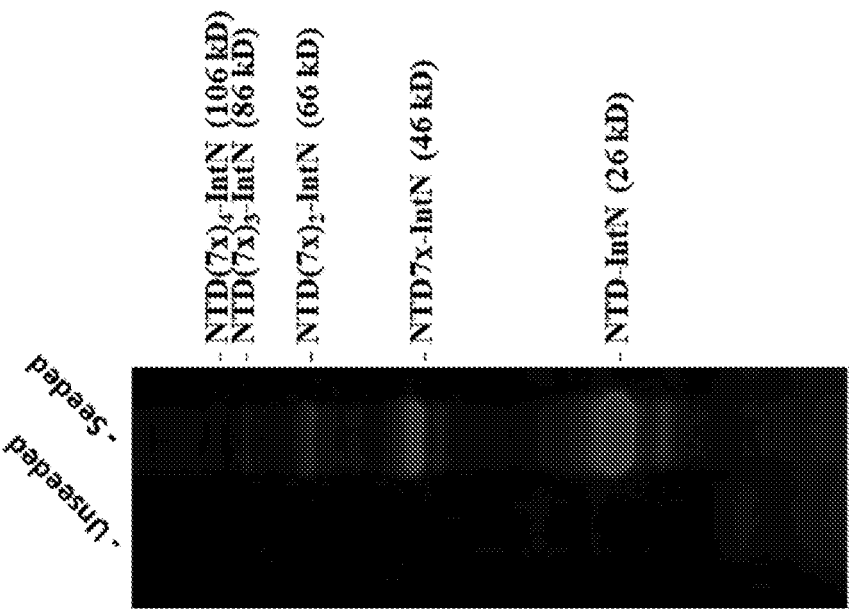
FIG. 20A and FIG. 20B are exemplary embodiments of SCP enabling production of primarily linear high MW silk proteins in accordance with the present disclosure.
Figure 20A:
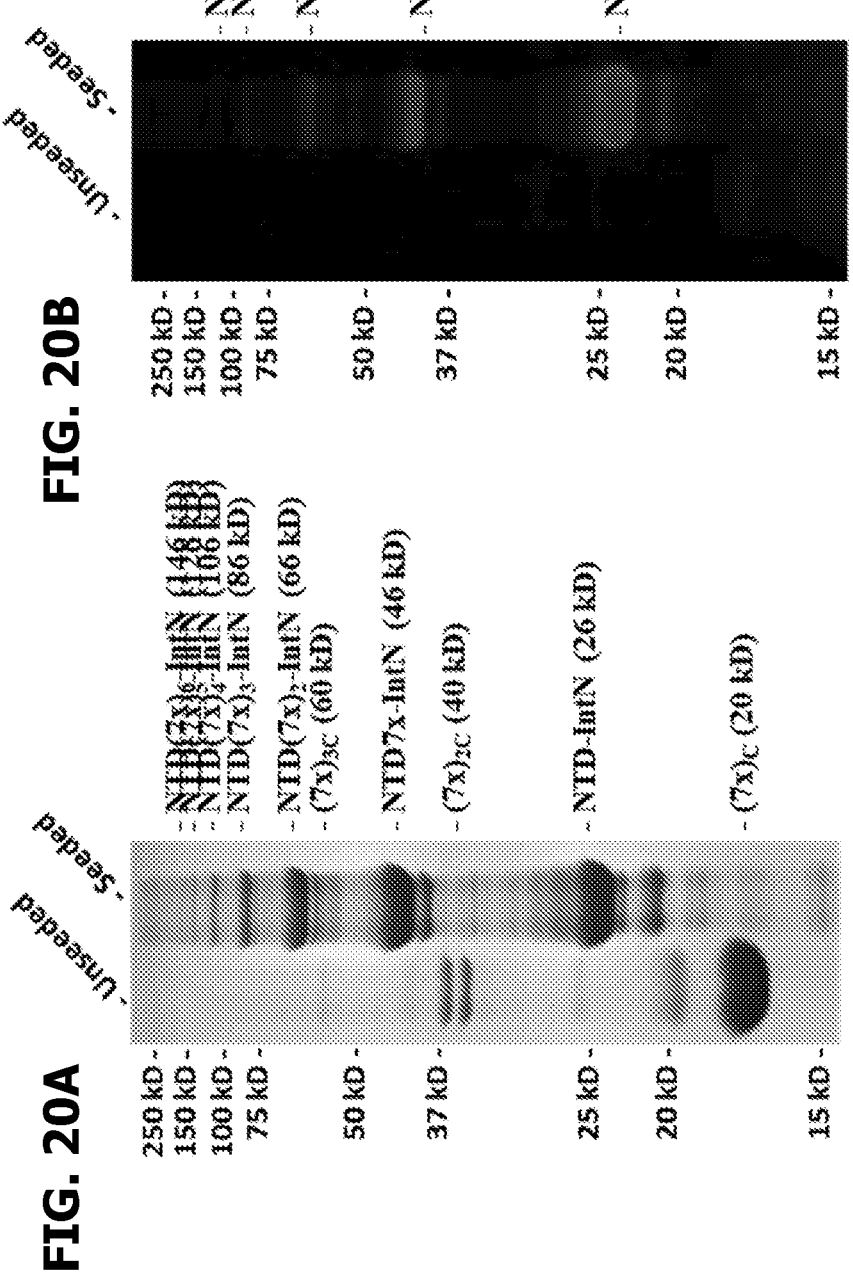

To definitively designate the observed polymerization products as being either cyclic or linear, a cysteine-specific fluorescent labeling reaction was employed. Neither NTD nor silk monomer contain any cysteine residues, while the Int$^N$ sequence contains three cysteine residues. Because all linear products contain an unreacted Int$^N$ at their C-termini, the linear products are fluorescently labeled at the cysteine sidechains, while cyclic products (which have lost both Int$^N$ and Int$^C$), are not. To label the polymerization products, overexpressed proteins were purified by nickel-affinity chromatography and reacted with a maleimide-Cy5 dye that specifically reacts with the thiol group of cysteine. Subsequent fluorescence imaging of products resolved by SDS-PAGE revealed specific labelling of linear products only formed when SCP was employed, while the unseeded polymerization produced cyclic products that exhibited no detectable fluorescent labeling (FIGS. 20A and 20B). These results further confirmed that SCP can eliminate cyclic products in favor of HMW linear spidroins.

FIGS. 20A and 20B show SCP enables production of primarily linear high MW silk proteins. (FIG. 20A) Coomassie Blue-stained SDS-PAGE gel (12% acrylamide) showing products of in vivo polymerization of a 7-mer dragline silk subunit polymerized with ("seeded") or without ("unseeded") application of the SCP method. Products are shown after purification by nickel-affinity chromatography. (FIG. 20B) Products were reacted with a sulfo-cy5 maleimide fluorescent probe to identify linear polymerization products given that cysteine residues are only present in the Int$^N$ domain. Expected MWs of products are indicated in parentheses. "7x" indicates monomer, "NTD" indicates seed, "C" indicates cyclic products, and numbers indicate the number of reacted monomers within the product.

MW Distribution of Spidroins Produced Via SCP.

To demonstrate the value of producing HMW linear spidroins via SCP, the in vivo SCP reaction in 1 L shake flask cultures was next performed. The over-produced high MW silk products were then separated from *E. coli* native proteins using nickel-affinity and ion-exchange chromatography (FIGS. 21A and 21B and FIGS. 22A and 22B).

Figures 21A, 21B:
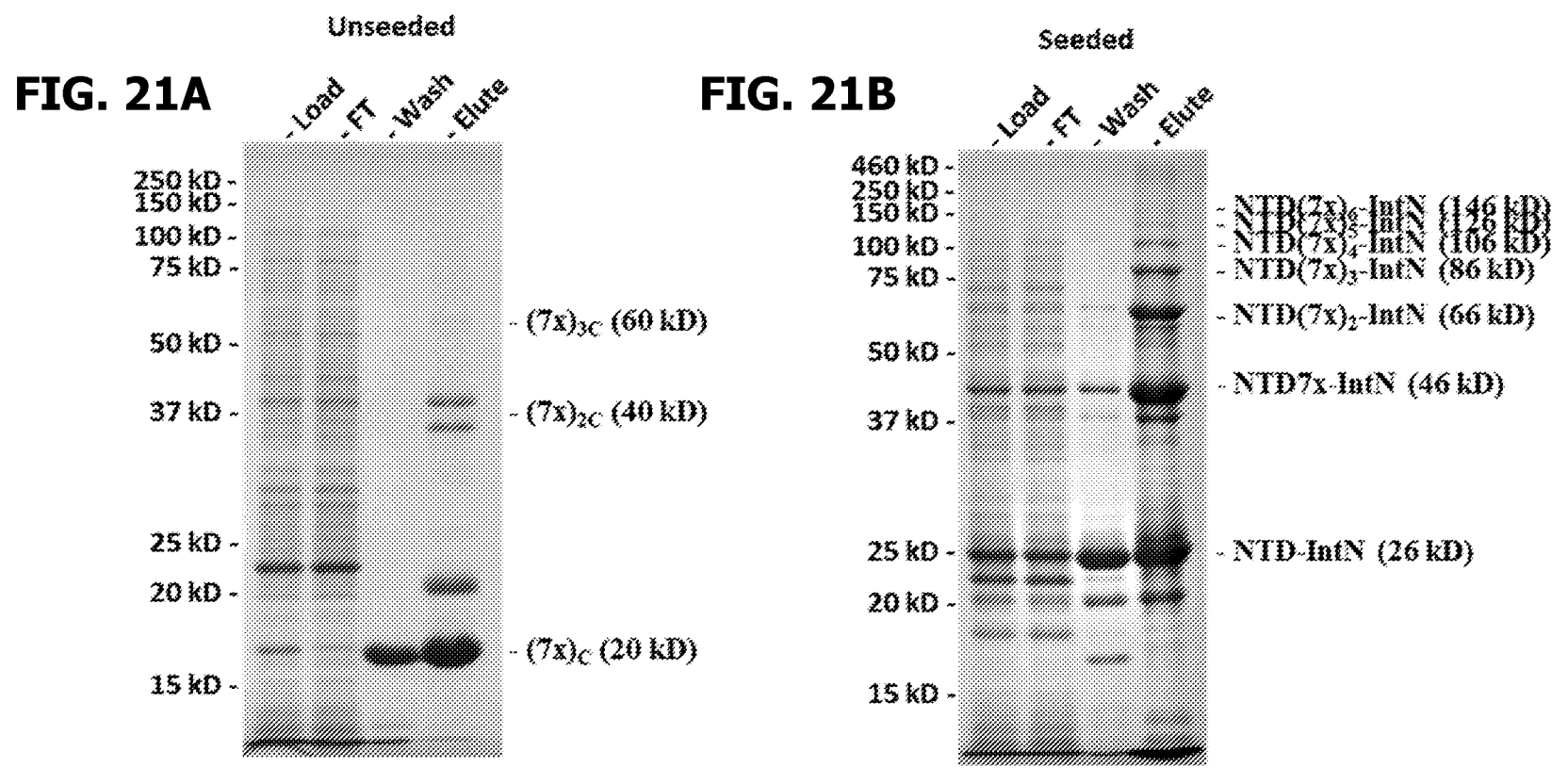

FIGS. 21A and 21B show Ni-Affinity purification of unseeded and seeded polymerization products. (FIG. 21A) Purification of unseeded polymerization products. (FIG. 21B) Purification of seeded polymerization products. "Load"—clarified cell lysate in 8M urea as loaded to His-trap column. "FT"—His-Trap column flow through. "Wash"—50 mM imidazole wash. "Elute"—300 mM imidazole elution. Expected sizes of products are indicated in parentheses at far right. "7x" indicates monomer, "NTD" indicates seed, Subscript "$_c$" indicates cyclic products, "IntN" indicates the N-terminal SI, and subscript numbers indicate the number of reacted monomers within the product.

Figures 22A, 22B:
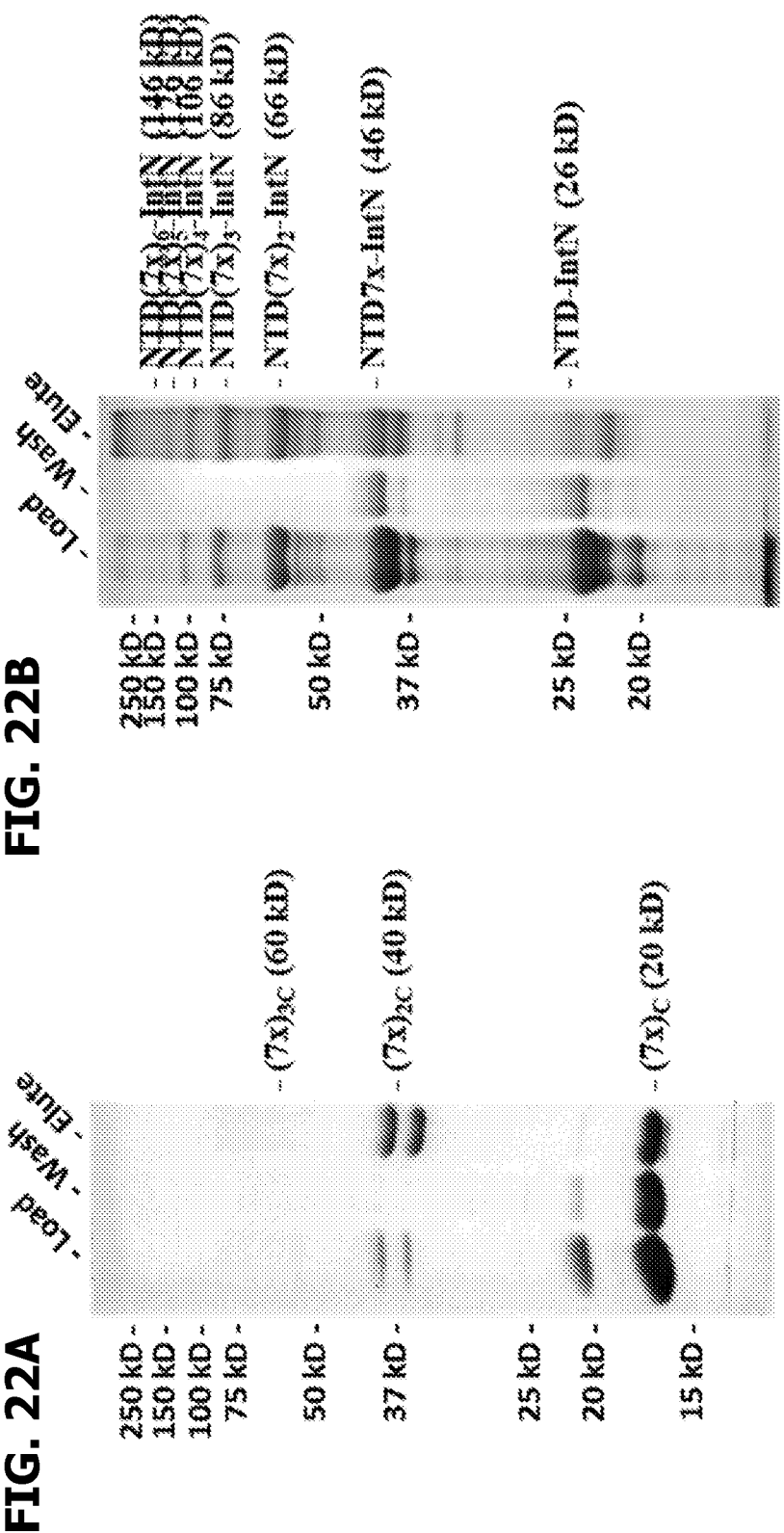
FIG. 22A and FIG. 22B are exemplary embodiments of cation exchange purification of unseeded and seeded polymerization products in accordance with the present disclosure.

FIGS. 22A and 22B. Cation exchange purification of unseeded and seeded polymerization products. (FIG. 22A) Purification of unseeded polymerization products. (FIG. 22B) Purification of seeded polymerization products. "Load"—Ni-affinity purified products as loaded to Hi-Trap SPFF column. "Wash"—40 mM guanidine wash. "Elute"—200 mM guanidine elution. Expected sizes of products are indicated in parentheses at far right. "7x" indicates monomer, "NTD" indicates seed, Subscript "$_c$" indicates cyclic products, "IntN" indicates the N-terminal SI, and subscript numbers indicate the number of reacted monomers within the product.

Figure 23:
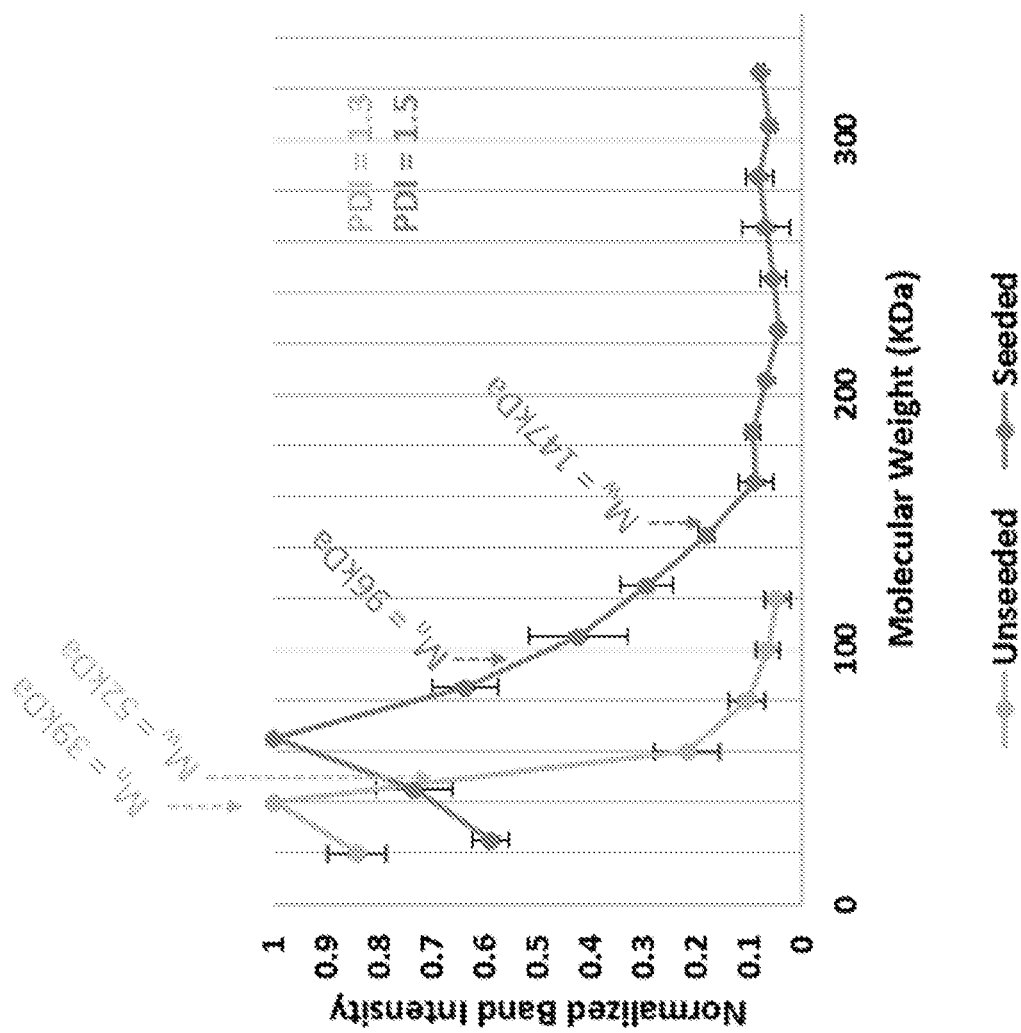
FIG. 23 is an exemplary embodiment of SCP increasing mass average MW of dragline spidroins in *E. coli* in accordance with the present disclosure.

Based on densitometry analysis of Coomassie-stained SDS-PAGE gels (see methods), the fully purified SCP products have a mass-average MW ($M_w$) of 147±6 KDa and a dispersity of 1.5, while the purified unseeded polymerization products exhibit $M_w$ of only 52±4 KDa and dispersity of 1.3 (FIG. 23). Both the MW and PDI values of the SCP products are typical of organic polymers produced through chain growth polymerization.

FIG. 23 shows SCP greatly increases mass average MW of dragline spidroins in *E. coli*. MW distributions as estimated from densitometry analysis of Coomassie-stained SDS-PAGE gels of seeded and unseeded polymerization products after purification by both Ni-affinity and ion exchange chromatography. Calculations of number-average MW ($M_n$), weight-average MW ($M_w$) and poly dispersity index (PDI) are described in methods.

Mechanical Properties of Wet Spun Fibers from Seeded Spidroins.

The purified HMW spidroins were then lyophilized, dissolved in hexafluoroisopropanol (HFIP) and spun into fibers following standard methods. Tensile tests were used to evaluate the mechanical performance of fibers. While fibers from the unseeded, cyclic spidroins displayed very weak mechanical performance, fibers from the SCP-produced spidroins displayed greatly enhanced fiber strength (245±63 MPa), modulus (4.1±1.1 GPa), and toughness (80±20 MJ/m$^3$), representing 24-, 41-, and 89-fold enhancements compared to those from unseeded spidroins, respectively (FIG. 24).

Figure 24:
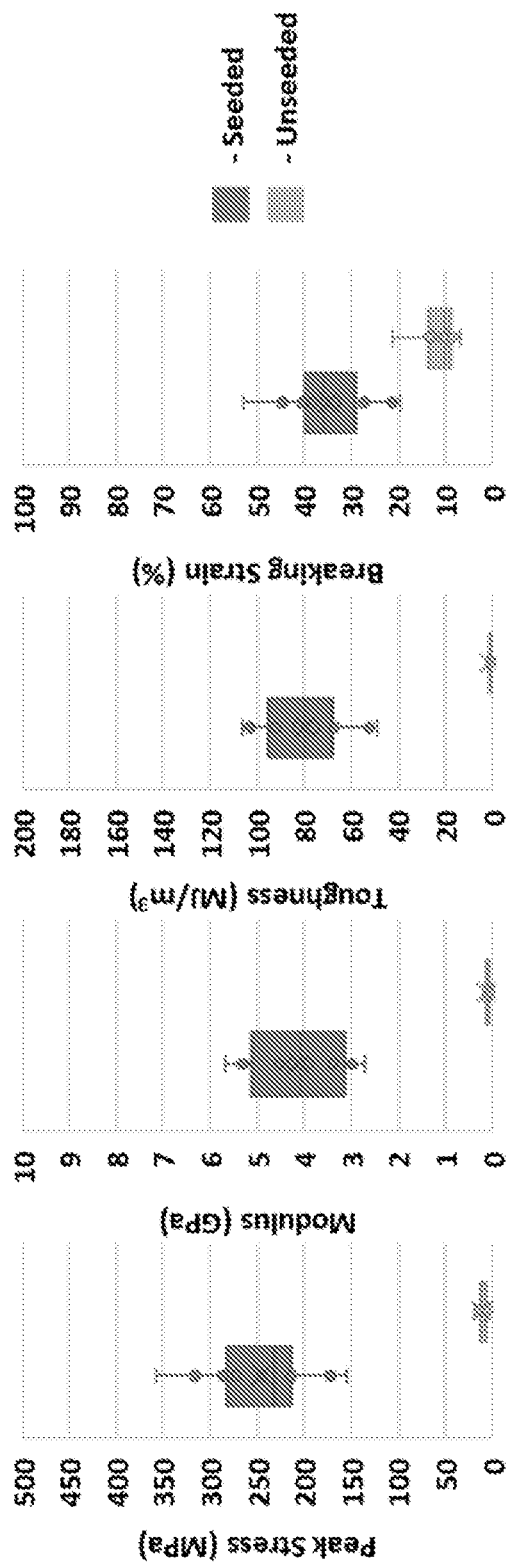
FIG. 24 is an exemplary embodiment of SCP enhancement of mechanical properties of resulting dragline fibers in accordance with the present disclosure.

FIG. 24 shows SCP greatly enhances mechanical properties of resulting dragline fibers. Mechanical properties of wet-spun fibers were assessed by standard tensile tests, indicating 24-, 41-, and 89-fold increases in strength, modulus, and toughness, respectively for fibers produced from seeded polymers relative to unseeded polymers.

Additionally, fibers produced from unseeded polymers are quite brittle, typically fracturing at approximately 10% elongation, while the fibers produced from seeded polymers exhibit substantial extensibility, with typical breaking strains >30%. The observed enhancements in mechanical properties are most likely the result of the drastically increased MW of SCP products. Indeed, a positive correlation between MW and strength/modulus of dragline spidroin fibers is well documented. It is also worth noting that the linear polymers produced herein contain a 6× histidine tag in each monomer unit and an Int$^N$ sequence at their C-termini. Yet despite the presence of these sequences, high strength, modulus, and toughness are still obtained, suggesting tolerance of dragline spidroin fibers to the presence of a few non-native sequences. Alternatively, it is also possible that mechanical properties be further improved by removal of these sequences and/or further purification to remove low MW species. Regardless, these results clearly demonstrate the value of SCP as a more scalable production of HMW dragline spidroins from relatively small, genetically stable sequences in a one-step fermentation process.

Spectroscopic Analysis of Fibers Produced from Seeded Polymers.

Next structural differences were examined between fibers produced by the two methods via Fourier transform infrared spectroscopy (FT-IR) and scanning electron microscopy (SEM). Interestingly, comparison of the FT-IR spectra of fibers spun from seeded and unseeded polymers showed relatively little difference in their general secondary structure and β-sheet content. Deconvolutions of the amide I bands of FT-IR spectra suggest that both fibers contain roughly 25-30% β-sheet content, which is similar to both natural spidroins and reported synthetic dragline spidroins (FIGS. 25A-25C).

FIGS. 25A-25D show secondary structure and morphology of fibers produced by SCP or unseeded method. Deconvolution of FT-IR amide I bands from fibers produced using seeded (FIG. 25A) or unseeded methods (FIG. 25B). Experimentally recorded and deconvoluted spectra were shown as solid and dotted black curves. (FIG. 25C) Average secondary structure percentages determined from the deconvolution of FT-IR spectra. (FIG. 25D) Representative SEM micrographs of fibers produced from seeded and unseeded spidroin polymers.

These results suggest that neither MW nor cyclization of dragline spidroin polymers have substantial effect on the β-sheet formation through the wet-spinning process and that differences in β-sheet content are not the main factor contributing to the observed differences in mechanical properties.

On the other hand, comparison of SEM micrographs of the fibers produced by the two methods reveal marked differences in microscale morphology, with fibers produced from unseeded polymers exhibiting relatively smooth and flat fracture surfaces, while fibers produced from seeded polymers exhibit a noticeably rougher and uneven fracture surface (FIG. 25D). The smooth, flat fracture surfaces of the fibers produced from unseeded spidroins is due to the very low MW of the constituent polymers. The entanglement MW ($M_e$) for fibroin from silkworm silk is roughly 50 kDa. Assuming a similar $M_e$ for dragline spidroins, the $M_w$ of the unseeded polymers is well under the critical MW for onset of entanglements ($M_c$=2$M_e$). Reports of crack propagation in semi-crystalline polymers have shown that crazing and chain pullout are generally not observed at $M_w$<$M_c$. Thus, it is likely that the fibers from unseeded spidroins fractured without crazing, allowing for rapid, direct crack propagation and leading to relatively smooth and flat fracture surface. Meanwhile, the $M_w$ of the seeded polymers is well above the $M_c$ for silk fibroins, such that crazing and chain pullout at the crack front are likely to occur during tensile tests, dissipating the stress over a larger fiber area and therefore increasing fracture toughness and resulting in the observed rougher, uneven fracture surfaces. Indeed, such relationships between MW and fracture surface morphologies have been reported for certain organic polymer fibers.

Overall, the results demonstrate that SCP enabled the production of linear spidroin polymers with MW up to at least 326 kDa, roughly the size of the largest natural dragline spidroins. SCP allows multiple rounds of SI-catalyzed ligation reactions to occur in living cells of one cell culture, significantly reducing the number of steps that in vitro ligation would otherwise require to obtain products with similar MW, thus greatly decreasing process complexity and increasing the potential scalability of fiber production. Furthermore, SCP permits production of high repetitive proteins from much smaller, more genetically stable and more easily expressed subunits, which can also facilitate practical production of PBMs for industrial applications. In the case of spidroin, although SCP yielded a mixture of products and the monomer sequence contains a 6× His-tag that may affect fiber properties, fibers spun from such a mixture exhibited high strength, modulus, and toughness, comparable to reported synthetic silk fibers with uniform size and similar MW. Continued optimization of SCP parameters such as monomer sequence and size, SI reaction rate, culture temperature, and induction timing may permit production of spidroins of even higher MW and yield with further improved mechanical properties. Finally, this approach may ultimately be applied to the production of numerous other highly repetitive, high MW PBMs to further advance their production for materials applications.

Materials and Methods

Strains and Growth Conditions.

For plasmid cloning and protein production, *E. coli* NEB 10-beta (NEB10β) was used (Table 10). Strains were cultured in Terrific Broth (TB) containing 24 g/L yeast extract, 20 g/L tryptone, 0.4% v/v glycerol, 17 mM $KH_2PO_4$, and 72 mM $K_2HPO_4$ at 37° C. with appropriate antibiotics (50 μg/mL kanamycin and/or 30 μg/mL chloramphenicol).

TABLE 10

Strains.

| Strain Name | Genotype | Strain Source |
|---|---|---|
| NEB10β | F' proA + B + lacIq Δ(lacZ)M15 zzf::Tn10 (TetR) Δ(ara-leu) 7697 araD139 fhuA ΔlacX74 galK16 galE15 e14- Φ80dlacZΔM15 recA1 relA1 endA1 nupGrpsL (StrR) rph spoT1 Δ(mrr-hsdRMS-mcrBC) | NEB |
| s10x | NEB10β containing p10x | Present study |
| sSCP | NEB10β containing p7x + pNTD | Present study |

Chemicals and Reagents.

Unless otherwise noted, reagents were obtained from MilliporeSigma. Plasmid purification and gel extraction kits were obtained from iNtRON Biotechnology. FastDigest restriction enzymes and T4 DNA ligase were purchased from Thermo Fisher Scientific and used for all digestions and ligations following the manufacturer's suggested protocols.

Genetic Assembly of Monomer and Seed Cassettes.

To construct the 10x and 7x monomer cassettes, 10 or 7 repeats of the *N. clavipes* MaSp1 dragline spidroin (Table 11) were computationally designed, flanked at the 5' end by KpnI and at the 3' end by Kpn2I, and sequence optimized as described herein elsewhere. Optimized sequences were chemically synthesized by Integrated DNA Technologies. The synthesized sequences were separately inserted between restriction sites KpnI/Kpn2I of a medium copy (pBBR1 replication origin), chloramphenicol resistance ($Cm^R$) SI-Bricks expression vector containing optimized gp41-1 SI coding sequences (Table 11), resulting in plasmids pB6c-$Int^C$-10x-$Int^N$ (p10x) and pB6c-$Int^C$-7x-$Int^N$ (p7x) (Table 12).

TABLE 11

Amino acid sequences of proteins

| Name | Sequence |
|---|---|
| Gp41-1 $Int^C$ | MAKTKMLKKILKIEELDERELIDIEVSGNHLFYANDILTH N (SEQ NO ID: 10) |
| Gp41-1 $Int^N$ | CLDLKTQVQTPQGMKEISNIQVGDLVLSNTGYNEVLNVFP KSKKKSYKITLEDGKEIICSEEHLFPTQTGEMNISGGLKE GMCLYVKE* (SEQ NO ID: 11) |
| 10x MaSp1 Monomer | SSSDVGTHHHHHHAAAAAGGAGQGGYGGLGSQGAGRGGLG GQGAGAAAAGGAGQGGYGGLGSQGAGRGGLGGQGAGAAA AAGGAGQGGYGGLGSQGAGRGGLGGQGAGAAAAGGAGQG GYGGLGSQGAGRGGLGGQGAGAAAAGGAGQGGYGGLGSQ GAGRGGLGGQGAGAAAAGGAGQGGYGGLGSQGAGRGGLG GQGAGAAAAGGAGQGGYGGLGSQGAGRGGLGGQGAGAAA AAGGAGQGGYGGLGSQGAGRGGLGGQGAGAAAAGGAGQG GYGGLGSQGAGRGGLGGQGAGAAAAASGTRSGY (SEQ NO ID: 12) |
| 7x MaSp1 Monomer | SSSDVGTHHHHHHGGGGSAGRGGLGGQGAGAAAAGGAGQ GGYGGLGSQGAGRGGLGGQGAGAAAAGGAGQGGYGGLGS QGAGRGGLGGQGAGAAAAGGAGQGGYGGLGSQGAGRGGL GGQGAGAAAAGGAGQGGYGGLGSQGAGRGGLGGQGAGAA AAAGGAGQGGYGGLGSQGAGRGGLGGQGAGAAAAGGAGQ GGYGGLGSQGAGRGGLGGQGAGAAAAGGAGQGGYGGLGS QGSGTRSGY (SEQ NO ID: 13) |

TABLE 11-continued

Amino acid sequences of proteins

| Name | Sequence |
|---|---|
| NTD | MAKTKQNTPWSSTELADAFINAFMNEAGRTGAFTADQLDD MSTIGDTIKTAMDKMARSNKSSKGKLQALNMAFASSMAEI AAVEQGGLSVDAKTNAIADSLNSAFYQTTGAANPQFVNEI RSLINMFAQSSANEVSYGGSGTRSGY (SEQ NO ID: 14) |

TABLE 12

Plasmids

| Plasmid Name | ORI | Promoter | Resistance | Gene | Plasmid Source |
|---|---|---|---|---|---|
| pB6c | pBBR1 | $P_{LlacO1}$ | $Cm^R$ | — | Lee et al. 2011 |
| pA2k | p15A | $P_{Tet}$ | $Kan^R$ | — | Lee et al. 2011 |
| p10x | pBBR1 | $P_{LlacO1}$ | $Cm^R$ | SI-flanked 10-mer N. clavipes dragline spidroin | Present study |
| p7x | pBBR1 | $P_{LlacO1}$ | $Cm^R$ | SI-flanked 7-mer N. clavipes dragline spidroin | Present study |
| pNTD | p15A | $P_{Tet}$ | $Kan^R$ | Native N. clavipes N-terminal domain +3' Gp41-$1^N$ | Present study |

To construct the seed cassette, the amino acid sequence of the NTD of *N. clavipes* dragline spidroin MaSp1 was computationally redesigned for *E. coli* expression and chemically synthesized by Integrated DNA Technologies. The seed sequence was inserted between restriction sites BglII/Kpn2I of a medium copy (p15A replication origin), kanamycin resistance ($Kan^R$) SI-Bricks expression vector containing optimized gp41-1 $Int^N$, resulting in plasmid pA2k-NTD-$Int^N$ (pNTD) (Table 12).

SCP Optimization.

For SCP optimization, cultures were grown in 50 mL volumes of TB medium in 250 mL shake flasks with orbital shaking. Cultures were initially incubated at 37° C. until reaching an $OD_{600}$=2.0. Cultures were then induced with varied concentrations of ATc and incubated at 30° C. After one hour, monomer production was induced by addition of 1 mM IPTG, and cultures were incubated at 30° C. for varied time period.

Shake Flask Cultures.

Protein production was performed in 2 L shake flasks. Transformants were cultured overnight in 50 mL TB medium at 37° C. on an orbital shaker. Overnight 50 mL cultures were then used to inoculate 500 mL fresh TB medium in 2 L Erlenmeyer flasks at an initial $OD_{600}$=0.08. Cultures were grown at 37° C. with orbital shaking to $OD_{600}$=2. In the case of unseeded polymer production, cultures were induced by addition of 1 mM IPTG and cultured for an additional 6 hours at 30° C. with orbital shaking. In the case of SCP, seed production was first induced by addition of 125 nM ATc, cultured for one hour at 30° C., followed by monomer induction with 1 mM IPTG and continued culture for additional 6 hours at 30° C.

Protein Purification.

Cell pellets were directly solubilized in lysis buffer (8M urea, 20 mM potassium phosphate, 10 mM imidazole, pH 7.4). The mixture was stirred overnight at 22° C. and centrifuged at 25,000×g for 20 min. The pellet was discarded and the supernatant was sonicated for a total of 10 min. (70% amplitude, 5 s. on, 10 s. off). The sonicated supernatant was then centrifuged at 40,000×g for 30 min. The pellet was discarded, and the supernatant was filtered through a 0.2 µm filter. The filtered solution was applied to a 5 mL His-Trap column at a flow rate of 1 mL/min. The column was then washed with 5 CV of wash buffer (lysis buffer+50 mM imidazole) followed by elution with 5 CV of elution buffer (lysis buffer+300 mM imidazole). Eluent was then dialyzed against cation exchange (IEX) binding buffer (8M urea, 10 mM HEPES, pH 8.0) in 10K MWCO SnakeSkin dialysis tubings (ThermoFisher Scientific). The eluent was loaded to a 5 mL HiTrap SPFF cation exchange column at a flow rate of 1 mL/min. The column was then washed with 5 CV of IEX wash buffer (binding buffer+40 mM guanidinium hydrochloride). Bound proteins were eluted with 5 CV IEX elution buffer (binding buffer+200 mM guanidinium hydrochloride). IEX eluent was then dialyzed extensively against 5% acetic acid at 4° C. in 10K MWCO SnakeSkin dialysis tubings, and lyophilized.

Fluorescence Labelling.

After purification by His-Trap affinity chromatography, purified products were dialyzed into 8 M urea, 10 mM HEPES pH 7.4, and 100 µM TCEP, at a final protein concentration of approximately 10 µM. Sulfo-Cyanine5 (Lumiprobe Life science solutions) was pre-dissolved in DMSO at a concentration of 100 mM and then added to the protein solution to a final concentration of 200 µM. The reaction mixture was incubated overnight at 4° C. in dark with periodic mixing. After overnight incubation, the reaction was mixed 1:1 with 2× Laemmli sample buffer, run on a SDS-PAGE (see below) and imaged with an Azure c600 Imager (Azure Biosystems) in the Cy5 channel.

SDS-PAGE.

All SDS-PAGE gels were 1 mm thick, discontinuous with 3% stacking gel, and hand cast at the indicated percentages. Samples were prepared at 1 mg/mL or 5 µM total protein in Laemmli sample buffer (2% SDS, 10% glycerol, 60 mM Tris pH 6.8, 0.01% bromophenol blue, 100 µM DTT). Gels were run on Mini-PROTEAN Tetra Cells (Bio-Rad) in 1× Tris-glycine SDS buffer (25 mM Tris base, 250 mM glycine, 0.1% w/v SDS), until just before the dye front exited the gel. Gels were stained in Coomassie Blue solution (50% methanol, 10% w/v acetic acid, 1 g/L Coomassie Brilliant Blue) for a minimum of one hour at room temperature with gentle agitation and destained in Coomassie Blue destain buffer (40% v/v methanol, 10% v/v acetic acid) for a minimum of one hour. Gels were imaged on an Azure c600 Imager (Azure Biosystems).

Western Blotting.

Western blotting was performed with an OWL HEP-3 semi-dry electroblotting system (Thermo Scientific). SDS-PAGE gels, blotting paper (10 cm thickness, Bio-Rad), and blotting membrane (PVDF, 0.2 µm pore size, Roche) were soaked for 15 minutes in semi-dry transfer buffer (1× Tris-glycine SDS buffer+20% methanol). After soaking blot sandwiches were stacked onto the OWL system and proteins were transferred at 20 mA constant current for 1 h. Blots were then washed briefly in 1×TBS Tween (50 mM Tris-Cl pH 7.6, 150 mM NaCl, 0.1% Tween 20) and then blocked in 1×TBS Tween+5% dried milk powder for 2 h with gentle rocking at room temperature. Blots were then soaked overnight at 4 C with gentle rocking in 1×TBS Tween+2% dried milk and 1:5000 dilution of mouse anti $H_6$ monoclonal antibody (ThermoFisher). Blots were washed 4× in TBS Tween and then incubated for 45 min. with gentle rocking at room temperature in 1×TBS-Tween+2% dried milk and 1:10000 dilution of goat anti mouse AzureSpectra 700 antibody (Azure Biosystems). Finally, blots were washed 4× in TBS-Tween and imaged on an Azure c600 Imager (Azure Biosystems) in the IR700 imaging channel.

Densitometry Analysis and Calculation of $M_w$, $M_n$, and PDI.

Figure 26:
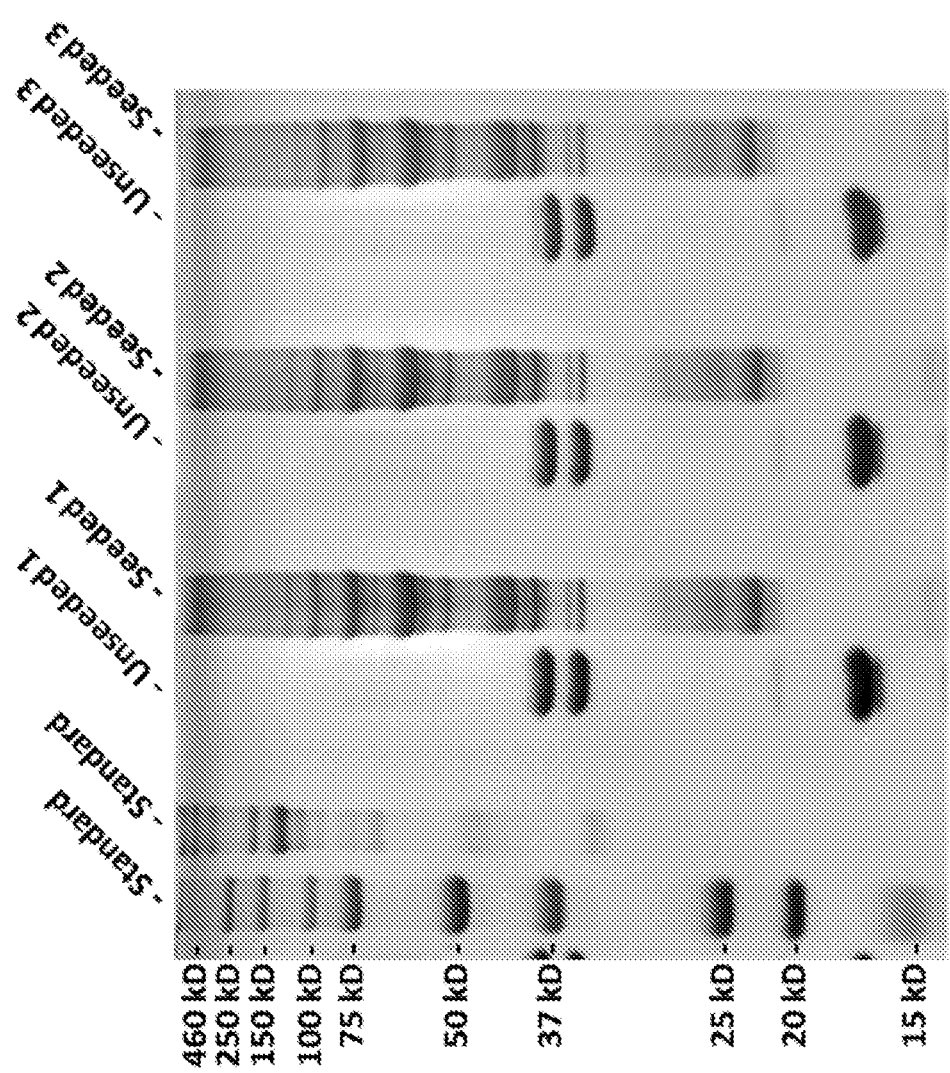
FIG. 26 is an exemplary embodiment of Coomassie stained SDS-PAGE gel used for densitometry analysis of MW distribution in accordance with the present disclosure.

Coomassie stained SDS-PAGE gels of polymerization products after ion exchange purification were imaged on an Azure c600 Imager (Azure Biosystems) (FIG. 26).

FIG. 26 shows Coomassie stained SDS-PAGE gel used for densitometry analysis of MW distribution. All quantifications were performed in triplicate. All densitometry analysis was performed with the AzureSpot Analysis Software (Azure Biosystems). Images were background subtracted with a built-in automatic lane edge subtraction algorithm. Protein band intensities were integrated by the AzureSpot software, and apparent MWs were calculated based on MW standards run on the same gels. Integrated band intensities were normalized against the highest band intensity in a given MW distribution. Averages of three normalized integrated band intensities along with the standard deviation of the three normalized values were plotted against MW. Number-average MW ($M_n$) was calculated as $$M_n = \frac{\Sigma M_i N_i}{\Sigma N_i},$$

where $\Sigma M_i N_i$ is treated as the sum of each species' MW ($M_i$) multiplied by its integrated band intensity ($N_i$), and $\Sigma N_i$ is the sum of all band intensities. Weight-average MW ($M_w$) was calculated as $M_w = \Sigma w_i M_i$, where $w_i$ is the weight fraction of each species calculated as the total weight of a species ($M_i N_i$) divided by the total weight of all species $\Sigma M_i N_i$. Lastly, PDI was calculated as the ratio of $M_w$ to $M_n$.

Fiber Spinning and Mechanical Testing.

Fiber spinning and mechanical testing were performed following a protocol modified from known methods. Lyophilized spidroin powders were dissolved in HFIP to 20% w/v. This protein dope was loaded to a 100 µL Hamilton gastight syringe (Hamilton Robotics). The syringe was fitted to a Harvard Apparatus Pump 11 Elite syringe pump (Harvard Apparatus), and the dope was extruded into a 95% v/v methanol bath at 5 µL/min. Extruded fibers were then transferred to a 75% v/v methanol bath and carefully extended at approximately 1 cm/s to the maximum draw ratio without fiber fracture. Extended fibers were removed from the bath and held under tension until visibly dry. Segments of post-drawn fibers (20 mm) were carefully laid exactly vertical across a 5 mm (vertical)×15 mm (horizontal) opening cut into a 20 mm×20 mm piece of cardstock and fixed with adhesive tape at both ends of the opening. Diameters of mounted fibers were then measured by light microscopy, averaging measurements at three points along the fiber axis (Table 13 and Table 14).

TABLE 13

Diameter measurements and mechanical properties for un-seeded fibers

| FIBER | Diam. A (µm) | Diam. B (µm) | Diam. C (µm) | Avg. Diameter (µm) | σ (MPa) | E (GPa) | ε (%) | $U_T$ (MJ/m³) |
|---|---|---|---|---|---|---|---|---|
| 1 | 14.59 | 14.45 | 15.79 | 14.94 | 154.2 | 2.983 | 38.137 | 52 |
| 2 | 14.58 | 13.79 | 14.43 | 14.27 | 171.8 | 3.381 | 33.429 | 49 |
| 3 | 13.78 | 12.34 | 12.66 | 12.93 | 213.1 | 4.536 | 35.892 | 67 |

TABLE 13-continued

Diameter measurements and mechanical properties for un-seeded fibers

| FIBER | Diam. A (μm) | Diam. B (μm) | Diam. C (μm) | Avg. Diameter (μm) | σ (MPa) | E (GPa) | ε (%) | $U_T$ (MJ/m³) |
|---|---|---|---|---|---|---|---|---|
| 4 | 14.15 | 15.44 | 13.44 | 14.34 | 356.5 | 5.672 | 19.486 | 106 |
| 5 | 14.90 | 16.03 | 16.35 | 15.76 | 316.6 | 5.463 | 35.577 | 96 |
| 6 | 16.25 | 18.04 | 17.64 | 17.31 | 272.4 | 4.256 | 40.319 | 92 |
| 7 | 16.06 | 15.35 | 14.63 | 15.35 | 286.3 | 5.298 | 27.417 | 71 |
| 8 | 17.34 | 18.05 | 17.34 | 17.58 | 245.1 | 3.905 | 21.157 | 76 |
| 9 | 19.71 | 18.27 | 17.95 | 18.64 | 217 | 3.024 | 44.747 | 83 |
| 10 | 19.09 | 21.32 | 19.12 | 19.84 | 217.2 | 2.693 | 52.923 | 103 |

TABLE 14

Diameter measurements and mechanical properties for seeded fibers

| FIBER | Diam. A (μm) | Diam. B (μm) | Diam. C (μm) | Avg. Diameter (μm) | σ (MPa) | E (GPa) | ε (%) | $U_T$ (MJ/m³) |
|---|---|---|---|---|---|---|---|---|
| 1 | 58.81 | 59.18 | 61.71 | 59.90 | 3.8 | 0.052 | 6.9 | 0.22 |
| 2 | 75.36 | 73.38 | 76.63 | 75.12 | 4.1 | 0.05 | 8.6 | 0.26 |
| 3 | 67.48 | 67.32 | 68.82 | 67.87 | 10.2 | 0.115 | 9.3 | 0.66 |
| 4 | 65.10 | 59.14 | 63.71 | 62.65 | 14.5 | 0.196 | 10.5 | 1.78 |
| 5 | 77.18 | 82.25 | 82.81 | 80.75 | 6.4 | 0.048 | 13.8 | 0.54 |
| 6 | 51.83 | 55.59 | 53.85 | 53.76 | 6.8 | 0.038 | 21.0 | 0.88 |
| 7 | 59.73 | 60.10 | 60.85 | 60.23 | 13.6 | 0.167 | 8.5 | 1.07 |
| 8 | 47.56 | 47.63 | 47.45 | 47.55 | 19.8 | 0.139 | 14.2 | 1.70 |
| 9 | 55.13 | 51.77 | 51.62 | 52.84 | 10.5 | 0.086 | 13.5 | 1.05 |
| 10 | 57.79 | 57.29 | 57.25 | 57.44 | 11.4 | 0.122 | 9.7 | 0.82 |

Mechanical properties were measured by axial pull tests on an MTS Criterion Model 41 universal test frame fitted with a 1 N load cell (MTS Systems Corporation). Cardstock holders were mounted between two opposing spring-loaded grips, and the supporting edges were carefully cut. Pull tests were conducted at a relative humidity of 30% and temperature of 22° C., with a constant crosshead speed of 10 mm/min. Stress-strain curves were recorded by the MTS TW Elite test suite at a sampling rate of 50 Hz. Fiber breaks were recorded when a 90% drop from peak stress was detected. All mechanical properties were automatically calculated by the MTS TW Elite test suite. Ultimate tensile strength was calculated as the maximum measured load over the initial fiber cross-sectional area ($A=\pi r^2$), as determined from measured initial diameters. Modulus was calculated as the slope of a linear least squares fit to the stress/strain data of the initial elastic region. Toughness was calculated as the area under the total stress/strain curve divided by the initial fiber volume ($V=\pi r^2 h$) as calculated from measured initial fiber diameters and set initial gage length of 5 mm. For each protein, a total of 10 fibers were measured in this manner.

Light Microscopy.

Fiber diameters were measured using images acquired with a Zeiss Axio Observer ZI Inverted Microscope equipped with a phase contrast 20× objective lens and the Axiovision LE software (Zeiss).

Scanning Electron Microscopy.

Following tensile tests, silk fibers were mounted onto a sample holder using conductive tape. The sample holder was sputter coated with a 10 nm gold layer using a Leica EM ACE600 high vacuum sputter coater (Leica Microsystems). Fibers were imaged using a Nova NanoSEM 230 Field Emission Scanning Electron Microscope (Field Electron and Ion Company, FEI) at an accelerating voltage of 7-10 kV.

Fourier Transform Infrared Spectroscopy.

For secondary structure determination, FTIR spectra were acquired with a Thermo Nicolet 470 FT-IR spectrometer (ThermoFisher Scientific) fitted with a Smart Performer ATR accessory with Ge crystal. Spectra were acquired from 1350-1750 cm$^{-1}$ at 4 cm$^{-1}$ resolution. A total of 254 scans were accumulated for each sample. All recorded spectra were analyzed using Fityk 0.9.8. Baselines were subtracted from all spectra using the built-in Fityk convex hull algorithm. The amide I band (1600-1700 cm$^{-1}$) was deconvolved into a set of eleven Lorentzian peaks centered at 1610, 1618.5, 1624.5, 1632.5, 1642, 1651, 1659, 1666.5, 1678, 1690.5, and 1700 cm$^{-1}$ corresponding to amide I shifts characteristic of either β-sheet, random coil, α-helix, or β-turn. Specific assignments are listed in Table 15. Peak areas were integrated and percentages were calculated as the component peak area over the sum of all peak areas. Percentages were averaged from measurements of three fibers each for unseeded and seeded polymers.

TABLE 15

Amide I secondary structure assignments.

| Wavenumber (cm$^{-1}$) | Secondary structure |
|---|---|
| 1,605-1,615 | Side chains/aggregated strands |
| 1,616-1,621 | β-strands/sheets (weak) |
| 1,622-1,627 | β-sheets (strong) |
| 1,628-1,637 | β-sheets (strong) |
| 1,638-1,646 | Random coil |
| 1,647-1,655 | Random coil |
| 1,656-1,662 | α-helix |
| 1,663-1,670 | Turn |
| 1,671-1,685 | Turn |
| 1,686-1,695 | Turn |
| 1,697-1,703 | β-sheets (weak) |

Seeded Chain-Growth Polymerization of Proteins in Living Bacterial Cells

Microbially produced protein-based materials (PBMs) are appealing due to use of renewable feedstock, low energy requirements, tunable side-chain chemistry, and biodegradability. However, high-strength PBMs typically have high molecular weights (HMW) and repetitive sequences that are difficult to microbially produce due to genetic instability and metabolic burden. The development of a biosynthetic strategy is reported herein, termed seeded chain-growth polymerization (SCP) for synthesis of HMW PBMs in living bacterial cells. SCP uses split intein (SI) chemistry to co-translationally polymerize relatively small, genetically stable material protein subunits, effectively preventing intramolecular cyclization. SCP was applied to bioproduction of spider silk in *Escherichia coli*, generating HMW spider silk proteins (spidroins) up to 300 kDa, resulting in spidroin fibers of high strength, modulus, and toughness. SCP provides a modular strategy to synthesize HMW, repetitive material proteins and may facilitate bioproduction of a variety of high-performance PBMs for broad applications.

Microbial biopolymers are attractive alternatives to traditional petroleum-based polymers due to use of renewable feedstock and environmentally friendly production/processing. Protein-based materials (PBMs) are especially appealing biopolymers because they can fold into a diversity of structures with versatile functions and properties. Spider silks, for example, can exhibit tensile strength and toughness superior to steel and are used by spiders for prey capture/ storage, egg protection, adhesion, and even flight.

As with organic polymers, mechanical properties of PBMs are typically dependent on the molecular weight (MW) of constituent proteins. In general, higher MW promotes more extensive intermolecular interactions and reduces chain-end density, thereby decreasing probability of chain slippage and fracture and increasing material strength. Consequently, high performance PBMs (e.g. silks, keratin, elastin, suckerin, and mussel foot protein) are often composed of high MW (HMW), repetitive protein sequences or protein complexes, where HMW is critical to mechanical performance.

Engineered microbial synthesis of HMW PBMs is extremely challenging due primarily to genetic instability of repetitive coding sequences and low translation efficiency of complex mRNA secondary structures. While creative strategies have been developed to enhance microbial production of HMW PBMs (e.g. extensive optimization of codon usage, metabolic engineering of aminoacyl-tRNA supplies, or protein cross-linking and complexation), the core challenge of genetic instability in HMW PBM production remains largely unaddressed.

To help bypass these challenges, an engineered microbial synthesis termed Seeded Chain-growth Polymerization (SCP) was developed involving co-translational, split intein (SI) catalyzed polymerization of relatively small, genetically stable material proteins in living microbes. While a handful of biochemical tools are available for in vivo post-translational protein cross-linking (e.g. SpyTag-SpyCatcher, Sortase A, disulfide linkage), these tools have been used primarily for one-step reactions, and no method is available for controlled linear polymerization of proteins into HMW polymers in living cells. Alternatively, SIs are well suited for microbial production of HMW PBMs because they allow for in vivo self-cleavage of the catalytic domain from the resulting ligated protein polymer, resulting in linear, backbone peptide bond formation, thereby minimizing modification to the resulting PBM's sequence and structure, which might otherwise negatively affect the resulting material's properties.

In some embodiments, the present disclosure is directed to a method for synthesizing a spidroin. The method comprises synthesizing a seed protein in vivo in a heterologous host, the seed protein comprising a C-terminus $Int^N$ domain, synthesizing a monomer in vivo in the heterologous host, the monomer comprising an N-terminus $Int^C$ domain and a C-terminus $Int^N$ domain, and co-translationally polymerizing the monomer via in vivo split-intein mediated polymerization.

In some embodiments the heterologous host is a protein-expressing microbial host and/or the monomer is a silk amino acid sequence from a spider species. In some embodiments, the heterologous host is E. coli, and/or the monomer is an N. clavipes spidroin. In some embodiments, the synthesized spidroin has a molecular weight of at least about 300 kDa, at least about 400 kDA, at least about 500 kDa, or at least about 600 kDa. In some embodiments the method further comprises spinning the synthesized spidroin into fibers. In some embodiments, the fibers have a tensile strength of from about 150 MPa to about 350 MPa, or from about 170 MPa to about 310 MPa. In some embodiments, the fibers have a modulus of about 3.0 GPa to about 5.5 GPa. In some embodiments, the fibers have a toughness of from about 25 MJ/m$^3$ to about 150 MJ/m$^3$, or from about 55 MJ/m$^3$ to about 105 MJ/m$^3$. In some embodiments, the fibers have a β-sheet content of from about 20% to about 60%, or from about 35% to about 45%. In some embodiments, the fibers have an extensibility of from about 5% to about 35%, or from about 10% to about 25%.

In some embodiments, a method for synthesizing a spidroin comprises: synthesizing a seed protein in vivo in a heterologous host, the seed protein comprising a C-terminus $Int^N$ domain; synthesizing a monomer in vivo in the heterologous host, the monomer comprising both an N-terminus $Int^C$ domain and a C-terminus $Int^N$ domain; and undergoing multiple steps of co-translational ligation of the monomer via in vivo split-intein mediated reaction. In some embodiments, the heterologous host is E. coli, or other protein expressing microbial hosts. In some embodiments, the monomer contains a fragment of silk amino acid sequence from N. clavipes spidroin or other spider species. In some embodiments, the synthesized spidroin is a linear polymer. In some embodiments, the synthesized spidroin has a molecular weight of at least about 300 kDa. In some embodiments, the method further comprises spinning the synthesized spidroin into fibers. In some embodiments, the fibers have a tensile strength of from about 170 MPa to about 310 MPa, or at least about 300 MPa. In some embodiments, the fibers have a toughness of from about 55 MJ/m$^3$ to about 105 MJ/m$^3$, or at least about 100 MJ/m$^3$.

In some embodiments, the present disclosure is directed to a system for synthesizing a spidroin in vivo. The system comprises a host cell, a seed cassette encoding a seed protein comprising a C-terminus $Int^N$ domain, and a monomer cassette encoding a monomer comprising an N-terminus $Int^C$ domain and a C-terminus $Int^N$ domain.

In some embodiments the heterologous host is a protein-expressing microbial host and/or the monomer is a silk amino acid sequence from a spider species. In some embodiments, the heterologous host is E. coli, and/or the monomer is an N. clavipes spidroin. In some embodiments, the fibers have a tensile strength of from about 150 MPa to about 350 MPa, or from about 170 MPa to about 310 MPa. In some embodiments, the fibers have a toughness of from about 25 MJ/m$^3$ to about 150 MJ/m$^3$, or from about 55 MJ/m$^3$ to about 105 MJ/m$^3$. In some embodiments, the fibers have a β-sheet content of from about 20% to about 60%, or from about 35% to about 45%. In some embodiments, the synthesized spidroin has a molecular weight of at least about 300 kDa, at least about 400 kDA, at least about 500 kDa, or at least about 600 kDa. In some embodiments, the fibers have an extensibility of from about 5% to about 35%, or from about 10% to about 25%.

In some embodiments, a system for synthesizing a spidroin in vivo comprises: a host cell; a seed cassette encoding a seed protein comprising a C-terminus $Int^N$ domain; and a monomer cassette encoding a monomer comprising an N-terminus $Int^C$ domain and a C-terminus $Int^N$ domain. In some embodiments, the host cell is E. coli, or other protein expressing microbial hosts. In some embodiments, the monomer contains a fragment of silk amino acid sequence from N. clavipes spidroin or other spider species.

Results and Discussion

SI-Based Polymerization of Dragline Spider Silk Proteins in E. coli.

Initially, production of HMW repetitive material proteins in E. coli was demonstrated via unseeded SI-based polymerization of dragline spider silk proteins (spidroins). As a proof of concept, a 27.5 kDa "monomer" containing 10 repeats of a Nephila clavipes MaSp1 dragline spidroin consensus sequence with a histidine tag was employed for protein detection and purification. The sequence was genetically optimized for efficient expression in E. coli and flanked by a pair of complementary, fast reacting gp41-1 SIs in the form of $Int^C$-monomer-$Int^N$ (see FIGS. 27A and 27B and FIGS. 17A and 17B), where $Int^C$ and $Int^N$ represent the C- and N-half SIs, respectively.

Figure 27A:
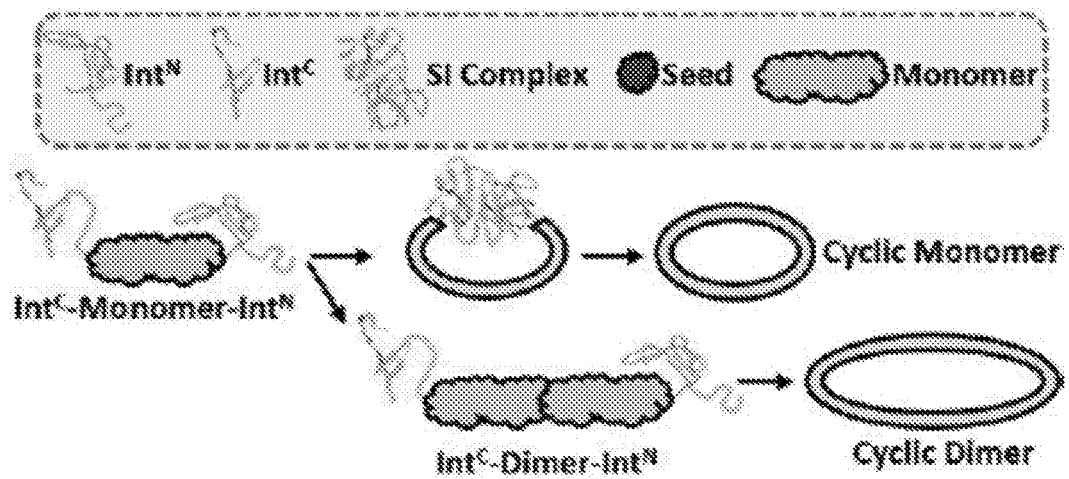
FIG. 27A and FIG. 27B are exemplary embodiments of process schematics for unseeded ligation and seeded chain-growth polymerization (SCP) in accordance with the present disclosure.
Figure 27B:
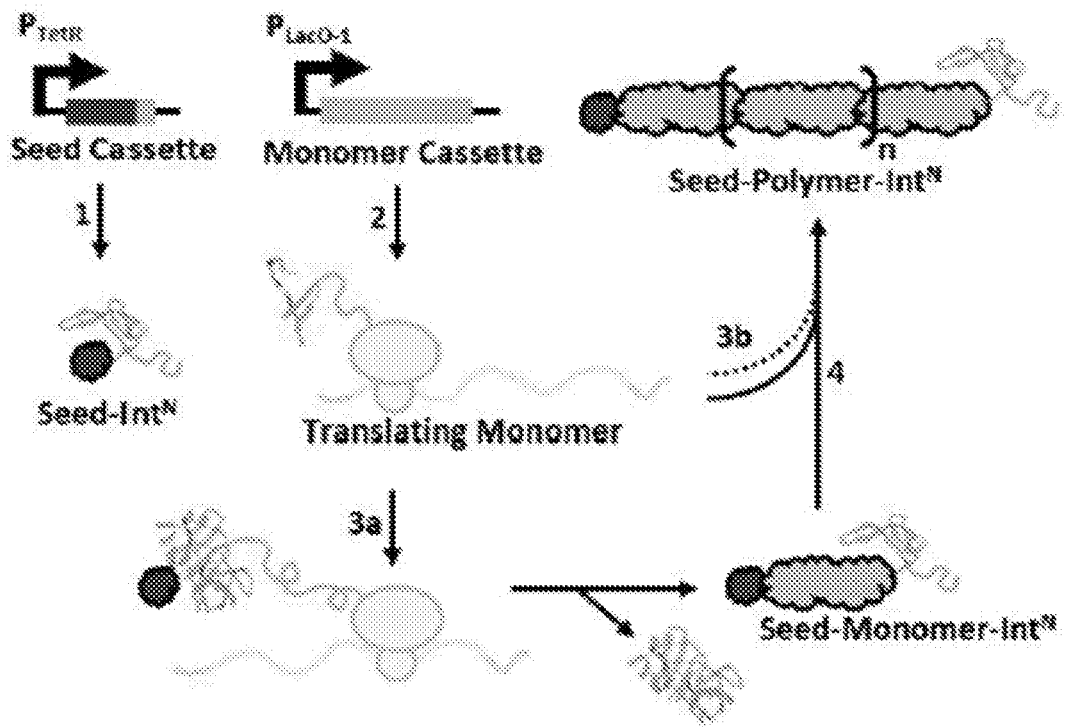

FIGS. 27A and 27B show process schematics for unseeded ligation and seeded chain-growth polymerization (SCP). (A) When expressed in living *E. coli* cells, SI-flanked dragline spidroins ($Int^C$-monomer-$Int^N$) preferentially undergo self-ligation with production of low MW cyclic byproducts. (B) SCP begins with expression of a seed protein (Seed-$Int^N$) (1). After sufficient seed is produced, monomer ($Int^C$-monomer-$Int^N$) is induced (2) and nascent $Int^C$ at the N-termini of monomers reacts co-translationally with seeds (3a) or growing linear chains (3b) before the monomer C-terminal $Int^N$ is translated, effectively eliminating cyclization and producing HMW linear polymer (Seed-Polymer-$Int^N$) (4).

As described herein above, FIGS. 17A and 17B show schematics of SI-Bricks monomer and seed cassettes needed for in vivo seeded chain-growth polymerization (SCP). In FIG. 17A the monomer cassette is controlled by an IPTG-inducible $P_{LacO1}$ promoter and contained on a plasmid with a chloramphenicol resistance gene and a pBBR1 replication origin. In FIG. 17B the seed cassette is controlled by an ATc-inducible promoter and contained on a plasmid carrying kanamycin resistance and a p15A replication origin.

This "monomer cassette" was placed under the control of an IPTG-inducible $P_{LacO1}$ promoter and induced for expression during exponential growth. Anti-His-Tag western blotting was used to analyze products, which revealed primarily low MW oligomers (see FIG. 16B).

As described above, FIG. 16B shows Split Intein (SI) mediated unseeded in vivo ligation of *N. clavipes* dragline spidroin. Western blot of whole cell lysates from cultures producing SI-flanked spidroin monomers without seed protein. Only low MW, cyclic oligomers were produced. Expected sizes of the cyclic products are noted in parentheses. "10x" indicates monomer, subscript "C" indicates cyclic products, and subscript numbers indicate the number of reacted monomers within the product.

These products ran slightly faster than expected for linear products, suggesting the formation of cyclic proteins instead of linear HMW products. SI-catalyzed protein cyclization has been reported, with products migrating faster than linear proteins on SDS-PAGE. Intramolecular cyclization is preferred over intermolecular ligation if monomer structural flexibility permits N- and C-termini to reach reactive proximity. In the case of the *N. clavipes* MaSp1 dragline spidroin, its observed intrinsically disordered structure may promote cyclization over linear polymerization.

Development of SCP for Production of HMW Linear Dragline Spidroins in *E. coli*.

To prevent cyclization and shift production toward HMW linear spidroins, SCP was devised to mimic chain-growth polymerization reactions commonly employed in organic polymer synthesis by first inducing a "seed protein," which contains only one reactive $Int^N$ domain fused at the C-terminus of the seed (FIG. 27B). After a certain time, the $Int^C$-monomer-$Int^N$ cassette is subsequently expressed. The gp41-1 SI has a ligation rate of 0.14 s-1 at 37° C. (corresponding to a ligation half-life of 4.9 s), faster than complete translation of the monomer protein (approximately 21 s based on an average protein translational rate of 12 residues per second). Thus, provided sufficient intracellular concentrations of reactive seed or growing linear chains, the $Int^C$ domain at the N-terminus of a nascent monomer reacts with a seed or linear chain before its C-terminal $Int^N$ domain can be translated, resulting in linear intermolecular ligation without cyclization. To test the possibility of co-translational SI ligation in living bacterial cells, the non-repetitive N-terminal domain of *N. clavipes* MaSp1 dragline silk (termed NTD, 25.2 kDa) was chosen as the seed for polymerization. $Int^N$ was genetically fused to the C-terminus of NTD, yielding a "seed cassette" in the form of NTD-$Int^N$ (see FIG. 27B and FIG. 19B). To control seed production separately from the monomer cassette, NTD-$Int^N$ was placed 3' of a $P_{Tet}$ promoter. Given the similarity in MW of the seed cassette and 10× monomer cassette, for all SCP experiments, a 20 kDa monomer cassette containing 7 repeats of the *N. clavipes* dragline consensus sequence was employed.

Optimization of SCP.

To optimize SCP reaction conditions in *E. coli*, cells were induced with a range of anhydrotetracycline (ATc) concentrations (50-175 nM) for seed synthesis followed by the addition of 1 mM IPTG to induce monomer cassette (FIGS. 19A, 19C, and 23). At low ATc concentration (50 nM), excess monomer production led to cyclic monomer and dimer accumulation. When seed synthesis was highly induced (175 nM ATc), excess seed co-existed with linear protein polymers throughout the time course. At intermediate ATc concentrations (100-125 nM), seed protein was mostly consumed by the end of the time course, and HMW linear products in the form of NTD-$(7x)_n$-$Int^N$ were continuously produced, indicating successful chain-growth polymerization. Under optimized conditions (125 nM ATc), SCP yielded linear products up to 326 kDa (equivalent to 15 cycles of ligation, FIG. 19C), reaching the size of the largest natural dragline spidroins.

FIGS. 19A, 19C, and 23 show protein polymer produced by SCP in *E. coli*. (a) Western blots transferred from 15% SDS-PAGE gels of whole cell lysates taken from shake flask cultures at the indicated times after ATc induction. Cultures were induced at OD 2.0 in exponential growth with ATc at the indicated concentrations ranging from 50-175 nM. Cultures were subsequently induced with 1 mM IPTG 1 h after ATc induction. Expected sizes of products are indicated in parentheses at far right. Each "mer" unit refers to a 7x, 20 kDa dragline spidroin subunit used for polymerization. (b) Western blot transferred from a 5% SDS-PAGE gel comparing products from unseeded polymerization to optimized seeded conditions (125 nM ATc). (c) MW distributions of seeded and unseeded polymerization products. Distributions were calculated using purified proteins after ion exchange chromatography (see FIGS. 20A-B, 26, 28A-C, and 29). Error bars represent standard deviation from three MW analyses.

As described above, FIG. 26 shows Coomassie blue-stained SDS-PAGE gels used for analysis of molecular weight distribution. Products of seeded and unseeded polymerizations after purification by cation exchange chromatography were run in three separate lanes. Band intensities were calculated in the AzureSpot 2.0 1D gel analysis tool, using manual band selection and automatic lane edge subtraction for background removal. During cation exchange, some lower MW oligomers and the seed protein were removed due to the net negative charge of the seed protein at pH 8.0, whereas the spider silk protein has a net positive charge at this pH (Supplementary Table 1). Thus, products after ion exchange chromatography are more enriched for HMW proteins compared to FIGS. 20A-B and 29.

Figure 28A:
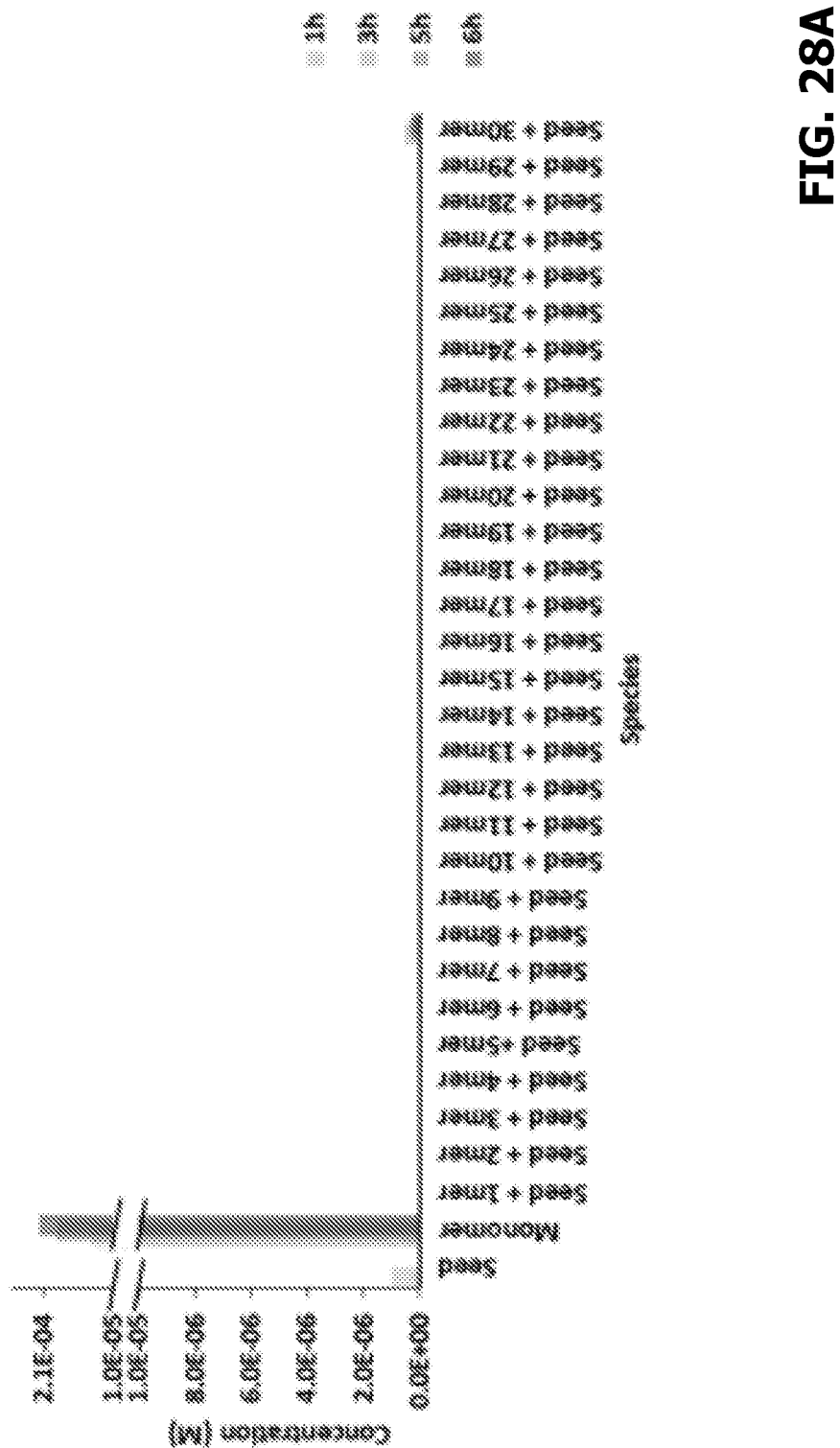
FIG. 28A, FIG. 28B, and FIG. 28C are exemplary embodiments of SCP molecular weight distributions predicted by kinetic model in accordance with the present disclosure.
Figure 28B:
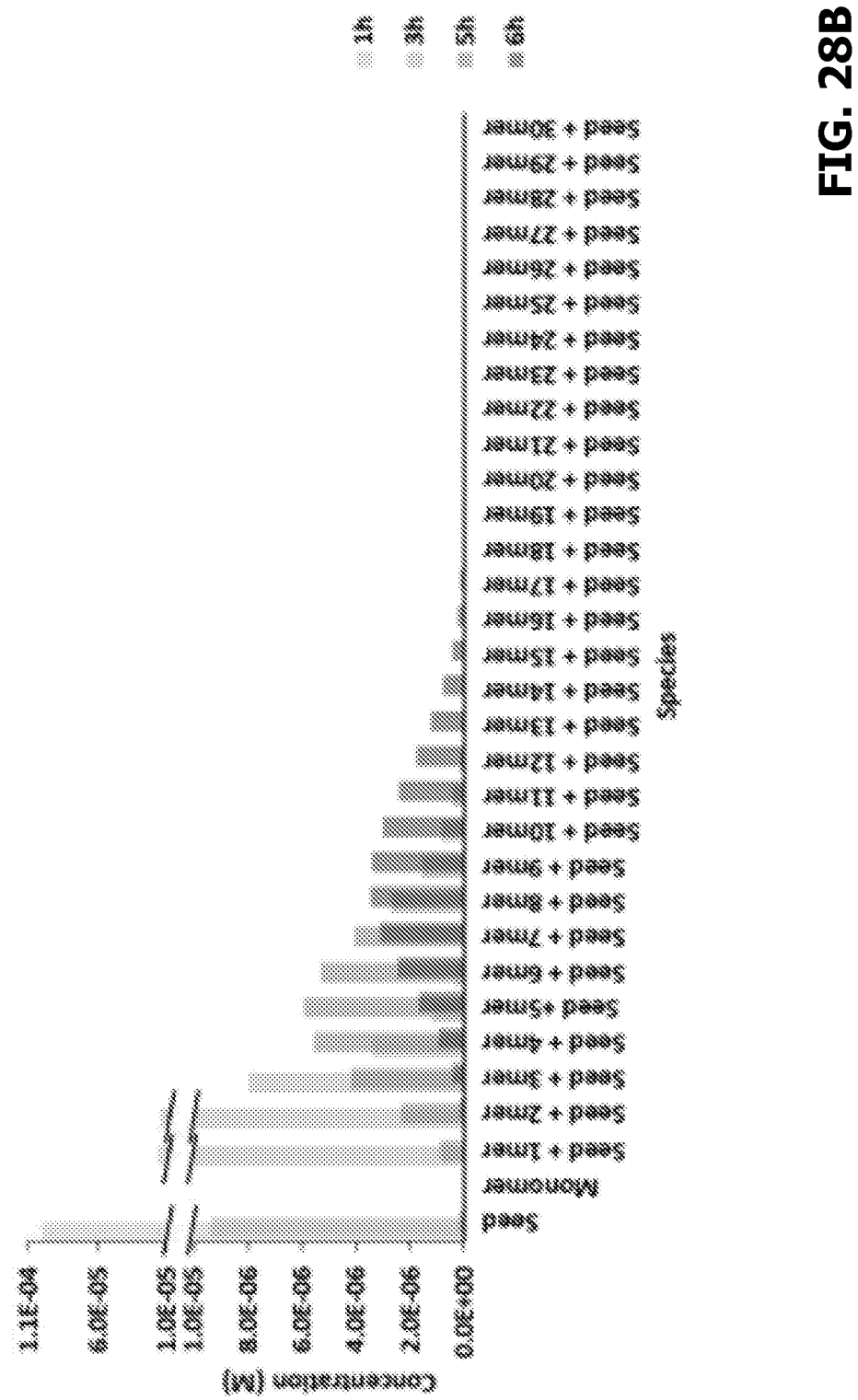
Figure 28C:
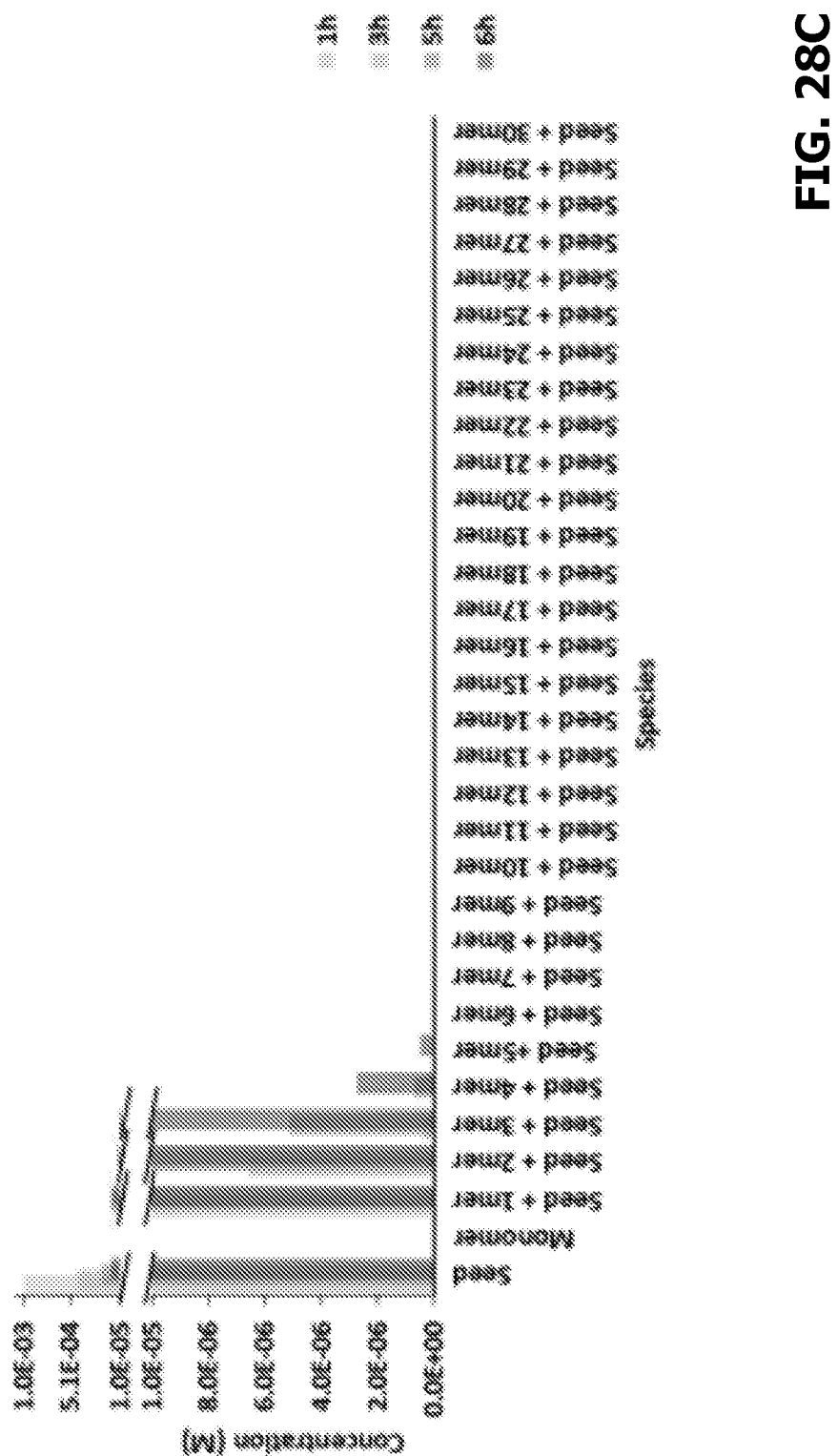

FIGS. 28A-28C show SCP molecular weight distributions predicted by kinetic model. Product distributions were predicted for relatively low (a, 1 µM), moderate (b, 100 µM), and high (c, 1000 µM) seed induction levels. Other parameters were held constant as described herein above and in Table 16.

Figure 29:
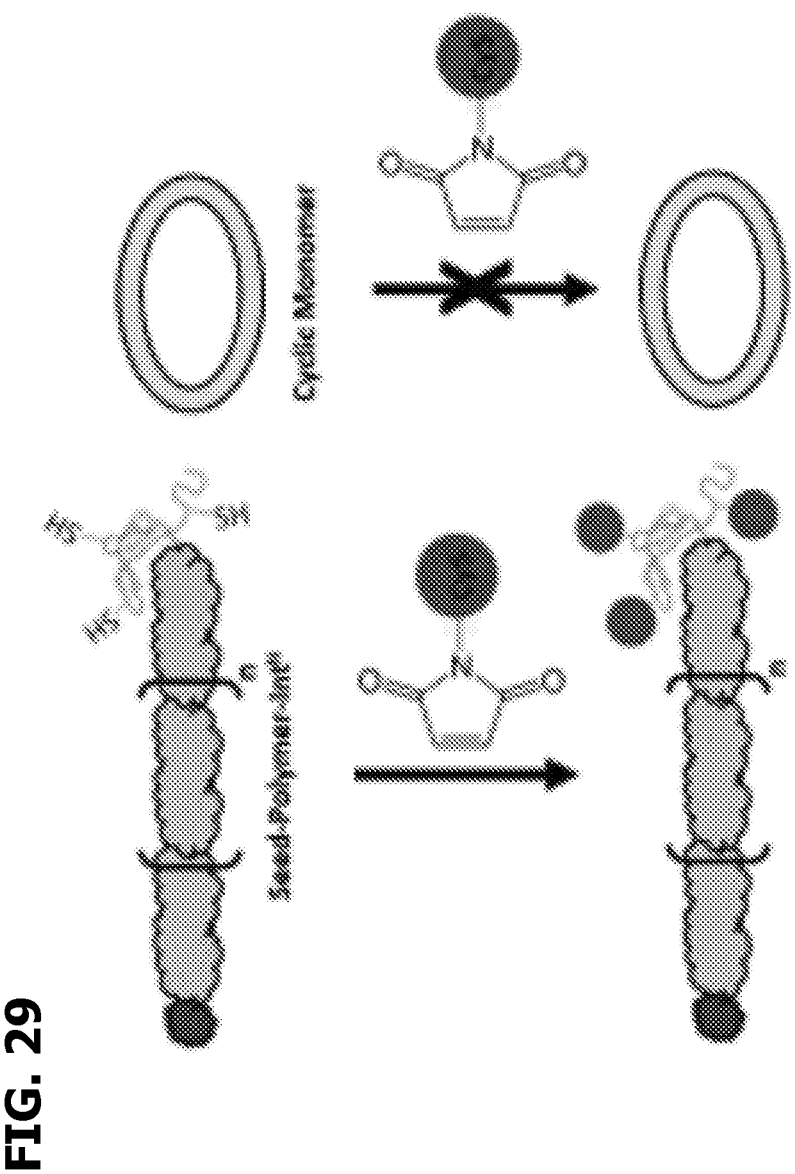
FIG. 29 is an exemplary embodiment of SCP enabling production of primarily linear HMW silk proteins in accordance with the present disclosure.

FIGS. 20A-B and 29 show SCP enables production of primarily linear HMW silk proteins. (FIG. 29) Schematic depiction of maleimide-cy5 labelling. (FIG. 20A) Coomassie Blue-stained SDS-PAGE gel (12% acrylamide) showing products of in vivo polymerization of a 7-mer dragline silk subunit polymerized with ("seeded") or without ("unseeded") application of the SCP method. Products are shown after purification by nickel-affinity chromatography. (FIG. 20B) Products were reacted with a sulfo-Cy5 maleimide fluorescent probe to identify linear polymerization products given that cysteine residues are only present in the IntN domain. Expected MWs of products are indicated in parentheses. "7x" indicates monomer, "NTD" indicates seed, subscript "c" indicates cyclic products, and subscript numbers indicate the number of reacted monomers within the product.

MW Distribution of Spidroins Produced Via SCP.

Further MW analysis of purified SCP products suggested a mass-average MW ($M_w$) of 147±6 kDa and a poly dispersity index (PDI) of 1.5, while the purified unseeded polymerization products exhibit Mw of only 52±4 kDa and a PDI of 1.3 (FIG. 23). Both the $M_w$ and PDI values of the SCP products are comparable to those observed for organic polymers produced via chain-growth polymerization. To better understand the kinetic process of SCP and permit insight into the factors that may affect product distribution, a simple kinetic model was constructed to examine polymer MW distributions. The modelled polymer MW distributions at relatively low, medium, and high seed induction levels agree closely with experimental observations (see Table 16 and FIGS. 28A-28C)—intermediate seed induction levels are desirable to obtain relatively high MW linear polymers.

To better understand the kinetic process and gain insight into the factors that affect product distribution, a simple kinetic model of SCP was constructed. The model assumes a constant second order ligation rate constant (k) based on reported experimental measurement of in vitro ligation rate between $IntN^{Gp1}$ and $IntC^{Gp1}$. The model also considers time-dependent cell growth rate (p) and monomer production rate (r), which were estimated from experimental measurement of cell growth and GFP production. The model neglects effects of protein aggregation, formation of inclusion bodies, cyclic products from SI side reactions, and metabolic burden from silk synthesis.

TABLE 16

Parameter definitions.

| Parameter | Definition | Value | Source |
|---|---|---|---|
| k | Second order ligation rate constant | $1.45 \times 10^8 M^{-1} h^{-1}$ | Carvajal-Vallejos et al. |
| $S_0$ | Initial seed concentration | low - 1 µM medium - 100 µM high - 1000 µM | — |
| S(t) | Time dependent seed concentration | Determined by equation 1 | — |
| $M_1$(t) | Time dependent monomer concentration | Determined by equation 2 | — |
| $SM_i$(t) | Time dependent polymer concentration of -mer length$_i$ | Determined by equation 3 | — |

The model considers a seed protein (S) of initial concentration ($S_0$) which is consumed and diluted as cells divide:

$$\frac{dS}{dt} = S_0 - [\mu(t) \times S(t)] - [k \times S(t) \times M_1(t)] \quad (1)$$

Monomer ($M_1$) is constantly synthesized, consumed to form polymers ($SM_i$), and diluted as cells divide:

$$\frac{dM_1}{dt} = r(t) - [\mu(t) \times M_1(t)] - \left[k \times M_1(t) \times \sum_{i=0}^{n} SM_i(t)\right] \quad (2)$$

where µ is specific cell growth rate, r is monomer synthesis rate, k is the second order ligation rate constant, and $SM_i$ is the concentration of polymer containing N-terminal seed and i copies of monomer. Polymer production is calculated by considering each species' generation, consumption, and dilution. Polymers with molecular weights up to 626 kDa (Seed+30mer) were considered:

$$\frac{dSM_i}{dt} = [k \times M_1(t) \times SM_{i-1}(t)] - [\mu(t) \times SM_i(t)] - [k \times SM_i(t) \times M_1(t)] \quad (3)$$

Polymer distributions at relatively low, medium, and high seed induction levels were simulated and the results are shown in FIGS. 28A-28C. At low seed induction level, seed is rapidly consumed and converted to UHMW linear polymers with accumulation of relatively high concentrations of monomer. At high seed induction levels, seed protein is never fully consumed, and only low MW oligomers are produced. At intermediate seed induction levels, a substantial proportion of relatively high MW linear polymers up to approximately 350 kDa (16mer) can be produced with near complete consumption of seed and little accumulation of monomer. Thus, the modeling results qualitatively agree with experimental observations shown in FIGS. 19A, 19C, and 23.

Confirmation of Elimination of Cyclic Byproducts by SCP.

To confirm the observed polymerization products are in fact cyclic or linear, a cysteine-specific fluorescent labeling reaction was employed. Neither the NTD nor silk monomer contain cysteine residues, while the $Int^N$ sequence contains three cysteines. Because all linear products contain an unreacted C-terminal $Int^N$, the linear products are fluorescently labeled at their cysteine sidechains, while cyclic products, which no longer contain SIs, are not. To label the polymerization products, overexpressed proteins were purified by nickel-affinity chromatography and reacted with a maleimide-Cy5 dye that specifically reacts with the thiol group of cysteine. Subsequent fluorescence imaging of products resolved by SDS-PAGE revealed that linear products were formed only when SCP was employed, while unseeded polymerization produced cyclic products that exhibited no detectable fluorescent labeling (FIGS. 20A-B and 29). These results further confirmed that SCP can effectively eliminate cyclic products and produce HMW linear spidroins.

Mechanical Properties of Wet-Spun Fibers from Seeded Spidroins.

To demonstrate the practical value of producing HMW linear spidroins via SCP, polymerized protein products were purified from *E. coli* native proteins using nickel-affinity and ion-exchange chromatography. The purified HMW spidroins were then lyophilized, dissolved in hexafluoroisopropanol (HFIP), and spun into fibers following standard methods (see methods). In brief, lyophilized powder was dissolved in HFIP to 20% w/v and extruded into a methanol bath. After post-spin draw, fibers were mounted to test frames and tensile tests were used to evaluate the mechanical performance of these fibers. While fibers from the unseeded, cyclic spidroins displayed very weak mechanical performance, fibers from the SCP-produced spidroins displayed greatly enhanced fiber strength (245±63 MPa), modulus (4.1±1.1 GPa), and toughness (80±20 MJ/m$^3$), representing 24-, 41-, and 89-fold enhancements compared to those from unseeded spidroins, respectively (FIG. 24).

As described above, FIG. 24 shows that SCP greatly enhances mechanical properties of resulting fibers. Mechanical properties of wet-spun fibers were assessed by standard tensile tests. Fibers produced from seeded polymers displayed 24-, 41-, and 89-fold higher strength, modulus, and toughness, respectively, relative to unseeded polymers.

Additionally, fibers produced from unseeded polymers were quite brittle, typically fracturing at approximately 10% elongation, while fibers produced from SCP exhibited substantial extensibility, with typical breaking strains >30%. The observed enhancements in mechanical properties are likely the result of the drastically increased MW of SCP products. Indeed, a positive correlation between MW and strength/modulus of dragline spidroin fibers is well documented. It is also worth noting that the linear polymers produced herein contain a 6× histidine tag in each monomer unit and an Int$^N$ sequence at their C-termini. Despite the presence of these sequences, high strength, modulus, and toughness are still obtained. These results clearly demonstrate the value of SCP as a strategy to biosynthesize HMW, highly repetitive spidroins from relatively small, genetically stable sequences in a one-step fermentation process.

Structural Analysis of Fibers Produced from Seeded Polymers.

To further elucidate the benefits of employing SCP, structural differences were next examined between fibers produced by the two polymerization methods using Fourier-transform infrared spectroscopy (FT-IR) and scanning electron microscopy (SEM). Interestingly, comparison of FT-IR spectra of fibers spun from seeded and unseeded polymers suggests relatively little difference in secondary structure. Deconvolutions of the amide I band suggest both fibers consist of roughly 25-30% β-sheet secondary structure, which is typical of both natural and synthetic dragline spidroins (FIGS. 25A-25C).

As described above, FIGS. 25A-25D show secondary structure and morphology of fibers produced by SCP or unseeded polymerization. Deconvolution of FT-IR amide I bands from fibers produced using seeded (FIG. 25A) or unseeded methods (FIG. 25B). Experimentally recorded spectra are shown as solid black lines, while the sums of deconvolved components "fit" are shown as dotted grey lines. (FIG. 25C) Average secondary structure percentages determined from the deconvolution of FT-IR spectra. (FIG. 25D) Representative SEM micrographs of fibers produced from seeded and unseeded spidroin polymers.

These results suggest that neither MW nor cyclization of dragline spidroin polymers substantially affect β-sheet formation during the wet-spinning process and that differences in β-sheet content are not the main factor contributing to the observed mechanical differences of the synthetic fibers.

Meanwhile, comparison of SEM micrographs of the fibers produced by the two methods revealed marked differences in microscale morphology, with fibers produced from unseeded polymers exhibiting relatively smooth, flat fracture surfaces, while fibers produced from seeded polymers exhibit a noticeably rougher, more uneven fracture surface (FIG. 25D). The smooth, flat fracture surfaces of the fibers produced from unseeded spidroins is due to the very low MW of the constituent polymers. The entanglement MW ($M_e$) for silkworm fibroins has been estimated at approximately 66 kDa. Assuming similar $M_e$ for dragline spidroins, the $M_w$ of the unseeded polymers is well under the critical MW for onset of entanglements ($M_c$=2$M_e$). Reports of crack propagation in semi-crystalline polymers show that crazing and chain pullout are generally not observed at $M_w$<$M_c$. Crazing in polymer fibers is a potentially reversible toughening mechanism characterized by formation of microscopic voids bridged by polymer fibrils at a region of concentrated stress. Thus, the fibers from unseeded spidroins fractured without crazing, which allowed for rapid, direct crack propagation leading to relatively smooth, flat fracture surfaces. Meanwhile, the $M_w$ of the seeded polymers is well above the $M_e$ for silk fibroins, such that crazing and chain pullout at the crack front are likely to occur during tensile tests, dissipating stress over a larger area, increasing fracture toughness and resulting in rougher, more uneven fracture surfaces. Indeed, such relationships between MW and fracture surface morphologies have been reported for certain organic polymer fibers.

Taken together, herein is described a strategy to perform protein polymerization in living bacterial cells and demonstrates the production of linear spidroin polymers with MW up to at least 326 kDa—roughly the size of the largest natural dragline spidroins. SCP allows multiple rounds of SI-catalyzed ligation reactions in a single microbial culture, significantly reducing the number of steps that in vitro ligation would otherwise require to obtain products with similar MW and thus greatly decreasing process complexity and increasing potential scalability of fiber production. Furthermore, SCP permits production of highly repetitive proteins from much smaller, more genetically stable and easily expressed subunits, which facilitates practical production of high performance PBMs for industrial applications. In the case of spidroin, although SCP yields a mixture of product MW and the monomer sequence contains a 6× histidine tag that may affect fiber properties, fibers spun from this mixture nonetheless exhibited high strength, modulus, and toughness. Continued optimization of SCP parameters such as monomer sequence and size, SI reaction rate, culture temperature, and induction timing may permit production of spidroins of even higher MW, yield, and mechanical performance. Lastly, the modularity of SCP makes it possible to be applied to numerous other highly repetitive HMW PBMs, further advancing PBM production for materials applications.

Materials and Methods

Strains and Growth Conditions.

For plasmid cloning and protein production, *E. coli* NEB 10-beta (NEB10β) was used. Strains were cultured in Terrific Broth (TB) containing 24 g/L yeast extract, 20 g/L tryptone, 0.4% v/v glycerol, 17 mM KH2PO4, and 72 mM K2HPO4 at 37° C. with appropriate antibiotics (50 µg/mL kanamycin and/or 30 µg/mL chloramphenicol).

Chemicals and Reagents.

Unless otherwise noted, reagents were obtained from MilliporeSigma. Plasmid purification and gel extraction kits were obtained from iNtRON Biotechnology. FastDigest restriction enzymes and T4 DNA ligase were purchased from Thermo Fisher Scientific and used for all digestions and ligations following the manufacturer's suggested protocols.

Genetic Assembly of Monomer and Seed Cassettes.

To construct the 10x and 7x monomer cassettes, 10 or 7 repeats of the *N. clavipes* MaSp1 dragline spidroin (Table 17) were computationally designed, flanked at the 5' end by KpnI and at the 3' end by Kpn2I, and sequence optimized as described herein elsewhere. Optimized sequences were chemically synthesized by Integrated DNA Technologies. The synthesized sequences were separately inserted between KpnI and Kpn2I restriction sites of a medium copy (pBBR1 replication origin), chloramphenicol resistance ($Cm^R$) SI-Bricks expression vector containing optimized gp41-1 SI coding sequences (Table 17), resulting in plasmids pB6c-$Int^C$-10x-$Int^N$ (p10x) and pB6c-$Int^C$-7x-$Int^N$ (p7x) (Table 18).

TABLE 18-continued

| Plasmids. | | | | | |
|---|---|---|---|---|---|
| Plasmid Name | ORI | Promoter | Resistance | Gene | Plasmid Source |
| pNTD | p15A | $P_{tet}$ | $Kan^R$ | Native N. clavipes N-terminal domain + gp41-$1^N$ | Present study |

To construct the seed cassette, the amino acid sequence of the NTD of *N. clavipes* dragline spidroin MaSp1 was computationally redesigned for *E. coli* expression and chemically synthesized by Integrated DNA Technologies. The seed sequence was inserted between restriction sites BglII/Kpn2I of a medium copy (p15A replication origin), kanamycin resistance ($Kan^R$) SI-Bricks expression vector

TABLE 17

Amino acid sequences and estimated charges at pH 8 of proteins.

| Name | Sequence | Estimated Charge at pH 8 |
|---|---|---|
| Gp41-1 $Int^C$ | MAKTKMLKKILKIEELDERELIDIEVSGNHLFYANDILTHN (SEQ NO ID: 10) | -2.5 |
| Gp41-1 $Int^N$ | CLDLKTQVQTPQGMKEISNIQVGDLVLSNTGYNEVLNVFPK SKKKSYKITLEDGKEIICSEEHLFPTQTGEMNISGGLKEGMC LYVKE* (SEQ NO ID: 11) | -3.3 |
| 10x MaSp1 Monomer | SSSDVGTHHHHHHAAAAAGGAGQGGYGGLGSQGAGRGGL GGQGAGAAAAAGGAGQGGYGGLGSQGAGRGGLGGQGAG AAAAAGGAGQGGYGGLGSQGAGRGGLGGQGAGAAAAAG GAGQGGYGGLGSQGAGRGGLGGQGAGAAAAAGGAGQGG YGGLGSQGAGRGGLGGQGAGAAAAAGGAGQGGYGGLGS QGAGRGGLGGQGAGAAAAAGGAGQGGYGGLGSQGAGRG GLGGQGAGAAAAAGGAGQGGYGGLGSQGAGRGGLGGQG AGAAAAAGGAGQGGYGGLGSQGAGRGGLGGQGAGAAAA ASGTRSGY (SEQ NO ID: 12) | 8.6 |
| 7x MaSp1 Monomer | SSSDVGTHHHHHHGGGGSAGRGGLGGQGAGAAAAAGGAG QGGYGGLGSQGAGRGGLGGQGAGAAAAAGGAGQGGYGG LGSQGAGRGGLGGQGAGAAAAAGGAGQGGYGGLGSQGA GRGGLGGQGAGAAAAAGGAGQGGYGGLGSQGAGRGGLG GQGAGAAAAAGGAGQGGYGGLGSQGAGRGGLGGQGAGA AAAAGGAGQGGYGGLGSQGAGRGGLGGQGAGAAAAAGG AGQGGYGGLGSQGSGTRSGY (SEQ NO ID: 13) | 6.6 |
| NTD | MAKTKQNTPWSSTELADAFINAFMNEAGRTGAFTADQLDD MSTIGDTIKTAMDKMARSNKSSKGKLQALNMAFASSMAEI AAVEQGGLSVDAKTNAIADSLNSAFYQTTGAANPQFVNEIR SLINMFAQSSANEVSYGGSGTRSGY (SEQ NO ID: 14) | -2.6 |

TABLE 18

| Plasmids. | | | | | |
|---|---|---|---|---|---|
| Plasmid Name | ORI | Promoter | Resistance | Gene | Plasmid Source |
| pB6c | pBBR1 | $P_{LlacO1}$ | $Cm^R$ | — | Lee et al. 2011 |
| pA2k | p15A | $P_{tet}$ | $Kan^R$ | — | Lee etal. 2011 |
| p10x | pBBR1 | $P_{LlacO1}$ | $Cm^R$ | SI-flanked 10-mer N. clavipes dragline spidroin | Present study |
| p7x | pBBR1 | $P_{LlacO1}$ | $Cm^R$ | SI-flanked 7-mer N. clavipes dragline spidroin | Present study | containing optimized gp41-1 $Int^N$, resulting in plasmid pA2k-NTD-$Int^N$ (pNTD) (Table 18).

SCP Optimization.

For SCP optimization, cultures were grown in 50 mL volumes of TB medium in 250 mL shake flasks with orbital shaking. Cultures were initially incubated at 37° C. until reaching an $OD_{600}$=2.0. Cultures were then induced with a range of concentrations of ATc and incubated at 30° C. After 1 h, monomer production was induced by addition of 1 mM IPTG, and cultures were incubated at 30° C. for varied time periods.

Shake Flask Cultures.

Protein production was performed in 2 L shake flasks. Transformants were cultured overnight in 50 mL TB medium at 37° C. on an orbital shaker. Overnight 50 mL cultures were then used to inoculate 500 mL fresh TB medium in 2 L Erlenmeyer flasks at an initial $OD_{600}$=0.08. Cultures were grown at 37° C. with orbital shaking to $OD_{600}$=2. In the case of unseeded polymer production, cultures were induced by addition of 1 mM IPTG and cultured for an additional 6 h at 30° C. with orbital shaking. In the case of SCP, seed production was first induced by addition of 125 nM ATc and cultured for 1 h at 30° C., followed by monomer induction with 1 mM IPTG and continued culturing for an additional 6 h at 30° C.

Protein Purification.

Cell pellets were directly solubilized in lysis buffer (8 M urea, 20 mM potassium phosphate, 10 mM imidazole, pH 7.4). The mixture was stirred overnight at 22° C. and centrifuged at 25,000×g for 20 min. The pellet was discarded, and the supernatant was sonicated for a total of 10 min (70% amplitude, 5 s on, 10 s off). The sonicated supernatant was then centrifuged at 40,000×g for 30 min. The pellet was discarded, and the supernatant was filtered through a 0.2 µm filter. The filtered solution was applied to a 5 mL His-Trap column at a flow rate of 1 mL/min. The column was then washed with 5 CV of wash buffer (lysis buffer+50 mM imidazole), followed by elution with 5 CV of elution buffer (lysis buffer+300 mM imidazole). Eluent was then dialyzed against cation exchange (IEX) binding buffer (8 M urea, 10 mM HEPES, pH 8.0) in 10K MWCO SnakeSkin dialysis tubing (ThermoFisher Scientific). The dialyzed eluent was loaded onto a 5 mL HiTrap SPFF cation exchange column at a flow rate of 1 mL/min. The column was then washed with 5 CV of IEX wash buffer (binding buffer+40 mM guanidinium hydrochloride). Bound proteins were eluted with 5 CV IEX elution buffer (binding buffer+200 mM guanidinium hydrochloride). IEX eluent was then dialyzed extensively against 5% acetic acid at 4° C. in 10K MWCO SnakeSkin dialysis tubing and lyophilized.

SDS-PAGE.

All SDS-PAGE gels were 1 mm thick, discontinuous with 3% stacking gel, and hand cast at the indicated percentages. Samples were prepared at 1 mg/mL or 5 µM total protein in Laemmli sample buffer (2% SDS, 10% glycerol, 60 mM Tris pH 6.8, 0.01% bromophenol blue, 100 µM DTT). Gels were run on Mini-PROTEAN Tetra Cells (Bio-Rad) in 1× Tris-glycine SDS buffer (25 mM Tris base, 250 mM glycine, 0.1% w/v SDS) until just before the dye front exited the gel. Gels were stained in Coomassie Blue solution (50% methanol, 10% w/v acetic acid, 1 g/L Coomassie Brilliant Blue) for a minimum of 1 h at room temperature with gentle agitation and destained in Coomassie Blue destain buffer (40% v/v methanol, 10% v/v acetic acid) for a minimum of 1 h. Gels were imaged on an Azure c600 Imager (Azure Biosystems).

Western Blotting.

Western blotting was performed with an OWL HEP-3 semi-dry electroblotting system (Thermo Scientific). SDS-PAGE gels, blotting paper (10 cm thickness, Bio-Rad), and blotting membrane (PVDF, 0.2 µm pore size, Roche) were soaked for 15 minutes in semi-dry transfer buffer (1× Tris-glycine SDS buffer+20% methanol). Soaking blot sandwiches were stacked onto the OWL system, and proteins were transferred at 20 mA constant current for 1 h. Blots were then washed briefly in 1×TBS Tween (50 mM Tris-Cl pH 7.6, 150 mM NaCl, 0.1% Tween 20) and then blocked in 1×TBS Tween+5% dried milk powder for 2 h with gentle rocking at room temperature. Blots were then soaked overnight at 4° C. with gentle rocking in 1×TBS Tween+2% dried milk and 1:5000 dilution of mouse anti-$H_6$ monoclonal antibody (ThermoFisher). Blots were washed 4 times in 1×TBS Tween and then incubated for 45 min with gentle rocking at room temperature in 1×TBS-Tween+2% dried milk and 1:10000 dilution of goat anti-mouse AzureSpectra 700 antibody (Azure Biosystems). Finally, blots were washed 4 times in 1×TBS-Tween and imaged on an Azure c600 Imager (Azure Biosystems) using the IR700 imaging channel.

Fluorescence Labelling.

After purification by His-Trap affinity chromatography, purified products were dialyzed against 8 M urea, 10 mM HEPES, 100 µM TCEP, pH 7.4, at a final protein concentration of approximately 10 µM. Sulfo-Cyanine5 (Lumiprobe Life science solutions) was pre-dissolved in DMSO at a concentration of 100 mM and then added to the protein solution to a final concentration of 200 µM. The reaction mixture was incubated overnight at 4° C. in dark with periodic mixing. After overnight incubation, the reaction was mixed 1:1 with 2× Laemmli sample buffer, run on an SDS-PAGE, and imaged with an Azure c600 Imager (Azure Biosystems) using the Cy5 channel.

Densitometry Analysis and Calculation of $M_w$, $M_n$, and PDI.

Coomassie stained SDSPAGE gels of polymerization products after ion exchange purification were imaged on an Azure c600 Imager (Azure Biosystems). All quantifications were performed in triplicate. All densitometry analysis was performed with the AzureSpot Analysis Software (Azure Biosystems). Images were background subtracted with a built-in automatic lane edge subtraction algorithm. Protein band intensities were integrated by the AzureSpot software, and apparent MWs were calculated based on MW standards run on the same gels. Integrated band intensities were normalized against the highest band intensity in a given MW distribution. Averages of three normalized integrated band intensities along with the standard deviation of the three normalized values were plotted against MW. Number-average MW ($M_n$) was calculated as $Mn=\Sigma M_i N_i/\Sigma$, where $\Sigma M_i N_i$ is treated as the sum of each species' MW ($M_i$) multiplied by its integrated band intensity ($N_i$), and $\Sigma N_i$ is the sum of all band intensities. Weight-average MW ($M_w$) was calculated as $M_w=\Sigma w_i M_i$, where $w_i$ is the weight fraction of each species calculated as the total weight of a species ($M_i N$) divided by the total weight of all species ($\Sigma M_i N_i$). Lastly, PDI was calculated as the ratio of $M_w$ to $M_n$.

Fiber Spinning and Mechanical Testing.

Fiber spinning and mechanical testing were performed following a protocol modified from known methods. Specifically, lyophilized spidroin powders were dissolved in HFIP to 20% w/v. This protein dope was loaded to a 100 µL Hamilton gastight syringe (Hamilton Robotics). The syringe was fitted to a Harvard Apparatus Pump 11 Elite syringe pump (Harvard Apparatus), and the dope was extruded into a 95% v/v methanol bath at 5 µL/min. Extruded fibers were then transferred to a 75% v/v methanol bath and carefully extended at approximately 1 cm/s to the maximum draw ratio without fiber fracture. Extended fibers were removed from the bath and held under tension until visibly dry. Segments of post-drawn fibers (20 mm) were carefully laid exactly vertical across a 5 mm (vertical)×15 mm (horizontal) opening cut into a 20 mm×20 mm piece of cardstock and fixed with adhesive tape at both ends of the opening. Diameters of mounted fibers were then measured by light microscopy, averaging measurements at three points along the fiber axis (see Table 13 and Table 14).

Mechanical properties were measured by axial pull tests on an MTS Criterion Model 41 universal test frame fitted with a 1 N load cell (MTS Systems Corporation). Cardstock holders were mounted between two opposing spring-loaded grips, and the supporting edges were carefully cut. Pull tests were conducted at a relative humidity of 30% and temperature of 22° C., with a constant crosshead speed of 10 mm/min. Stress-strain curves were recorded by the MTS TW Elite test suite at a sampling rate of 50 Hz. Fiber breaks were recorded when a 90% drop from peak stress was detected. All mechanical properties were automatically calculated by the MTS TW Elite test suite. Ultimate tensile strength was calculated as the maximum measured load over the initial fiber cross-sectional area ($A=\pi r^2$), as determined from measured initial diameters. Modulus was calculated as the slope of a linear least squares fit to the stress/strain data of the initial elastic region. Toughness was calculated as the area under the total stress/strain curve divided by the initial fiber volume ($V=\pi r^2 h$) as calculated from measured initial fiber diameters and set initial gage length of 5 mm. For each protein, a total of 10 fibers were measured in this manner.

Light Microscopy.

Fiber diameters were measured using images acquired with a Zeiss Axio Observer ZI Inverted Microscope equipped with a phase contrast 20× objective lens and the Axiovision LE software (Zeiss).

Scanning Electron Microscopy.

Following tensile tests, silk fibers were mounted onto a sample holder using conductive tape. The sample holder was sputter coated with a 10 nm gold layer using a Leica EM ACE600 high vacuum sputter coater (Leica Microsystems). Fibers were imaged using a Nova NanoSEM 230 Field Emission Scanning Electron Microscope (Field Electron and Ion Company, FEI) at an accelerating voltage of 7-10 kV.

Fourier Transform Infrared Spectroscopy.

For secondary structure determination, FTIR spectra were acquired with a Thermo Nicolet 470 FT-IR spectrometer (ThermoFisher Scientific) fitted with a Smart Performer ATR accessory with Ge crystal. Spectra were acquired from 1350-1750 $cm^{-1}$ at 4 $cm^{-1}$ resolution. A total of 254 scans were accumulated for each sample. All recorded spectra were analyzed using Fityk 0.9.8. Baselines were subtracted from all spectra using the built-in Fityk convex hull algorithm. The amide I band (1600-1700 $cm^{-1}$) was deconvolved into a set of eleven Lorentzian peaks centered at 1610, 1618.5, 1624.5, 1632.5, 1642, 1651, 1659, 1666.5, 1678, 1690.5, and 1700 $cm^{-1}$, corresponding to amide I shifts characteristic of either β-sheet, random coil, α-helix, or β-turn. Specific assignments are listed in Table 15. Peak areas were integrated, and component percentages were calculated as the component peak area over the sum of all peak areas. Percentages were averaged from measurements of three fibers each for unseeded and seeded polymers.

Abbreviations

PBMs: protein-based materials, MW: molecular weight, HMW: high molecular weight, SI: split intein, *N. clavipes: Nephila clavipes, E. coli: Escherichia coli*, IPTG: Isopropyl β-D-1-thiogalactopyranoside, SCP: seeded chain-growth polymerization, NTD: *N. clavipes* N-terminal domain, ATc: anhydrotetracycline, SDS-PAGE: sodium dodecyl sulfate-polyacrylamide gel electrophoresis, HFIP: hexafluoroisopropanol, Mn: number average molecular weight, Mw: weight average molecular weight, PDI: poly dispersity index, SEM: scanning electron microscopy, FT-IR: Fourier transform infrared spectroscopy, $M_e$: entanglement molecular weight, $M_c$: critical MW for onset of entanglements.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that vary depending upon the desired properties sought to be obtained by a particular embodiment. In some embodiments, the numerical parameters are be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) are construed to cover both the singular and the plural, unless specifically noted otherwise. In some embodiments, the term "or" as used herein, including the claims, is used to mean "and/or" unless explicitly indicated to refer to alternatives only or to refer to the alternatives that are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and may also cover other unlisted steps. Similarly, any composition or device that "comprises," "has" or "includes" one or more features is not limited to possessing only those one or more features and may cover other unlisted features.

All methods described herein are performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member is referred to and claimed individually or in any combination with other members of the group or other elements found herein. One or more members of a group are included in, or deleted from, a group for reasons of convenience or patentability. When any such inclusion or deletion occurs, the specification is herein deemed to contain the group as modified thus fulfilling the written description of all Markush groups used in the appended claims.

To facilitate the understanding of the embodiments described herein, a number of terms are defined below. The terms defined herein have meanings as commonly understood by a person of ordinary skill in the areas relevant to the present disclosure. Terms such as "a," "an," and "the" are not intended to refer to only a singular entity, but rather include the general class of which a specific example may be used for illustration. The terminology herein is used to describe specific embodiments of the disclosure, but their usage does not delimit the disclosure, except as outlined in the claims.

All of the compositions and/or methods disclosed and claimed herein may be made and/or executed without undue experimentation in light of the present disclosure. While the compositions and methods of this disclosure have been described in terms of the embodiments included herein, it will be apparent to those of ordinary skill in the art that variations may be applied to the compositions and/or methods and in the steps or in the sequence of steps of the method described herein without departing from the concept, spirit, and scope of the disclosure. All such similar substitutes and modifications apparent to those skilled in the art are deemed to be within the spirit, scope, and concept of the disclosure as defined by the appended claims.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for synthesizing a spidroin, the method comprising:
synthesizing a spidroin fragment in vivo in a heterologous host, the spidroin fragment comprising an N-terminus Int$^C$ domain comprising the amino acid sequence of SEQ ID NO: 10 and a C-terminus Int$^N$ domain comprising the amino acid sequence of SEQ ID NO: 11;
producing the spidroin fragment from the heterologous host; and
post-translationally polymerizing the synthesized spidroin fragment via in vitro split-intein mediated polymerization;
wherein the spidroin fragment is a silk amino acid sequence from a spider species.

2. The method of claim 1, wherein the heterologous host is a protein-expressing microbial host.

3. The method of claim 1, wherein the synthesized spidroin has a molecular weight of at least 300 kDa.

4. The method of claim 1, further comprising spinning the synthesized spidroin into fibers.

5. The method of claim 4, wherein the fibers have a tensile strength of from about 0.9 GPa to about 1.3 GPa.

6. The method of claim 4, wherein the fibers have an extensibility of from about 10% to about 25%.

7. The method of claim 4, wherein the fibers have a toughness of from about 60 MJ/m$^3$ to about 170 MJ/m$^3$.

8. The method of claim 4, wherein the fibers have a β-sheet content of from about 35% to about 45%.

9. A method for synthesizing a spidroin, the method comprising:
synthesizing a seed protein in vivo in a heterologous host, the seed protein comprising a C-terminus Int$^N$ domain;

synthesizing a spidroin fragment in vivo in the heterologous host, the spidroin fragment comprising an N-terminus $Int^C$ domain comprising the amino acid sequence of SEQ ID NO: 10 and a C-terminus $Int^N$ domain comprising the amino acid sequence of SEQ ID NO: 11; and co-translationally polymerizing the spidroin fragment via in vivo split-intein mediated polymerization;

wherein the spidroin fragment is a silk amino acid sequence from a spider species.

10. The method of claim 9, wherein the heterologous host is a protein-expressing microbial host.

11. The method of claim 9, wherein the synthesized spidroin is a linear polymer.

12. The method of claim 9, wherein the synthesized spidroin has a molecular weight of at least 300 kDa.

13. The method of claim 9, further comprising spinning the synthesized spidroin into fibers.

14. The method of claim 13, wherein the fibers have a tensile strength of from about 170 MPa to about 310 MPa.

15. The method of claim 13, wherein the fibers have a toughness of from about 55 $MJ/m^3$ to about 105 $MJ/m^3$.

* * * * *

SEQUENCE LISTING

```
<160> NUMBER OF SEQ ID NOS: 14

<210> SEQ ID NO 1
<211> LENGTH: 55
<212> TYPE: DNA
<213> ORGANISM: E. coli

<400> SEQUENCE: 1
atcagcagga cgcactgacc gaattcaaaa gatcttttaa gaaggagata tacat            55

<210> SEQ ID NO 2
<211> LENGTH: 147
<212> TYPE: DNA
<213> ORGANISM: E. coli

<400> SEQUENCE: 2
ggatccaaac tcgagtaagg atctccaggc atcaaataaa acgaaaggct cagtcgaaag       60
actgggcctt tcgttttatc tgttgtttgt cggtgaacgc tctctactag agtcacactg      120
gctcaccttc gggtgggcct ttctgcg                                          147

<210> SEQ ID NO 3
<211> LENGTH: 327
<212> TYPE: DNA
<213> ORGANISM: E. coli

<400> SEQUENCE: 3
tccggagcag aatattgcct gtcttacgac acagagattc tgaccgttga atatggattc       60
cttcctatcg gtaagatcgt ggaggaacgg attgaatgca cagtctatac ggtagataaa      120
aatggctttg tgtatacaca acctattgct cagtggcata accggggaga acaggaagtt      180
ttcgaatact gcttagaaga cggttcgatt atccgtgcaa cgaaagatca caaatttatg      240
acgaccgacg gtcagatgtt accgattgat gagattttcg aacgggggtt agacctgaaa      300
caagttgatg gtttgccgta aggatcc                                          327

<210> SEQ ID NO 4
<211> LENGTH: 161
<212> TYPE: DNA
<213> ORGANISM: E. coli
```

```
<400> SEQUENCE: 4
agatctttta agaaggagat atacatatgg ctaagactaa agtcaagatc attagtcgta      60
agagtctggg cactcaaaac gtctacgata ttggagtaga aaagatcat aatttttgc       120 tgaagaatgg gctggtggcc tctaactgct tcaacggtac c                         161

<210> SEQ ID NO 5
<211> LENGTH: 35
<212> TYPE: DNA
<213> ORGANISM: E. coli

<400> SEQUENCE: 5
cggaacgacg tcaattttc ctggtcacgt aagcg                                  35

<210> SEQ ID NO 6
<211> LENGTH: 34
<212> TYPE: DNA
<213> ORGANISM: E. coli

<400> SEQUENCE: 6
ggctacctcg agttgggtgg tctgtgcttt gcag                                  34

<210> SEQ ID NO 7
<211> LENGTH: 34
<212> TYPE: PRT
<213> ORGANISM: E. coli

<400> SEQUENCE: 7

Ser Gly Arg Gly Gly Leu Gly Gly Gln Gly Ala Gly Met Ala Ala Ala
1               5                   10                  15

Ala Ala Met Gly Gly Ala Gly Gln Gly Gly Tyr Gly Gly Leu Gly Ser
            20                  25                  30

Gln Gly

<210> SEQ ID NO 8
<211> LENGTH: 104
<212> TYPE: PRT
<213> ORGANISM: E. coli

<400> SEQUENCE: 8

Ala Glu Tyr Cys Leu Ser Tyr Asp Thr Glu Ile Leu Thr Val Glu Tyr
1               5                   10                  15

Gly Phe Leu Pro Ile Gly Lys Ile Val Glu Glu Arg Ile Glu Cys Thr
            20                  25                  30

Val Tyr Thr Val Asp Lys Asn Gly Phe Val Tyr Thr Gln Pro Ile Ala
        35                  40                  45

Gln Trp His Asn Arg Gly Glu Gln Glu Val Phe Glu Tyr Cys Leu Glu
    50                  55                  60

Asp Gly Ser Ile Ile Arg Ala Thr Lys Asp His Lys Phe Met Thr Thr
65                  70                  75                  80

Asp Gly Gln Met Leu Pro Ile Asp Glu Ile Phe Glu Arg Gly Leu Asp
                85                  90                  95

Leu Lys Gln Val Asp Gly Leu Pro
            100

<210> SEQ ID NO 9
<211> LENGTH: 39
<212> TYPE: PRT
<213> ORGANISM: E. coli
```

```
<400> SEQUENCE: 9

Met Val Lys Ile Ile Ser Arg Lys Ser Leu Gly Thr Gln Asn Val Tyr
1               5                   10                  15

Asp Ile Gly Val Glu Lys Asp His Asn Phe Leu Leu Lys Asn Gly Leu
                20                  25                  30

Val Ala Ser Asn Cys Phe Asn
                35

<210> SEQ ID NO 10
<211> LENGTH: 41
<212> TYPE: PRT
<213> ORGANISM: E. coli

<400> SEQUENCE: 10

Met Ala Lys Thr Lys Met Leu Lys Lys Ile Leu Lys Ile Glu Glu Leu
1               5                   10                  15

Asp Glu Arg Glu Leu Ile Asp Ile Glu Val Ser Gly Asn His Leu Phe
                20                  25                  30

Tyr Ala Asn Asp Ile Leu Thr His Asn
                35                  40

<210> SEQ ID NO 11
<211> LENGTH: 88
<212> TYPE: PRT
<213> ORGANISM: E. coli

<400> SEQUENCE: 11

Cys Leu Asp Leu Lys Thr Gln Val Gln Thr Pro Gln Gly Met Lys Glu
1               5                   10                  15

Ile Ser Asn Ile Gln Val Gly Asp Leu Val Leu Ser Asn Thr Gly Tyr
                20                  25                  30

Asn Glu Val Leu Asn Val Phe Pro Lys Ser Lys Lys Ser Tyr Lys
                35                  40                  45

Ile Thr Leu Glu Asp Gly Lys Glu Ile Ile Cys Ser Glu Glu His Leu
50                  55                  60

Phe Pro Thr Gln Thr Gly Glu Met Asn Ile Ser Gly Gly Leu Lys Glu
65                  70                  75                  80

Gly Met Cys Leu Tyr Val Lys Glu
                85

<210> SEQ ID NO 12
<211> LENGTH: 313
<212> TYPE: PRT
<213> ORGANISM: E. coli

<400> SEQUENCE: 12

Ser Ser Ser Asp Val Gly Thr His His His His His Ala Ala Ala
1               5                   10                  15

Ala Ala Gly Gly Ala Gly Gln Gly Gly Tyr Gly Gly Leu Gly Ser Gln
                20                  25                  30

Gly Ala Gly Arg Gly Gly Leu Gly Gln Gly Ala Gly Ala Ala Ala
                35                  40                  45

Ala Ala Gly Gly Ala Gly Gln Gly Gly Tyr Gly Gly Leu Gly Ser Gln
                50                  55                  60

Gly Ala Gly Arg Gly Gly Leu Gly Gln Gly Ala Gly Ala Ala Ala
65                  70                  75                  80

Ala Ala Gly Gly Ala Gly Gln Gly Gly Tyr Gly Gly Leu Gly Ser Gln
                85                  90                  95
```

-continued

Gly Ala Gly Arg Gly Gly Leu Gly Gly Gln Gly Ala Gly Ala Ala Ala
            100                 105                 110

Ala Ala Gly Gly Ala Gly Gln Gly Gly Tyr Gly Gly Leu Gly Ser Gln
        115                 120                 125

Gly Ala Gly Arg Gly Gly Leu Gly Gly Gln Gly Ala Gly Ala Ala Ala
        130                 135                 140

Ala Ala Gly Gly Ala Gly Gln Gly Gly Tyr Gly Gly Leu Gly Ser Gln
145                 150                 155                 160

Gly Ala Gly Arg Gly Gly Leu Gly Gly Gln Gly Ala Gly Ala Ala Ala
            165                 170                 175

Ala Ala Gly Gly Ala Gly Gln Gly Gly Tyr Gly Gly Leu Gly Ser Gln
        180                 185                 190

Gly Ala Gly Arg Gly Gly Leu Gly Gly Gln Gly Ala Gly Ala Ala Ala
        195                 200                 205

Ala Ala Gly Gly Ala Gly Gln Gly Gly Tyr Gly Gly Leu Gly Ser Gln
    210                 215                 220

Gly Ala Gly Arg Gly Gly Leu Gly Gly Gln Gly Ala Gly Ala Ala Ala
225                 230                 235                 240

Ala Ala Gly Gly Ala Gly Gln Gly Gly Tyr Gly Gly Leu Gly Ser Gln
            245                 250                 255

Gly Ala Gly Arg Gly Gly Leu Gly Gly Gln Gly Ala Gly Ala Ala Ala
        260                 265                 270

Ala Ala Gly Gly Ala Gly Gln Gly Gly Tyr Gly Gly Leu Gly Ser Gln
        275                 280                 285

Gly Ala Gly Arg Gly Gly Leu Gly Gly Gln Gly Ala Gly Ala Ala Ala
        290                 295                 300

Ala Ala Ser Gly Thr Arg Ser Gly Tyr
305                 310

<210> SEQ ID NO 13
<211> LENGTH: 249
<212> TYPE: PRT
<213> ORGANISM: E. coli

<400> SEQUENCE: 13

Ser Ser Ser Asp Val Gly Thr His His His His His Gly Gly Gly
1               5                   10                  15

Gly Ser Ala Gly Arg Gly Gly Leu Gly Gly Gln Gly Ala Gly Ala Ala
            20                  25                  30

Ala Ala Ala Gly Gly Ala Gly Gln Gly Gly Tyr Gly Gly Leu Gly Ser
        35                  40                  45

Gln Gly Ala Gly Arg Gly Gly Leu Gly Gly Gln Gly Ala Gly Ala Ala
    50                  55                  60

Ala Ala Ala Gly Gly Ala Gly Gln Gly Gly Tyr Gly Gly Leu Gly Ser
65                  70                  75                  80

Gln Gly Ala Gly Arg Gly Gly Leu Gly Gly Gln Gly Ala Gly Ala Ala
            85                  90                  95

Ala Ala Ala Gly Gly Ala Gly Gln Gly Gly Tyr Gly Gly Leu Gly Ser
        100                 105                 110

Gln Gly Ala Gly Arg Gly Gly Leu Gly Gly Gln Gly Ala Gly Ala Ala
        115                 120                 125

Ala Ala Ala Gly Gly Ala Gly Gln Gly Gly Tyr Gly Gly Leu Gly Ser
    130                 135                 140

Gln Gly Ala Gly Arg Gly Gly Leu Gly Gly Gln Gly Ala Gly Ala Ala

```
145                 150                 155                 160
Ala Ala Ala Gly Gly Ala Gly Gln Gly Gly Tyr Gly Gly Leu Gly Ser
                165                 170                 175
Gln Gly Ala Gly Arg Gly Gly Leu Gly Gly Gln Gly Ala Gly Ala Ala
                180                 185                 190
Ala Ala Ala Gly Gly Ala Gly Gln Gly Gly Tyr Gly Gly Leu Gly Ser
                195                 200                 205
Gln Gly Ala Gly Arg Gly Gly Leu Gly Gly Gln Gly Ala Gly Ala Ala
                210                 215                 220
Ala Ala Ala Gly Gly Ala Gly Gln Gly Gly Tyr Gly Gly Leu Gly Ser
225                 230                 235                 240
Gln Gly Ser Gly Thr Arg Ser Gly Tyr
                245

<210> SEQ ID NO 14
<211> LENGTH: 146
<212> TYPE: PRT
<213> ORGANISM: E. coli

<400> SEQUENCE: 14

Met Ala Lys Thr Lys Gln Asn Thr Pro Trp Ser Ser Thr Glu Leu Ala
1               5                   10                  15
Asp Ala Phe Ile Asn Ala Phe Met Asn Glu Ala Gly Arg Thr Gly Ala
                20                  25                  30
Phe Thr Ala Asp Gln Leu Asp Asp Met Ser Thr Ile Gly Asp Thr Ile
            35                  40                  45
Lys Thr Ala Met Asp Lys Met Ala Arg Ser Asn Lys Ser Ser Lys Gly
        50                  55                  60
Lys Leu Gln Ala Leu Asn Met Ala Phe Ala Ser Ser Met Ala Glu Ile
65                  70                  75                  80
Ala Ala Val Glu Gln Gly Gly Leu Ser Val Asp Ala Lys Thr Asn Ala
                85                  90                  95
Ile Ala Asp Ser Leu Asn Ser Ala Phe Tyr Gln Thr Thr Gly Ala Ala
                100                 105                 110
Asn Pro Gln Phe Val Asn Glu Ile Arg Ser Leu Ile Asn Met Phe Ala
            115                 120                 125
Gln Ser Ser Ala Asn Glu Val Ser Tyr Gly Gly Ser Gly Thr Arg Ser
        130                 135                 140
Gly Tyr
145
```